(12) United States Patent
Lampert

(10) Patent No.: US 6,767,207 B1
(45) Date of Patent: Jul. 27, 2004

(54) METHOD OF FABRICATING A FLEXIBLE RETENTIVE BITE BLOCK

(76) Inventor: Barry Lampert, 34 Watchway, Lloyd Harbor, NY (US) 11743

(*) Notice: Subject to any disclaimer, the term of this patent is extended or adjusted under 35 U.S.C. 154(b) by 169 days.

(21) Appl. No.: 10/135,302

(22) Filed: Apr. 29, 2002

(51) Int. Cl.[7] ................................................. A61C 3/00
(52) U.S. Cl. .............................................................. 433/6
(58) Field of Search .............................. 433/6; 128/848, 128/859, 860, 861, 862

(56) References Cited

U.S. PATENT DOCUMENTS

| | | | | |
|---|---|---|---|---|
| 4,505,672 A | * | 3/1985 | Kurz ............................... | 433/6 |
| 4,901,737 A | * | 2/1990 | Toone .......................... | 128/848 |
| 5,003,994 A | * | 4/1991 | Cook ........................... | 128/848 |
| 5,365,945 A | * | 11/1994 | Halstrom .................... | 128/848 |
| 5,409,017 A | * | 4/1995 | Lowe .......................... | 128/848 |
| 5,427,117 A | * | 6/1995 | Thornton .................... | 128/848 |
| 5,499,633 A | * | 3/1996 | Fenton ........................ | 128/848 |
| 5,562,106 A | * | 10/1996 | Heeke et al. ............... | 128/848 |
| 5,816,799 A | * | 10/1998 | Parker ............................ | 433/6 |
| 5,823,194 A | | 10/1998 | Lampert | |
| 6,074,207 A | * | 6/2000 | Coats .......................... | 433/19 |

* cited by examiner

Primary Examiner—Ralph A. Lewis
(74) Attorney, Agent, or Firm—Richard L Miller, P.A.

(57) ABSTRACT

A dentally retained intra-oral appliance worn at night for treatment of snoring and obstructive sleep apnea and its fabrication process. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscles and ligaments. The appliance includes a lower bite block conforming to the patient's mandibular dentition, an upper bite block conforming to the patient's maxillary dentition, and a hinge connecting the upper bite block to the lower bite block. The upper bite block and the lower bite block are thin walled polyamide eliminating the need for dental wires to maintain them to the mandibular detention and the maxillary dentition and the problems associated therewith.

19 Claims, 98 Drawing Sheets

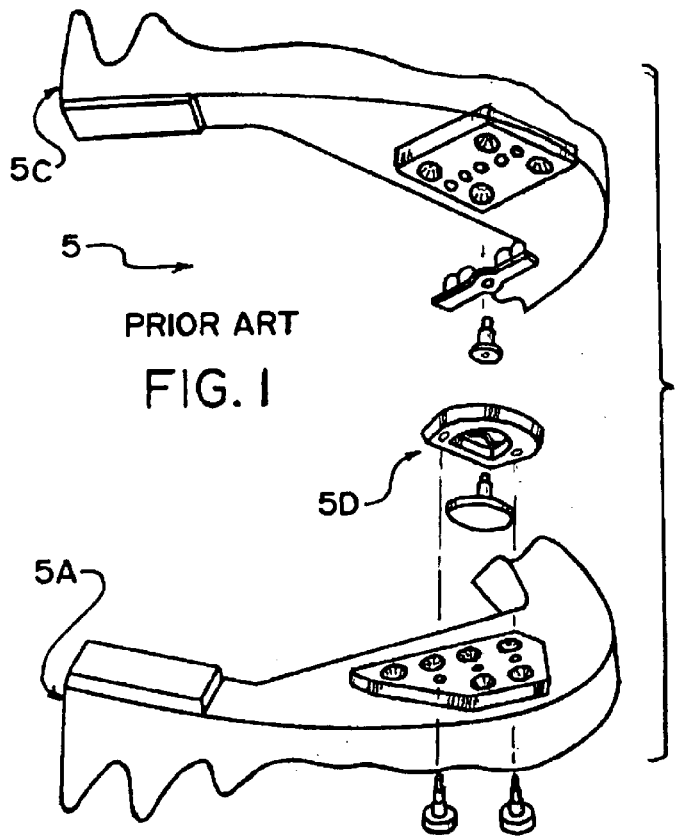
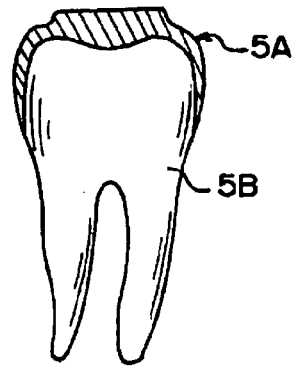
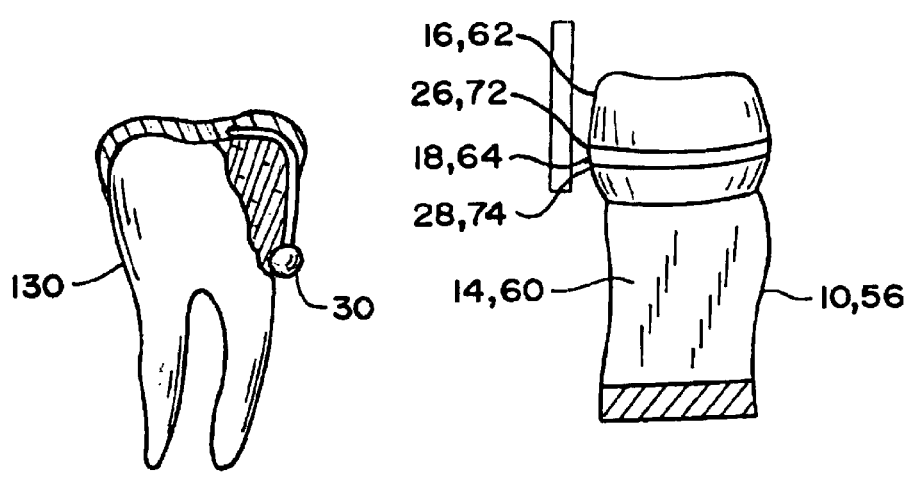
PRIOR ART
FIG. 1
PRIOR ART
FIG. 2
FIG. 11
FIG. 3

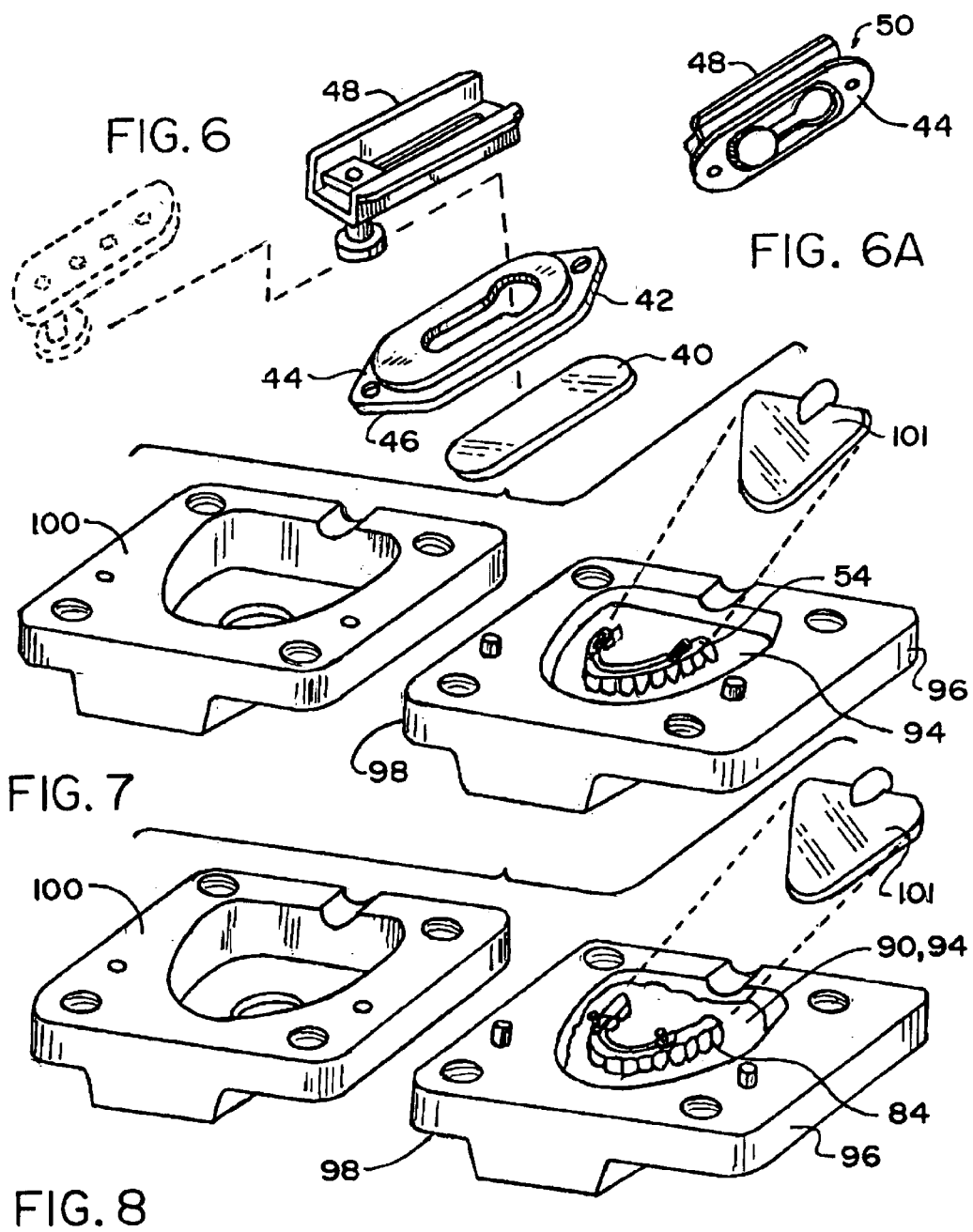

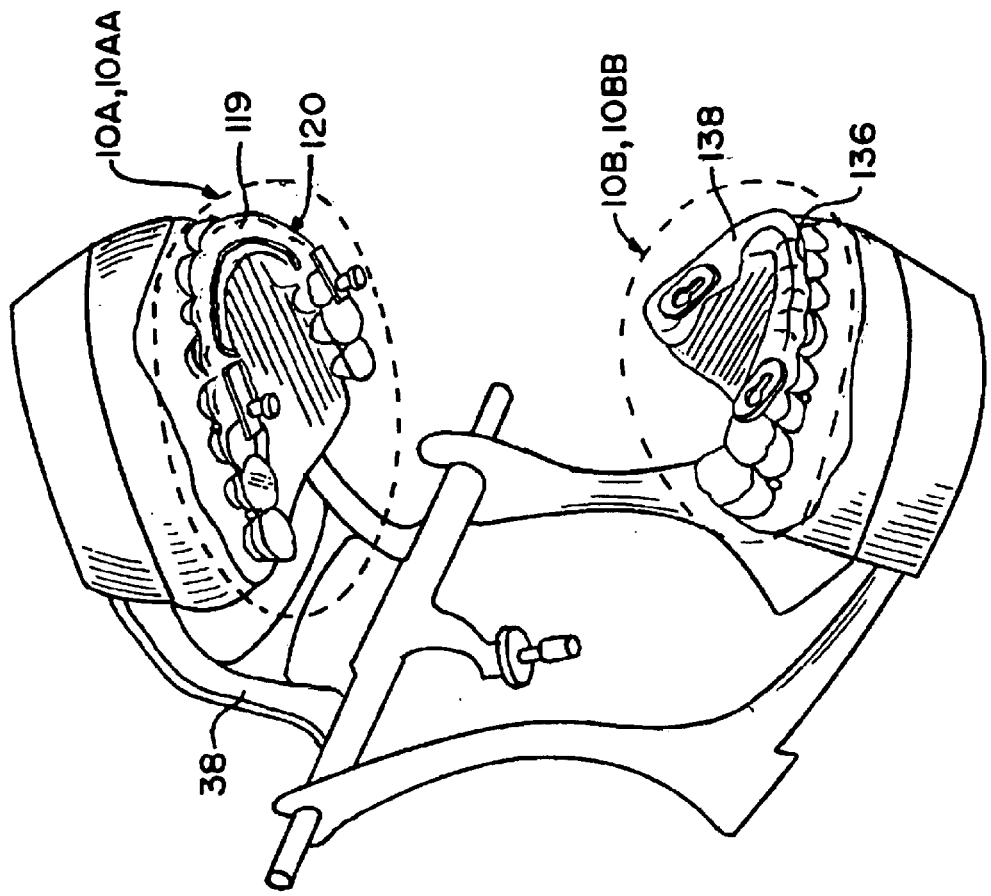
FIG. 9
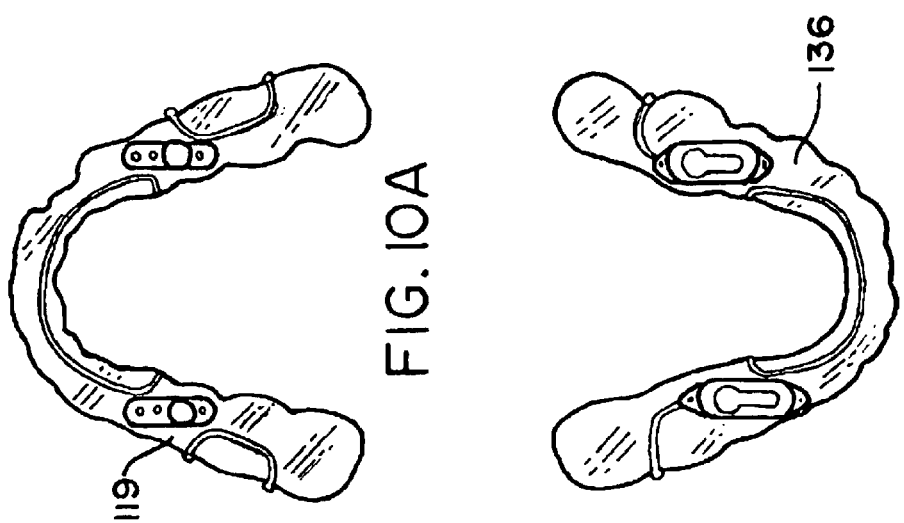
FIG. 10A
FIG. 10B

FIG 12-A
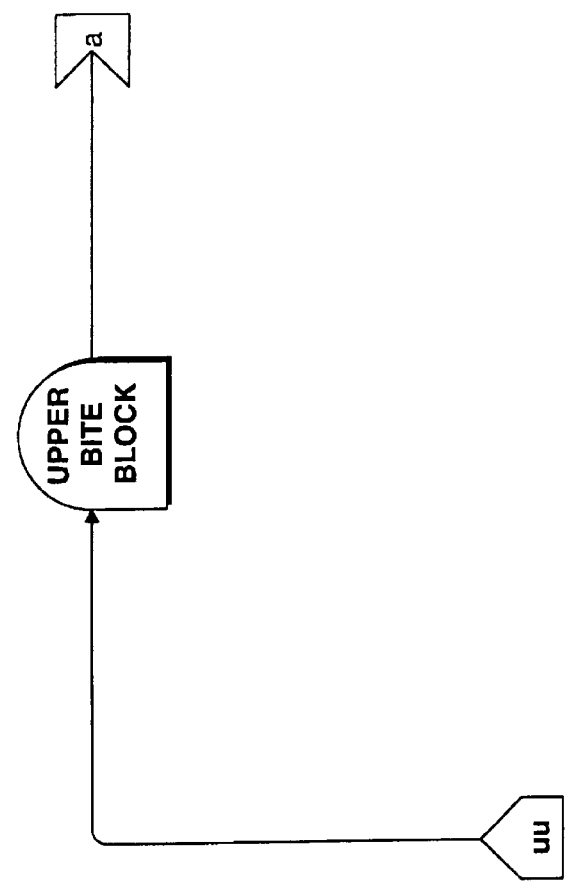

FIG 12-B
STEP 17
MAKE A DUPLICATE OF AN ORIGINAL UPPER CASTING (56), FORMING AN UPPER DUPLICATE CASTING (58), WHEREIN THE ORIGINAL UPPER CASTING (56) HAS A GUM (60), TEETH (62) WITH SUPRA BULGES (64) AND POSTERIOR PORTIONS (66) WITH BITE SURFACES (68), AND WHEREIN THE UPPER DUPLICATE CASTING (58) HAS TEETH (70)

FIG 12-C

FIG 12-D
STEP 19
EXTEND THE SURVEYING LINE (72) APPROXIMATELY 1 MM PAST THE SUPRA BULGES (64) OF THE TEETH (62) OF THE ORIGINAL UPPER CASTING (56), TOWARD THE GUM (60) OF THE ORIGINAL UPPER CASTING (56), FORMING AN EXTENDED SURVEYING LINE (74)

FIG 12-E
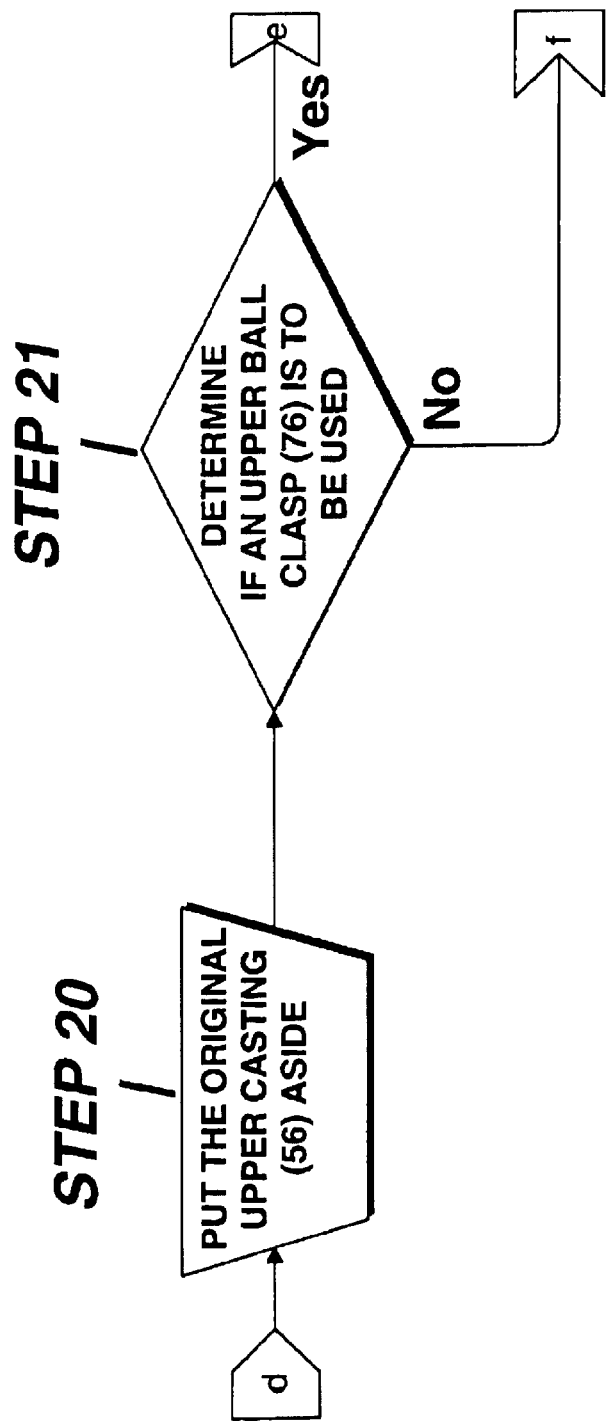

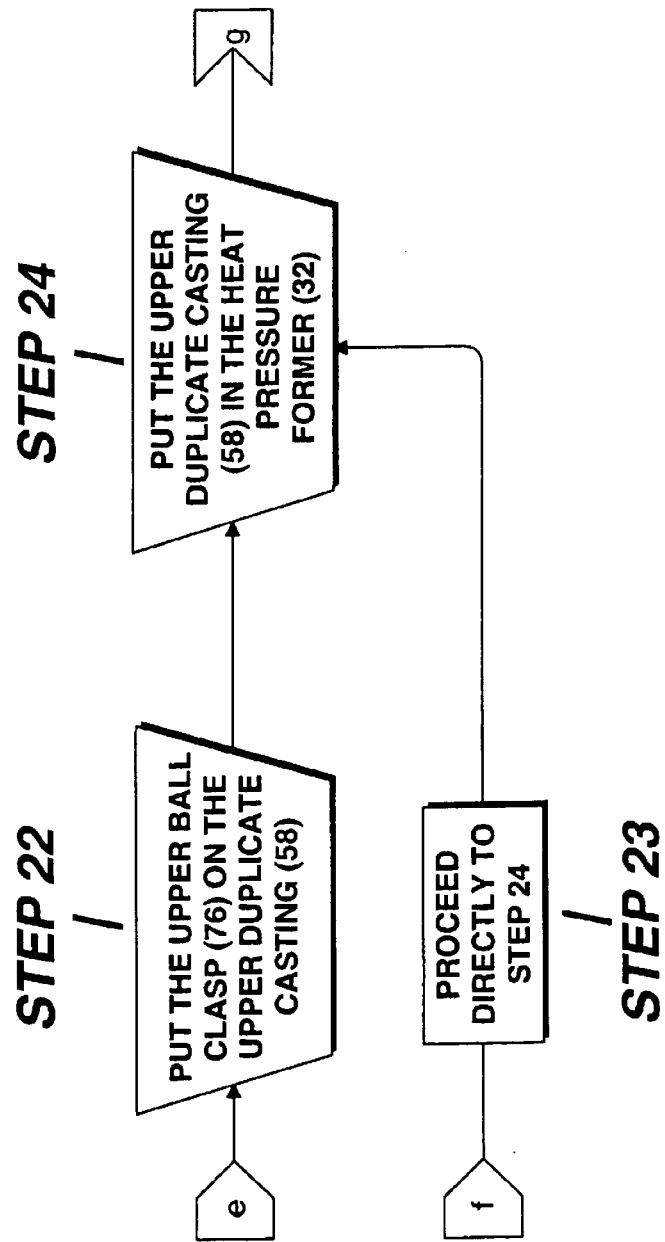

FIG 12-G
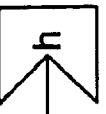
STEP 25
POSITION ANOTHER AT LEAST ONE PLASTIC SPACER SHEET (34) ON THE TEETH (70) OF THE UPPER DUPLICATE CASTING (58)

FIG 12-H

STEP 26

ACTIVATE THE HEAT PRESSURE FORMER (32), CAUSING THE ANOTHER AT LEAST ONE PLASTIC SPACER SHEET (34) TO MELT AND CONFORM TO THE TEETH (70) OF THE UPPER DUPLICATE CASTING (58), FORMING A CONFORMED PLASTIC SPACER LAYER (82) THEREON

FIG 12-I
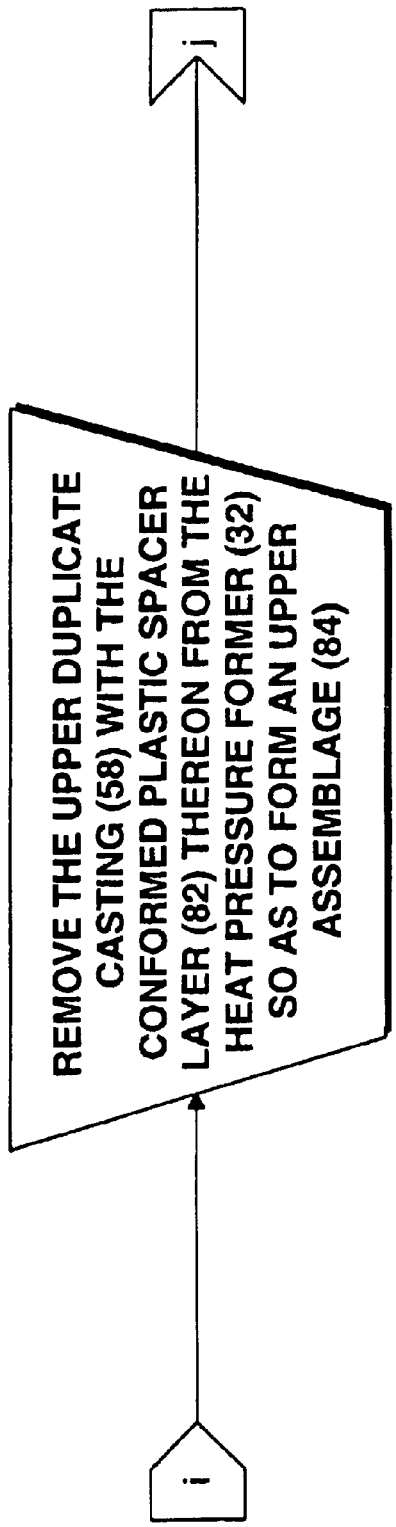
STEP 27
REMOVE THE UPPER DUPLICATE CASTING (58) WITH THE CONFORMED PLASTIC SPACER LAYER (82) THEREON FROM THE HEAT PRESSURE FORMER (32) SO AS TO FORM AN UPPER ASSEMBLAGE (84)

FIG 12-J
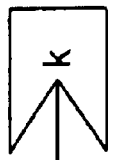
STEP 28
PLACE THE UPPER ASSEMBLAGE (84) ON THE ARTICULATOR (38)

FIG 12-K

FIG 12-L

FIG 12-M

FIG 12-N

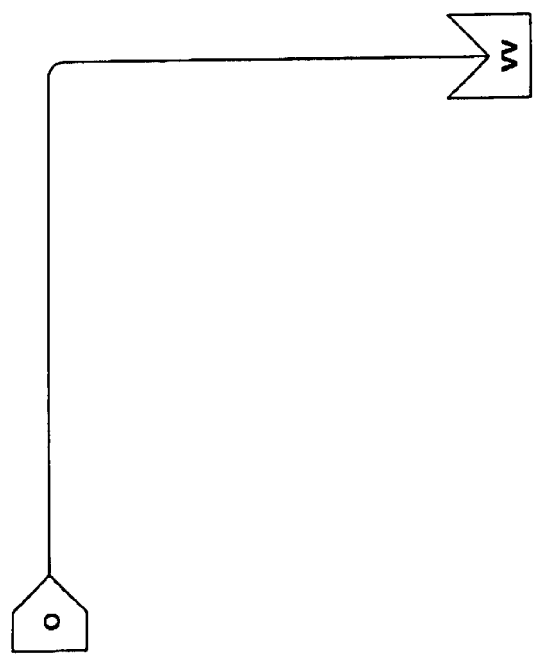
FIG 12-O

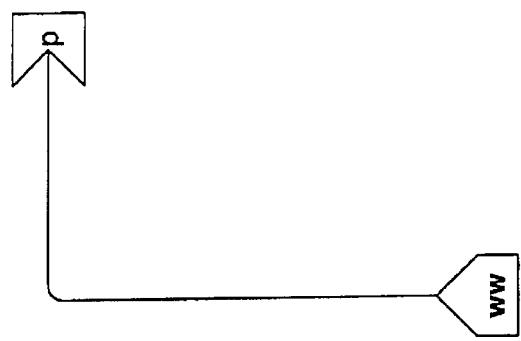
FIG 12-P

FIG 12-Q
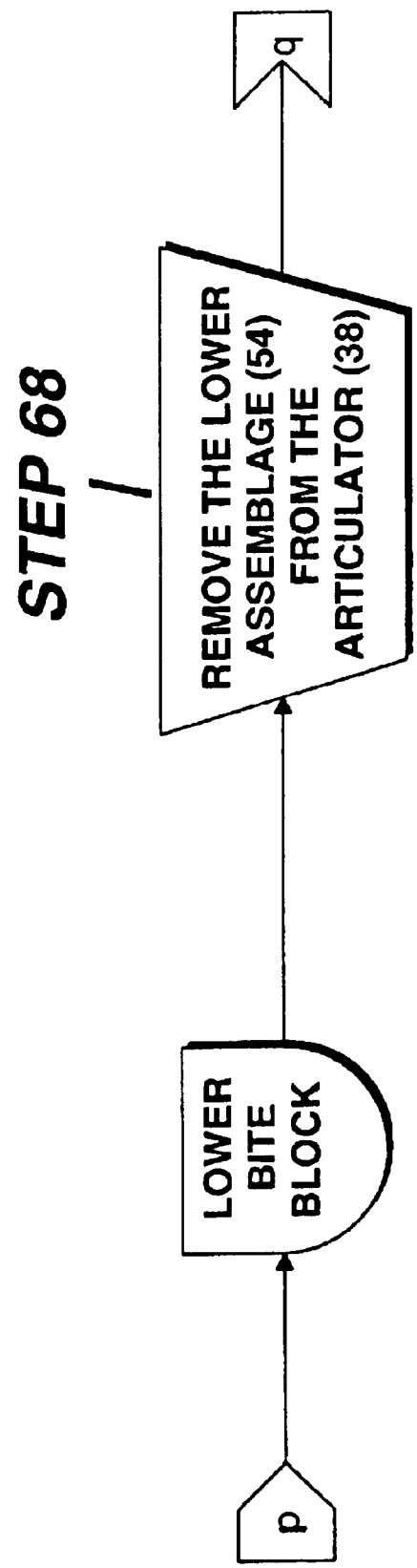

FIG 12-R
STEP 69 — TACK THE TEMPORARY STYLUS (122) TO EACH FEMALE HINGE PART (44) WITH THE WAX LUTING AGENT (46)

FIG 12-S
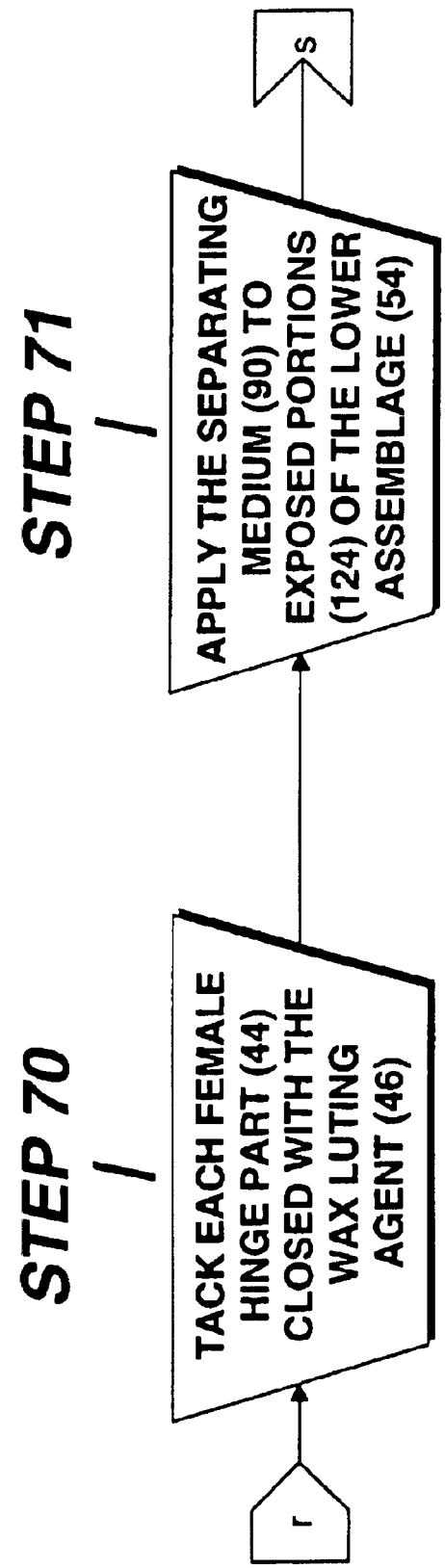

FIG 12-T
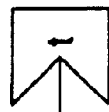
STEP 72
POSITION THE STONE (94) IN THE LOWER PORTION (96) OF THE FLASK (98)
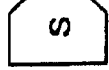

FIG 12-U
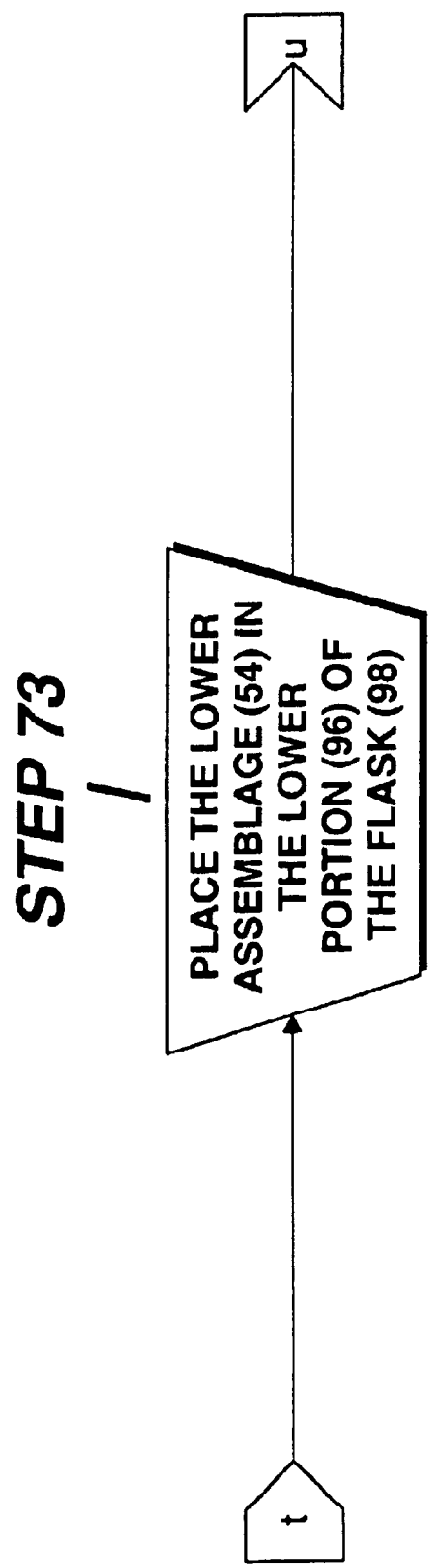

FIG 12-V
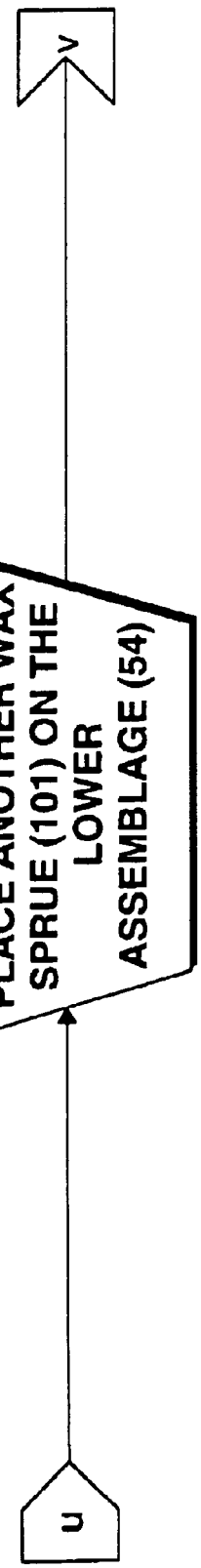

FIG 12-W
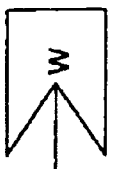
STEP 75
APPLY THE SEPARATING MEDIUM (90) TO THE STONE (94) THAT IS EXPOSED AND TO THE LOWER ASSEMBLAGE (54)

FIG 12-X

FIG 12-Y
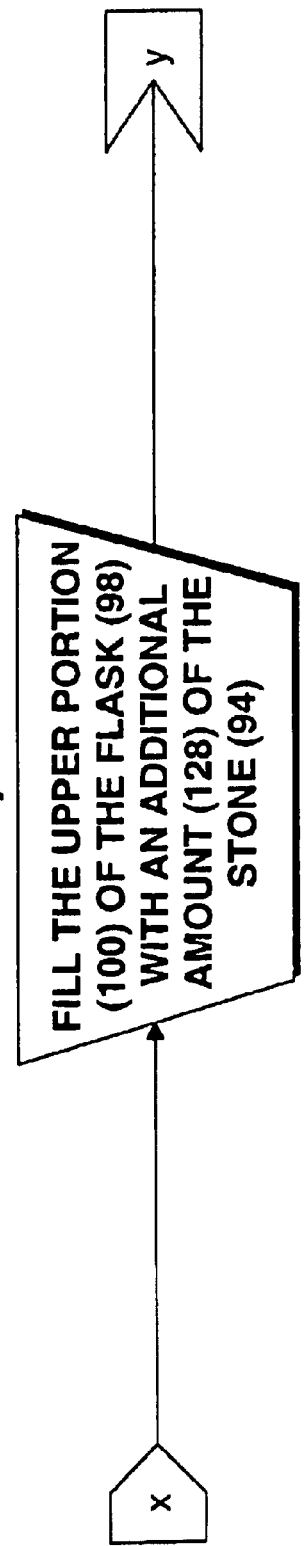
STEP 77
FILL THE UPPER PORTION (100) OF THE FLASK (98) WITH AN ADDITIONAL AMOUNT (128) OF THE STONE (94)

FIG 12-Z

FIG 12-AA
STEP 79
REMOVE THE WAX LUTING AGENT (46) AND THE ANOTHER WAX SPRUE (101) FROM THE LOWER BITE BLOCK MOLD (130), UTILIZING THE BOILING WATER (108), WITH THE LOWER BALL CLASP (30), THE LOWER U-SHAPED REINFORCING WIRE (88), AND THE FEMALE HINGE PART (44) RETAINED IN THE LOWER BITE BLOCK MOLD (130)

FIG 12-BB

STEP 80 — SEPARATE THE UPPER PORTION (100) OF THE FLASK (98) FROM THE LOWER PORTION (96) OF THE FLASK (98)

aa → STEP 80 → bb

FIG 12-CC
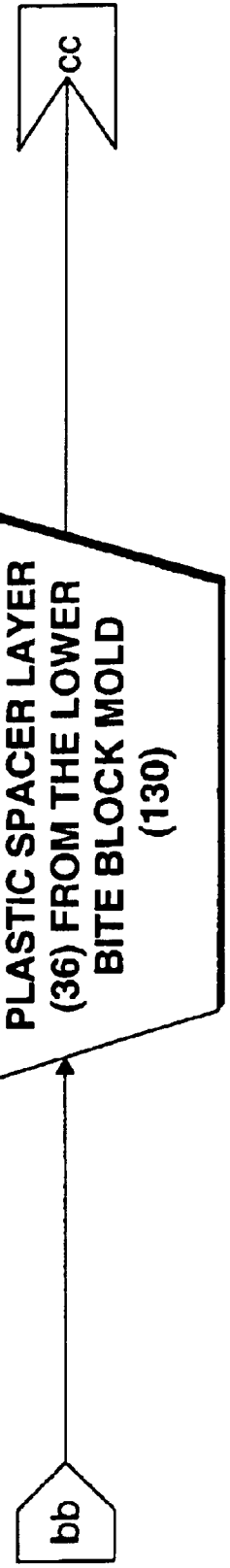

FIG 12-DD
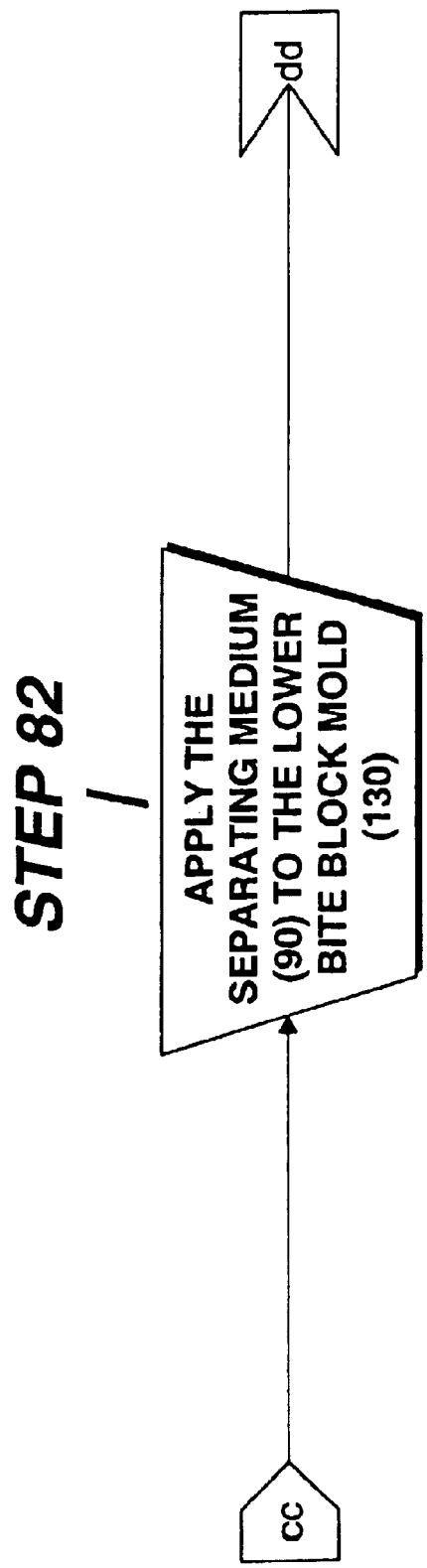

FIG 12-EE
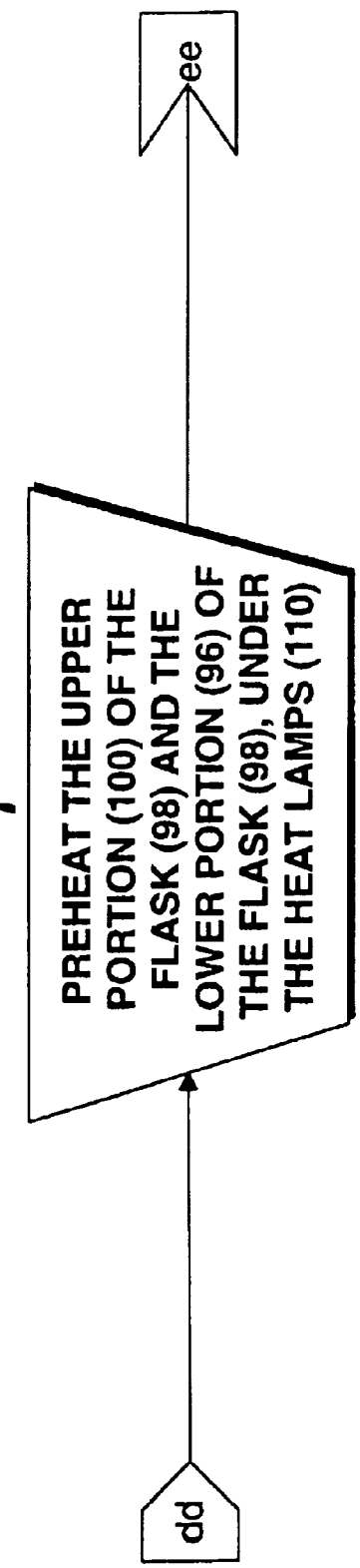

FIG 12-FF
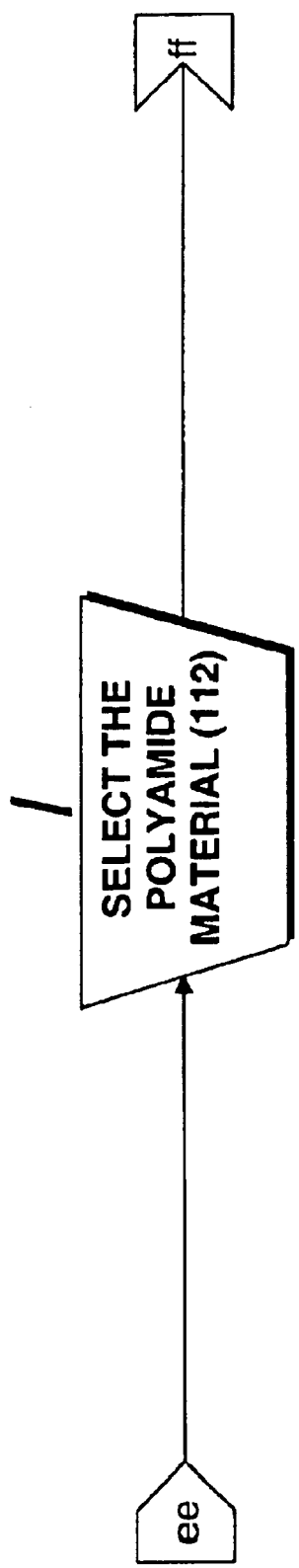

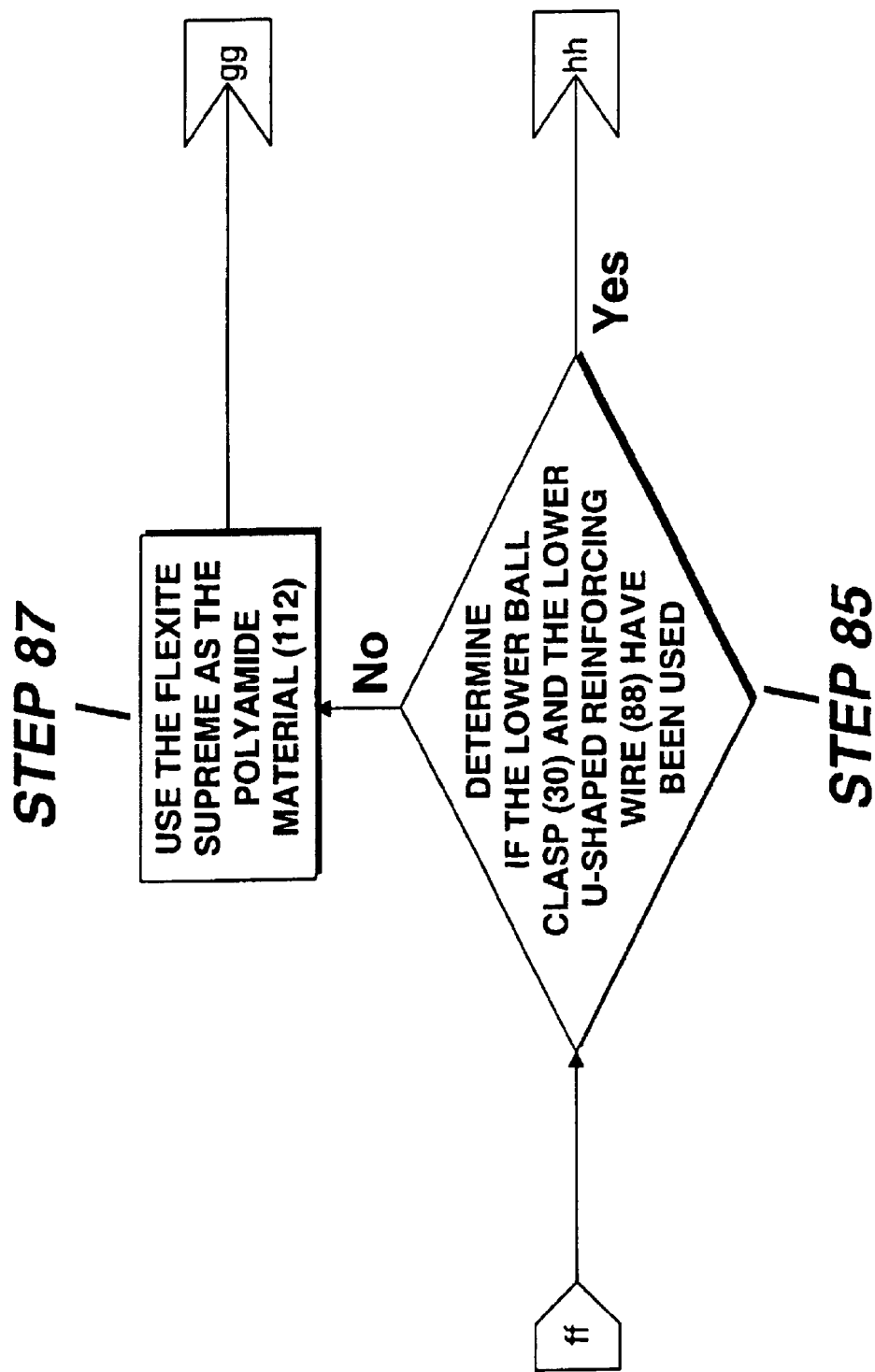

FIG 12-HH
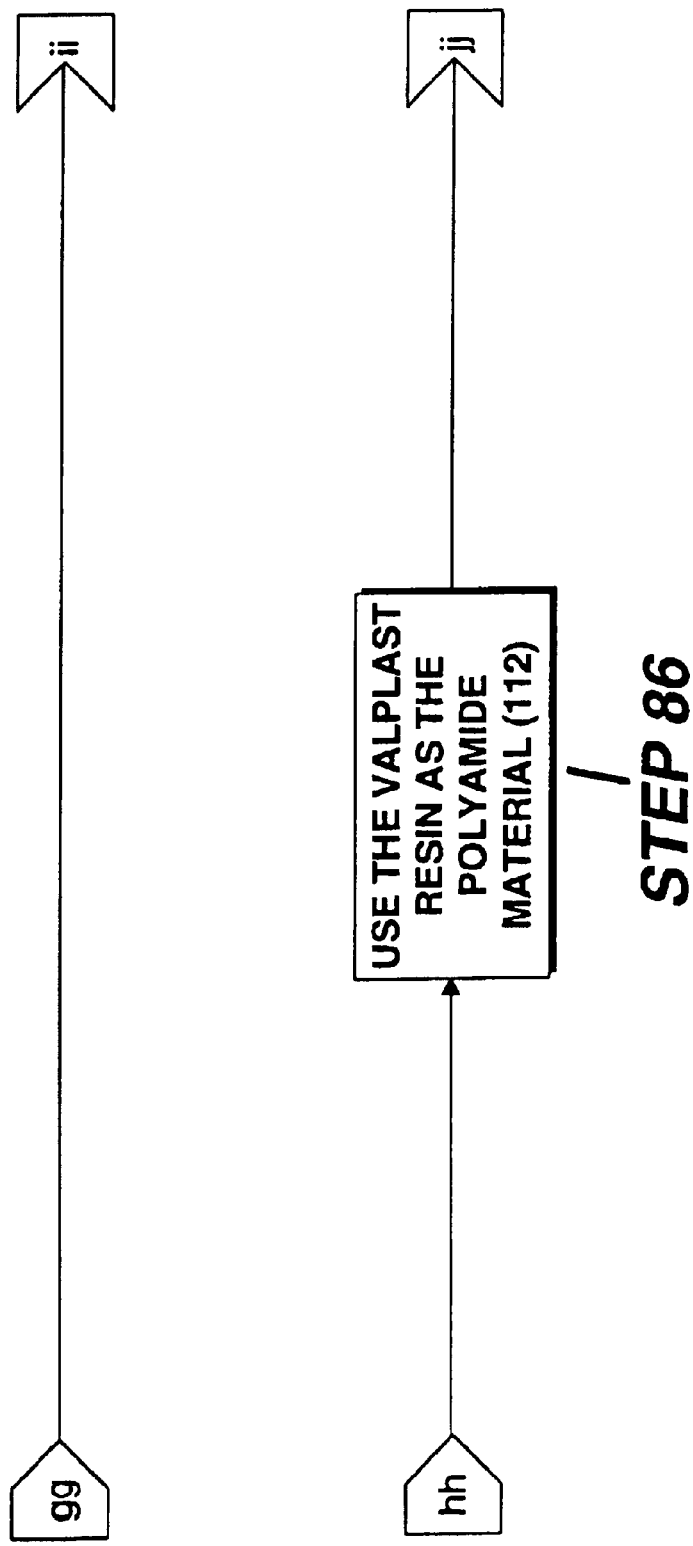

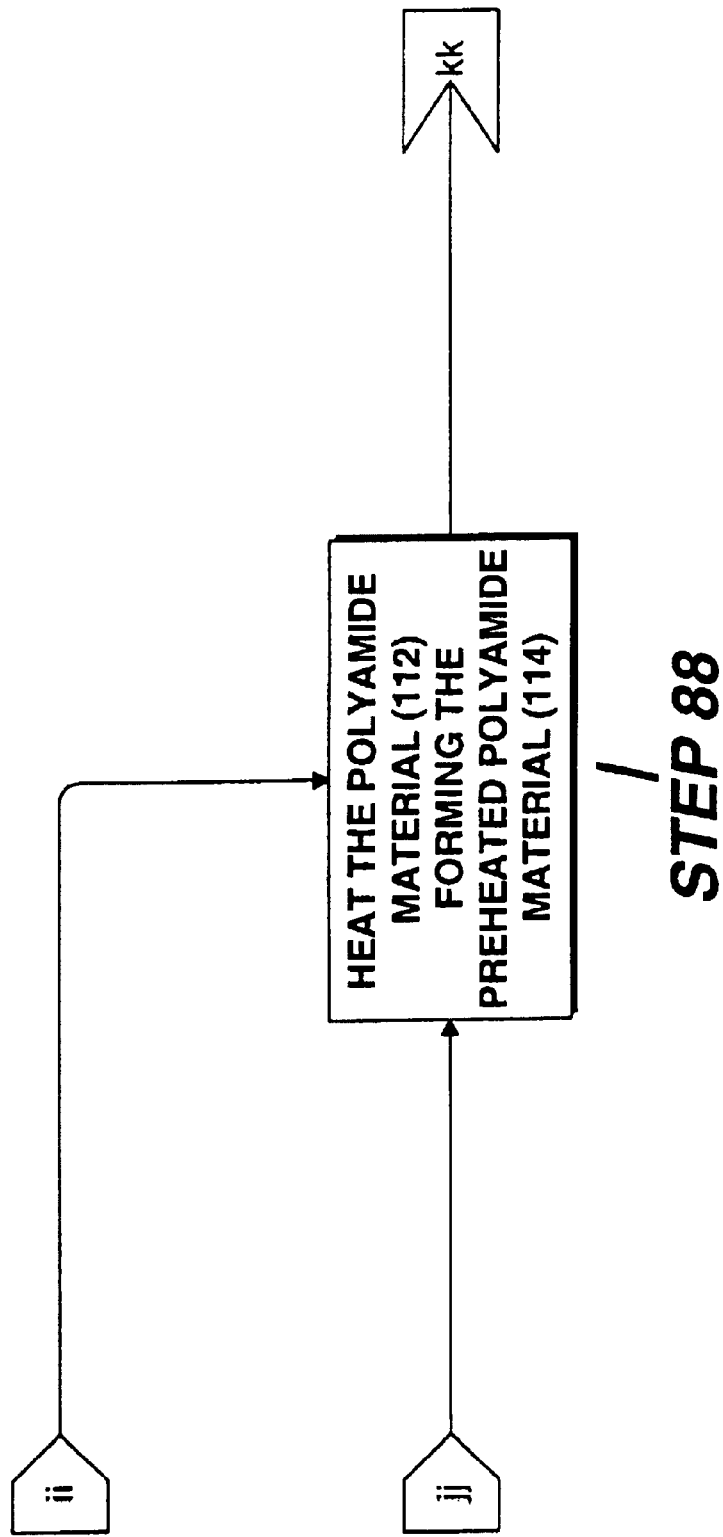

FIG 12-JJ
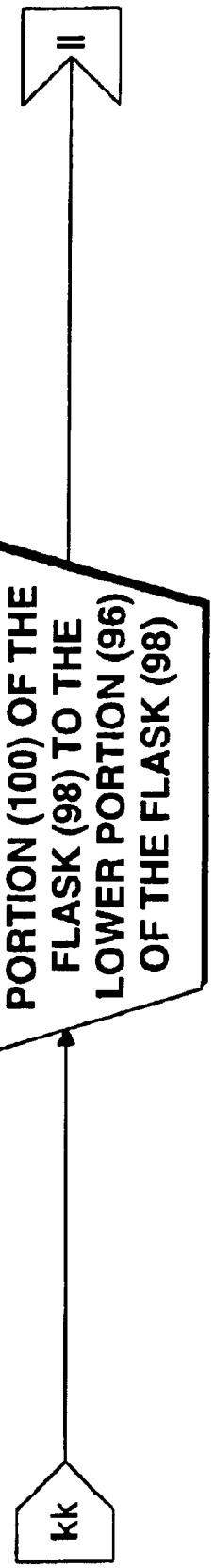

FIG 12-KK
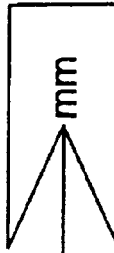
STEP 90
INJECT THE PREHEATED POLYAMIDE MATERIAL (114) INTO THE FLASK (98), FORMING A LOWER BITE BLOCK (132) HAVING THE LOWER BALL CLASP (30), THE LOWER U-SHAPED REINFORCING WIRE (88), AND THE FEMALE HINGE PART (44) EMBEDDED THEREIN
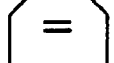

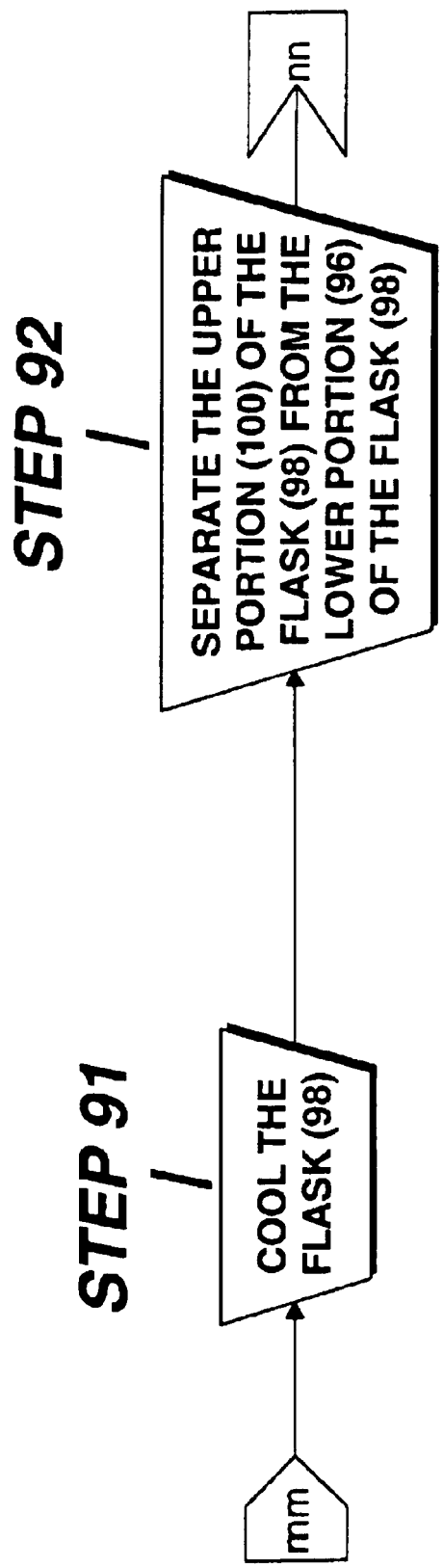
FIG 12-LL

FIG 12-MM
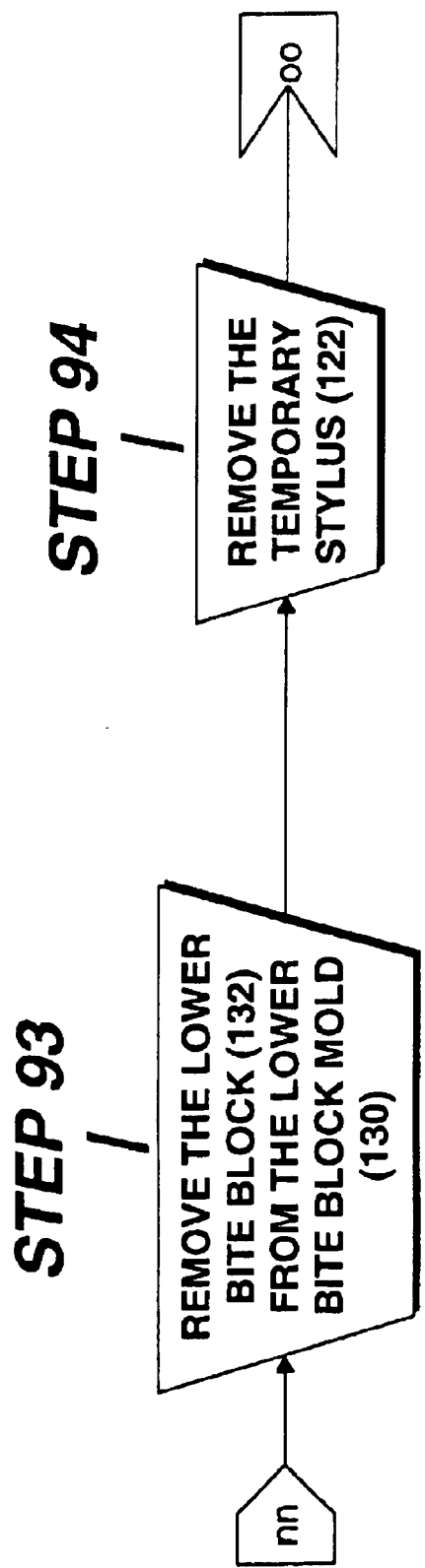

FIG 12-NN

STEP 95

REMOVE ALL ROUGH EDGES (134) FROM THE LOWER BITE BLOCK (132)

pp oo

FIG 12-OO

FIG 12-PP
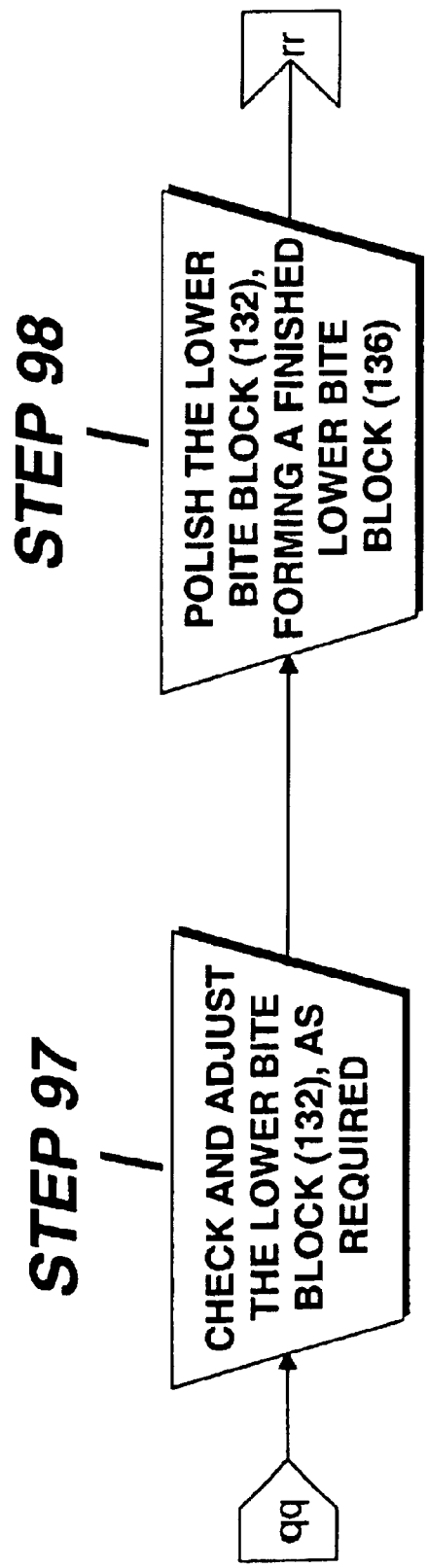

FIG 12-QQ
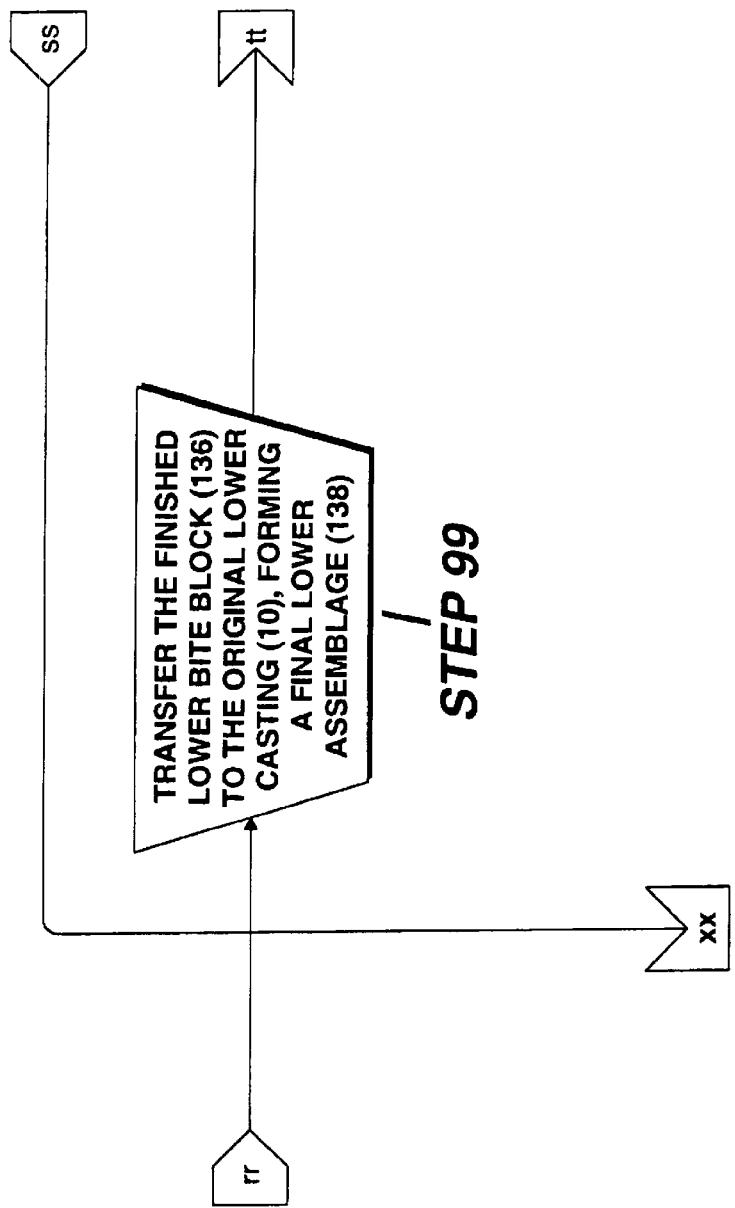

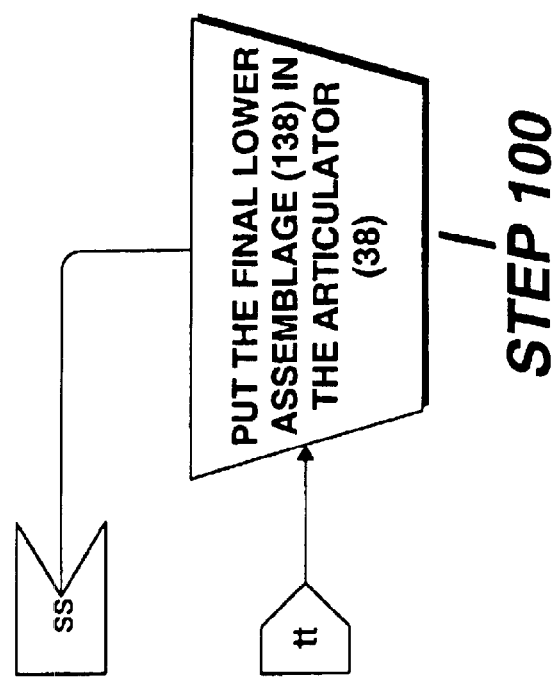

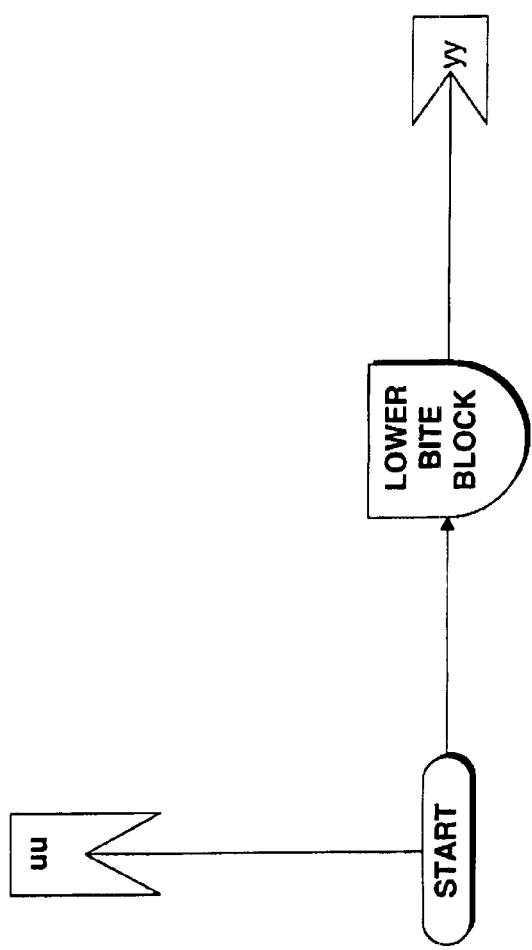
FIG 12-SS

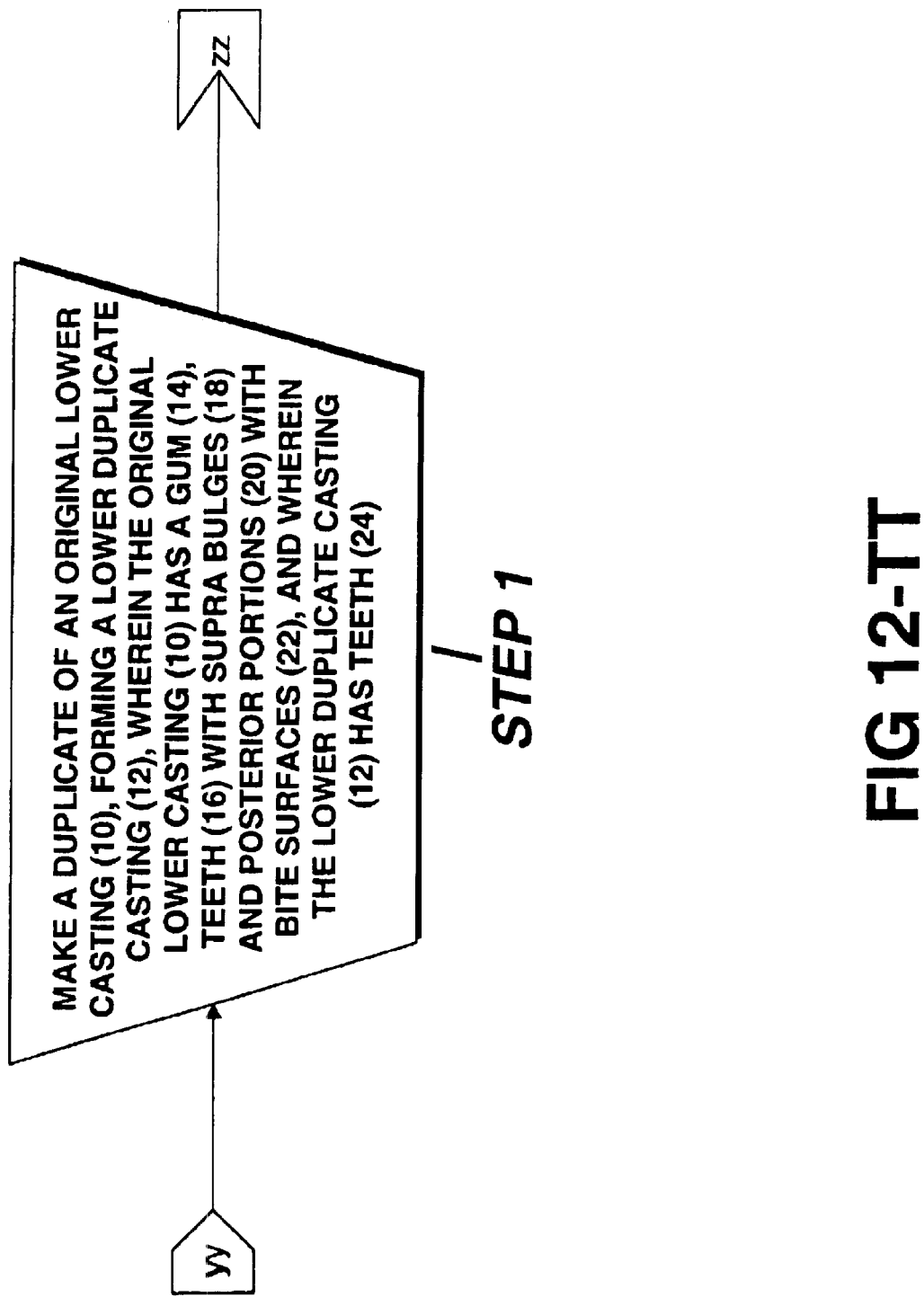
FIG 12-TT

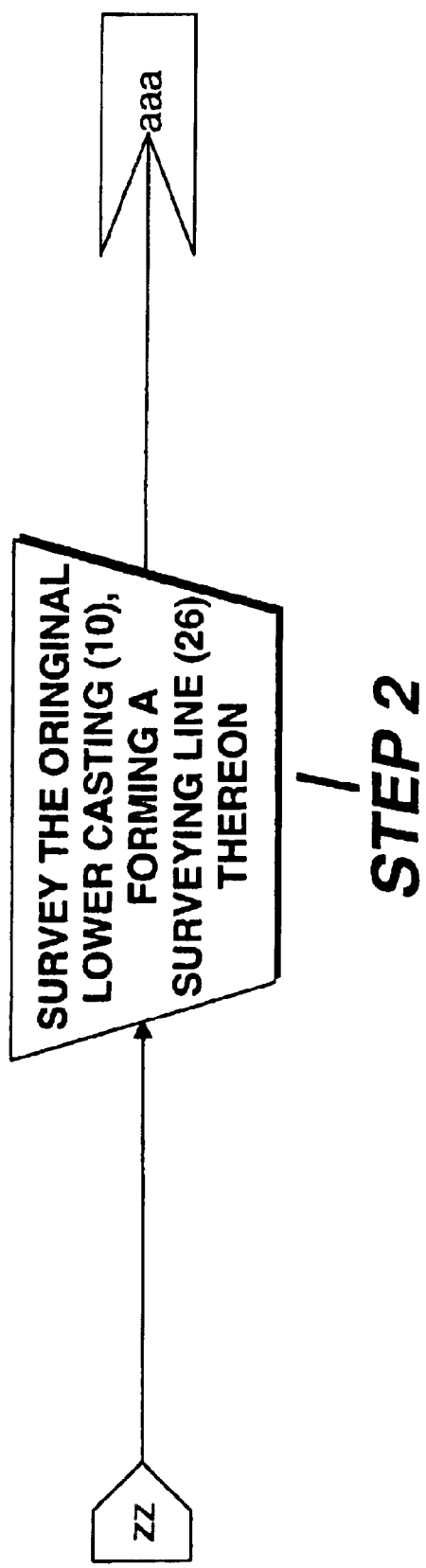
FIG 12-UU

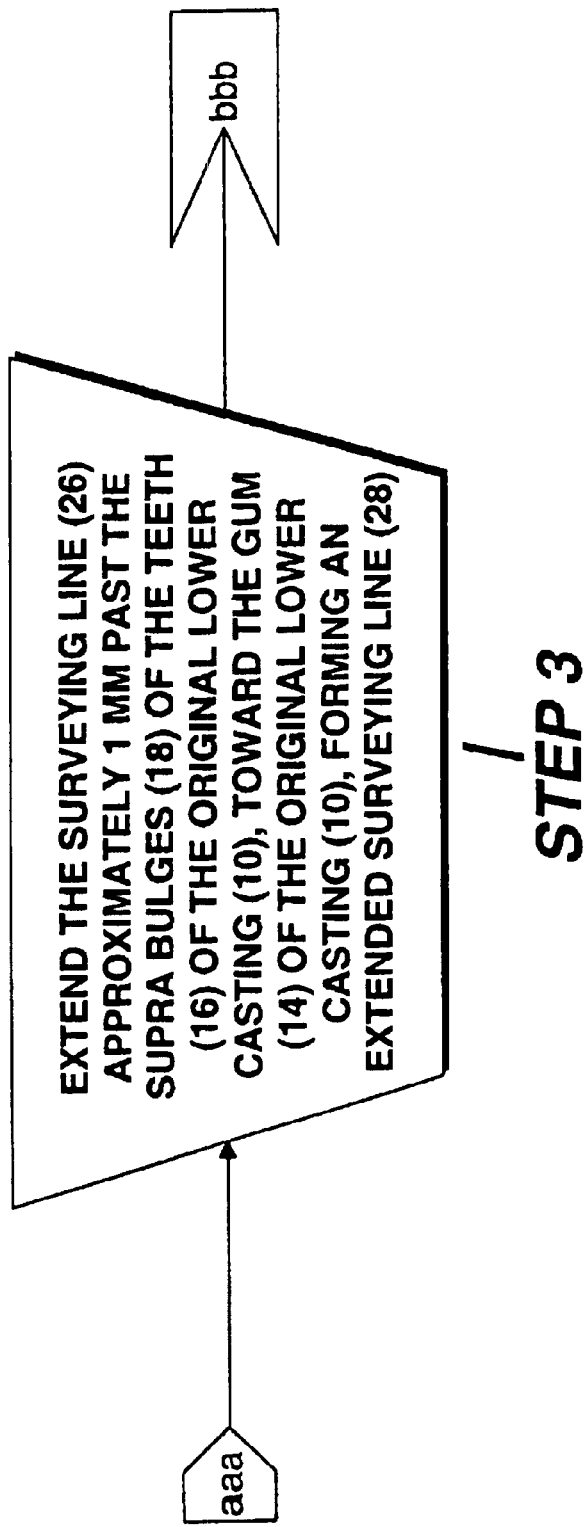
FIG 12-VV

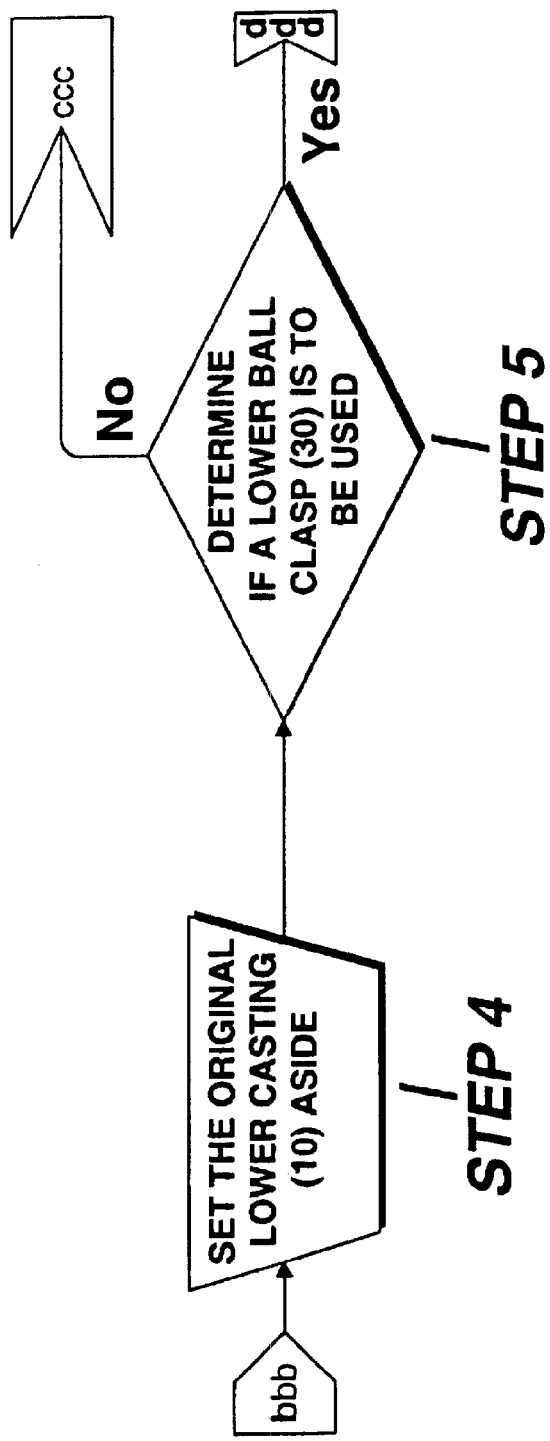
FIG 12-WW

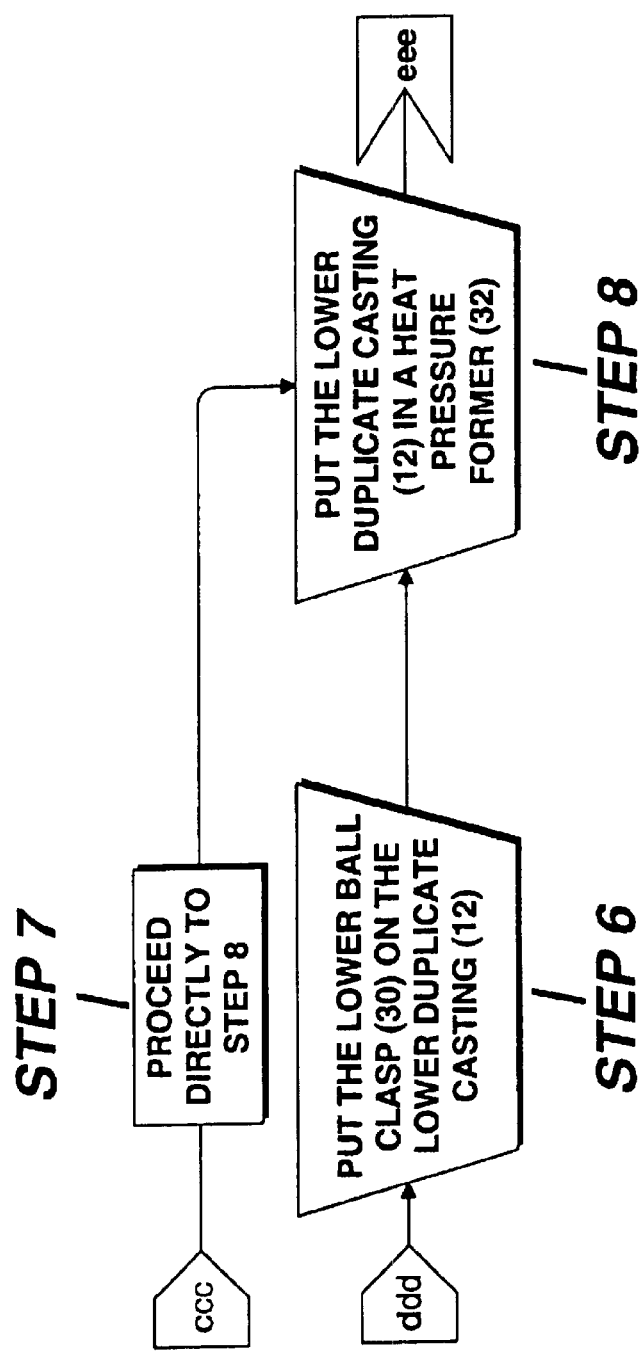
FIG 12-XX

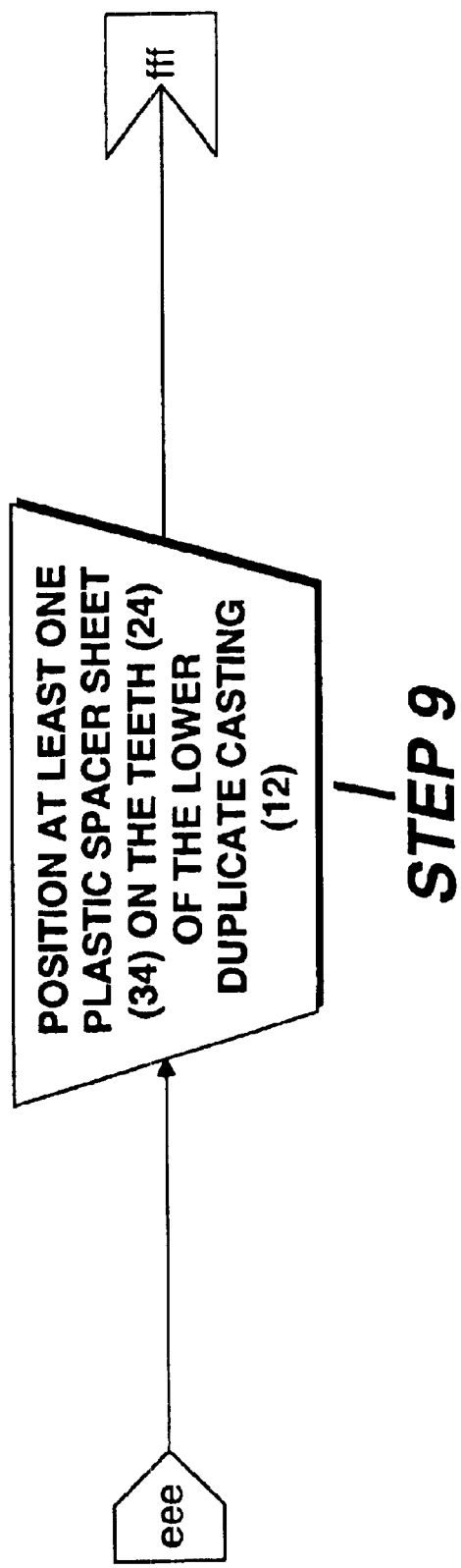
FIG 12-YY

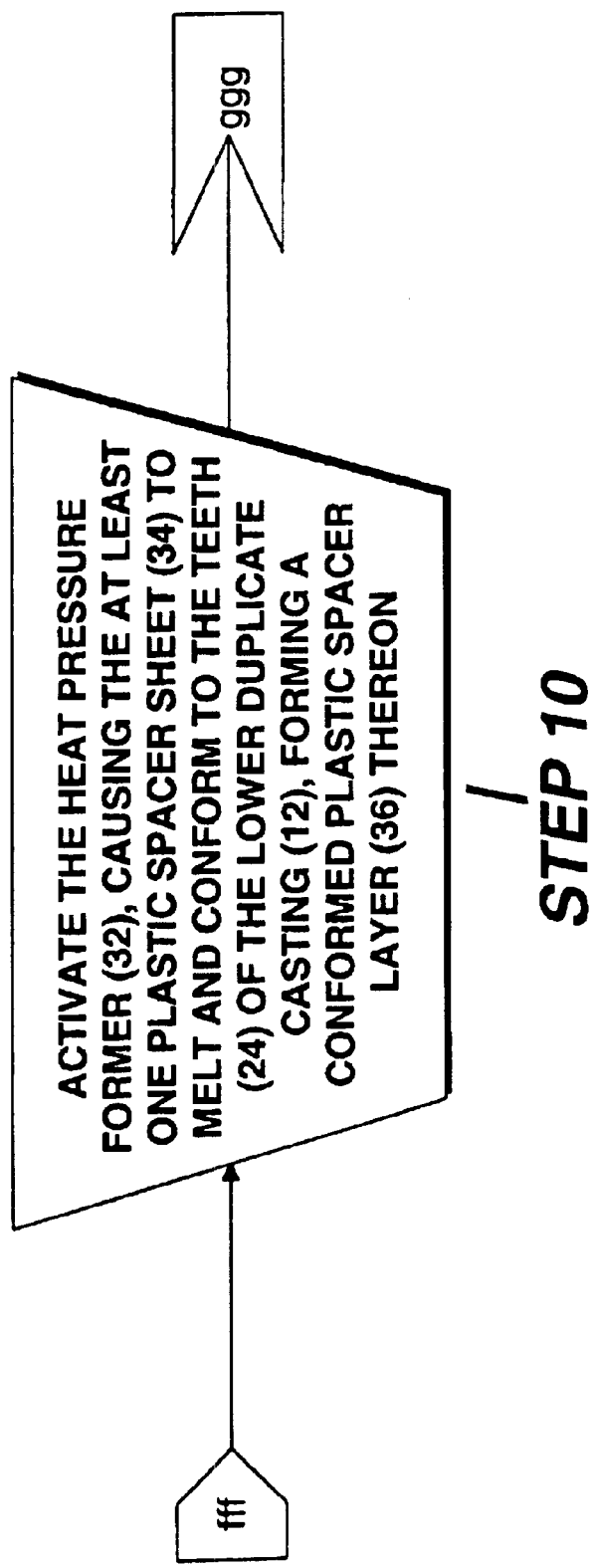
FIG 12-ZZ

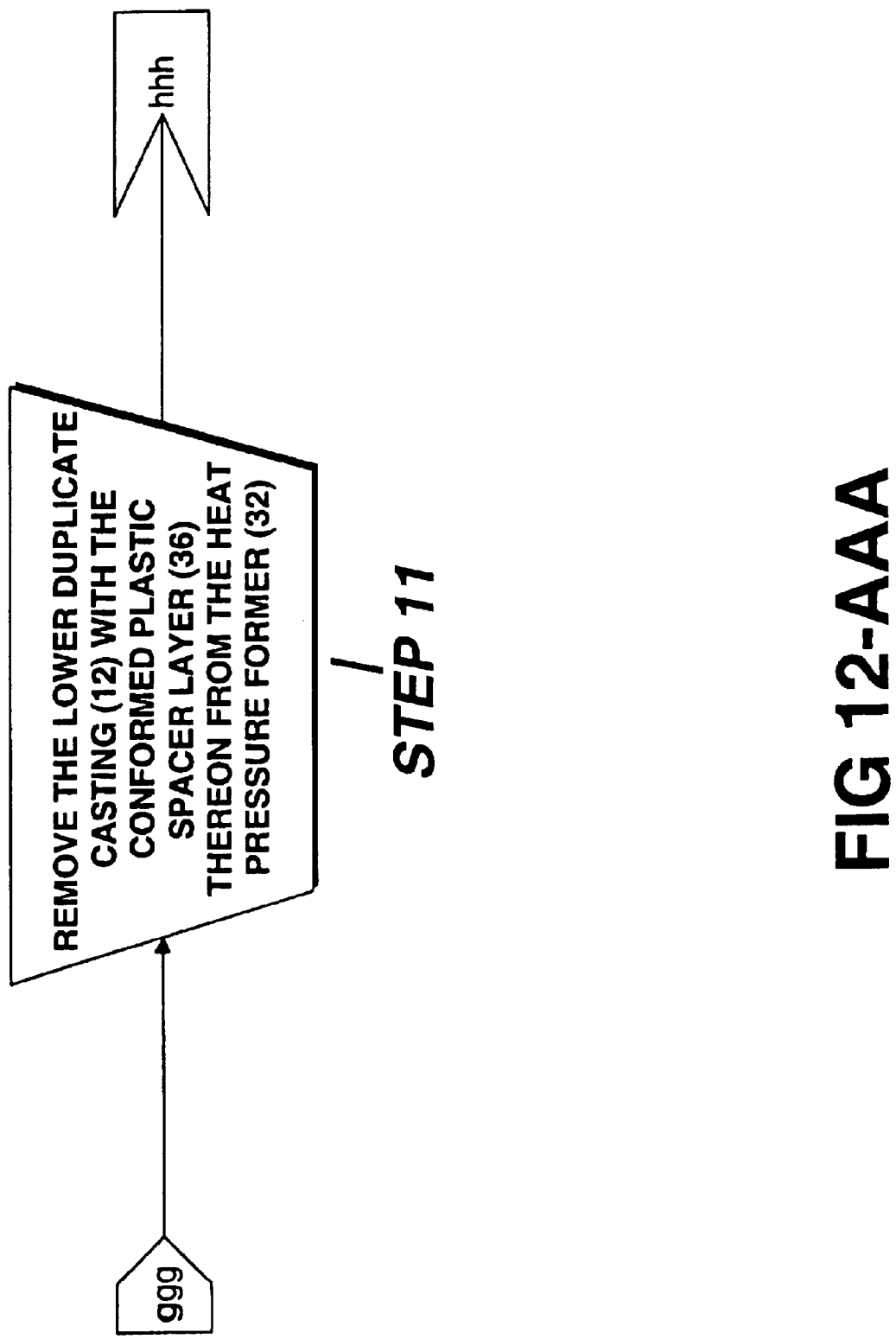
FIG 12-AAA

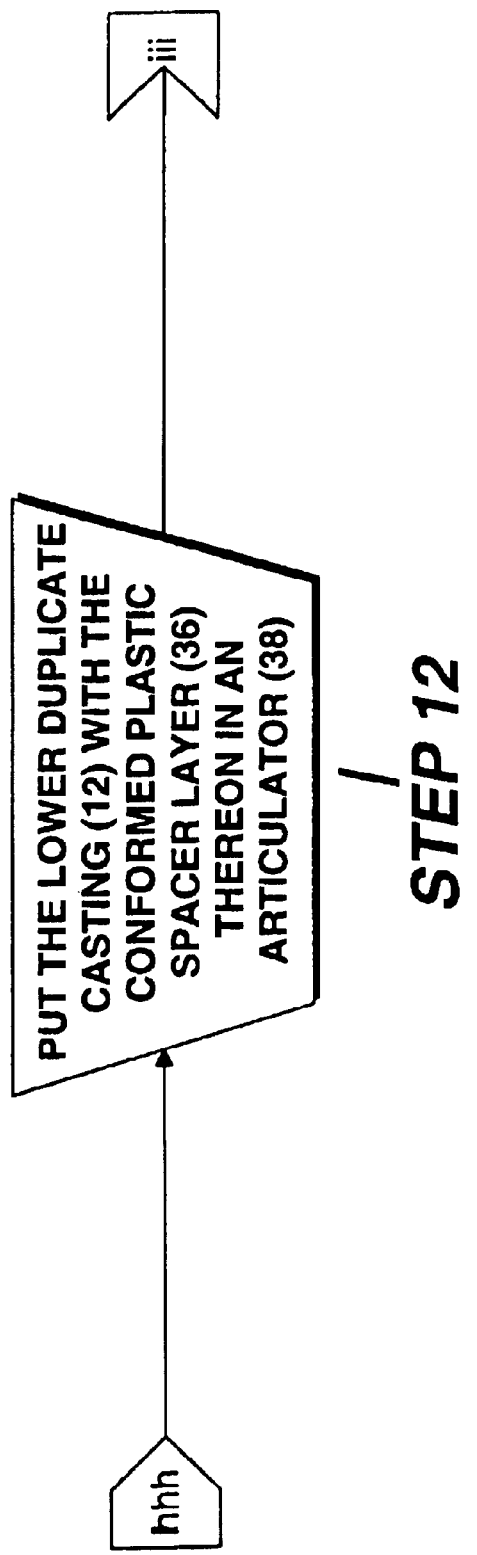
FIG 12-BBB

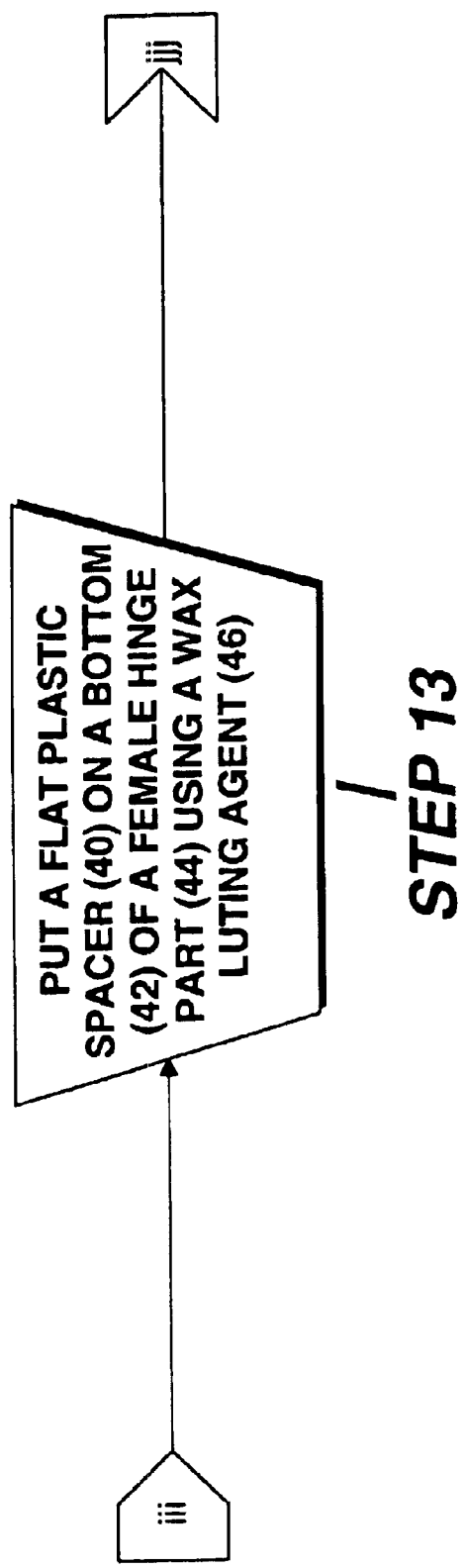
FIG 12-CCC

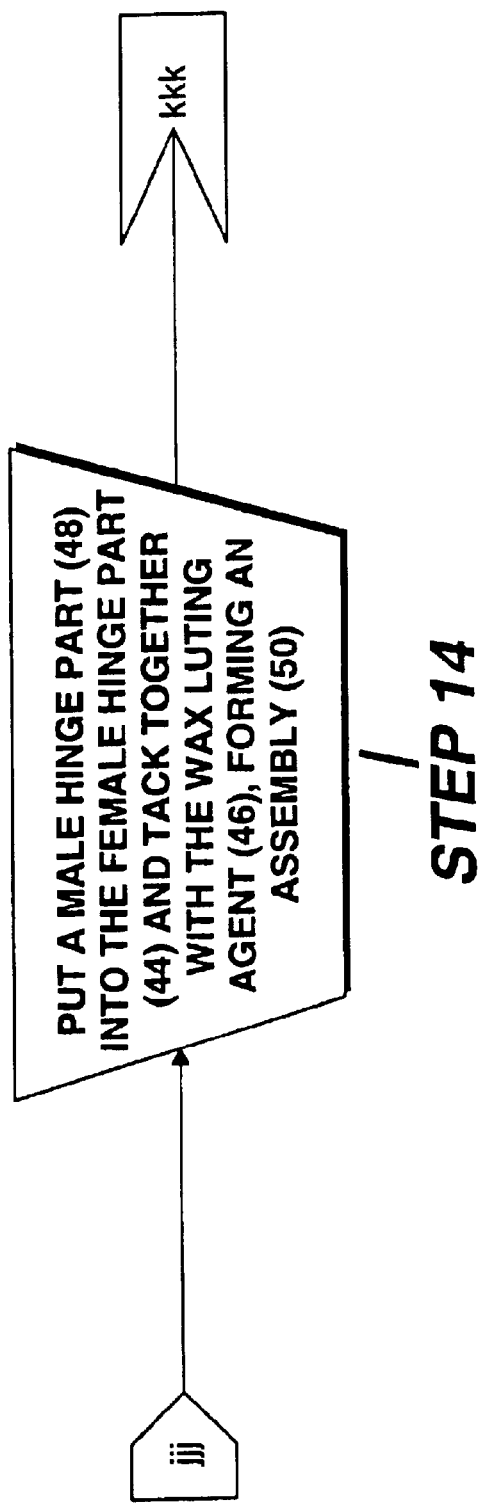
FIG 12-DDD

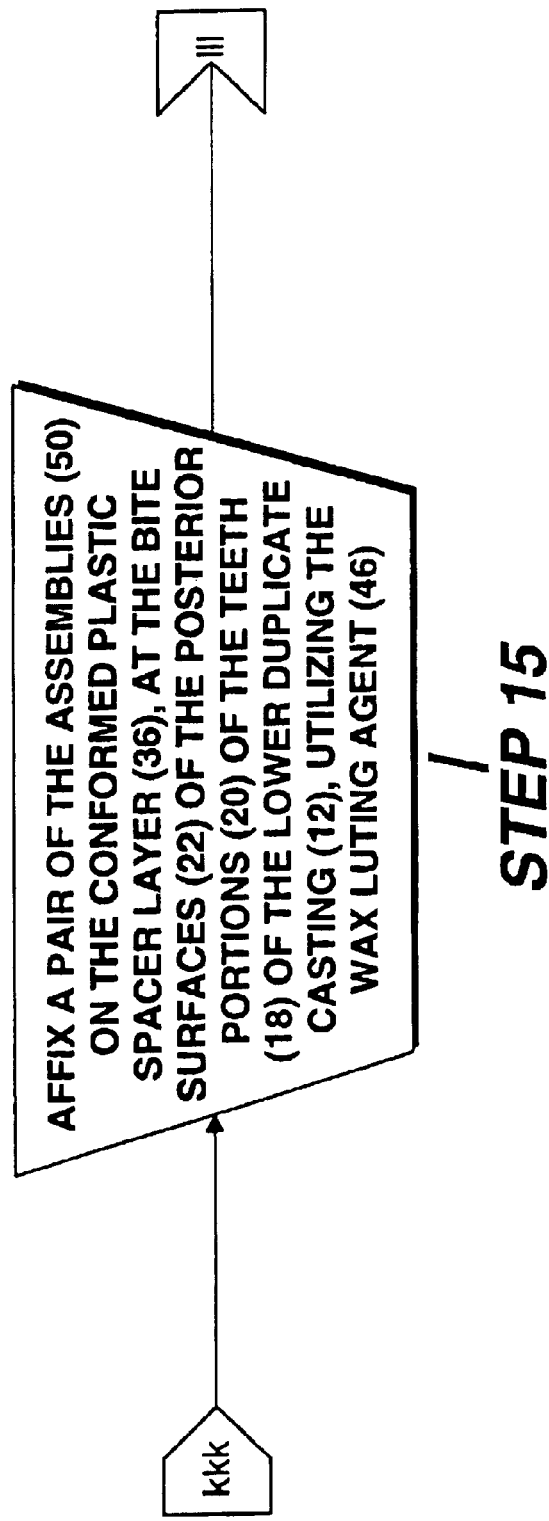
FIG 12-EEE

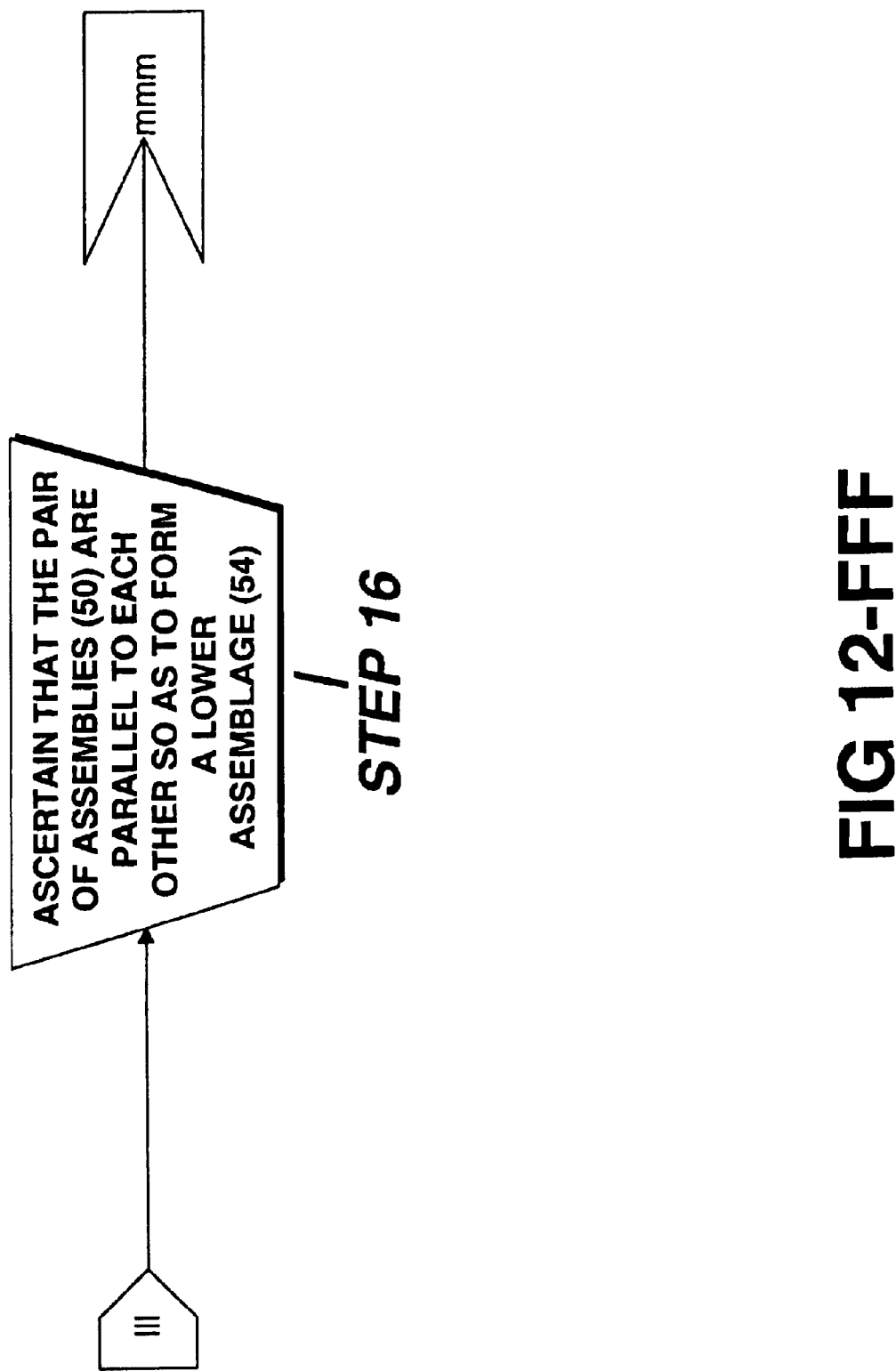
FIG 12-FFF

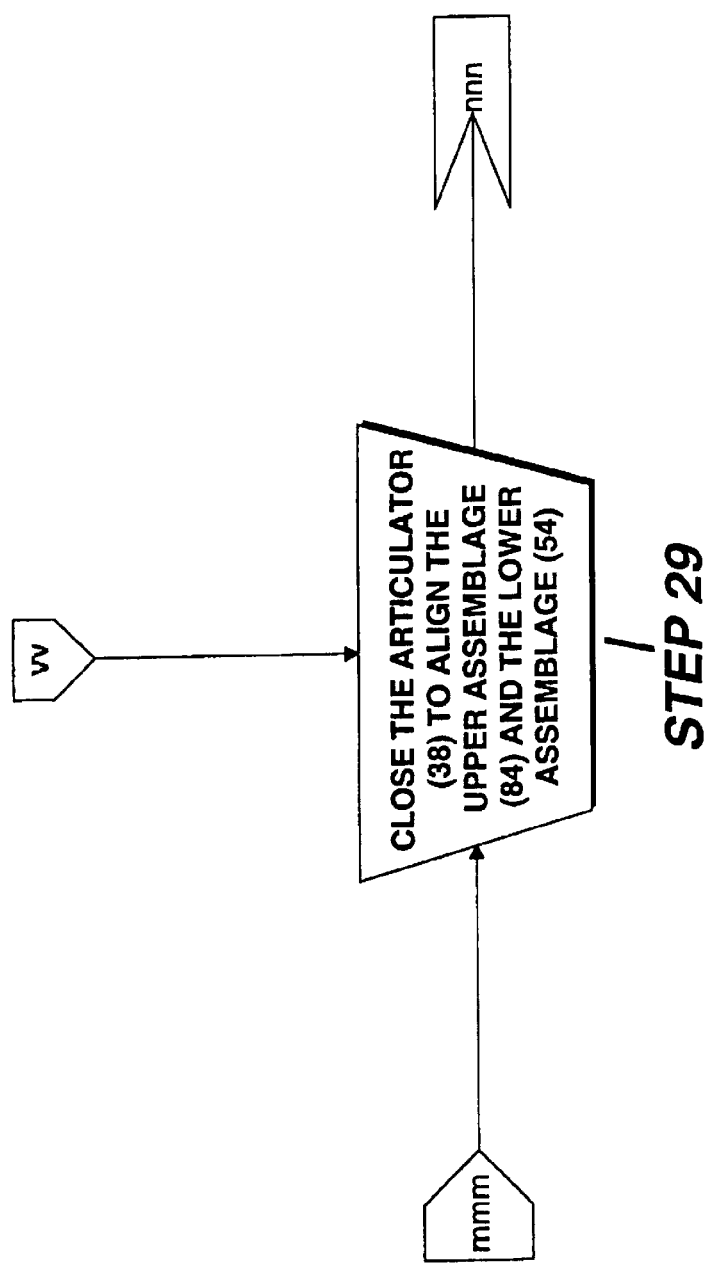
FIG 12-GGG

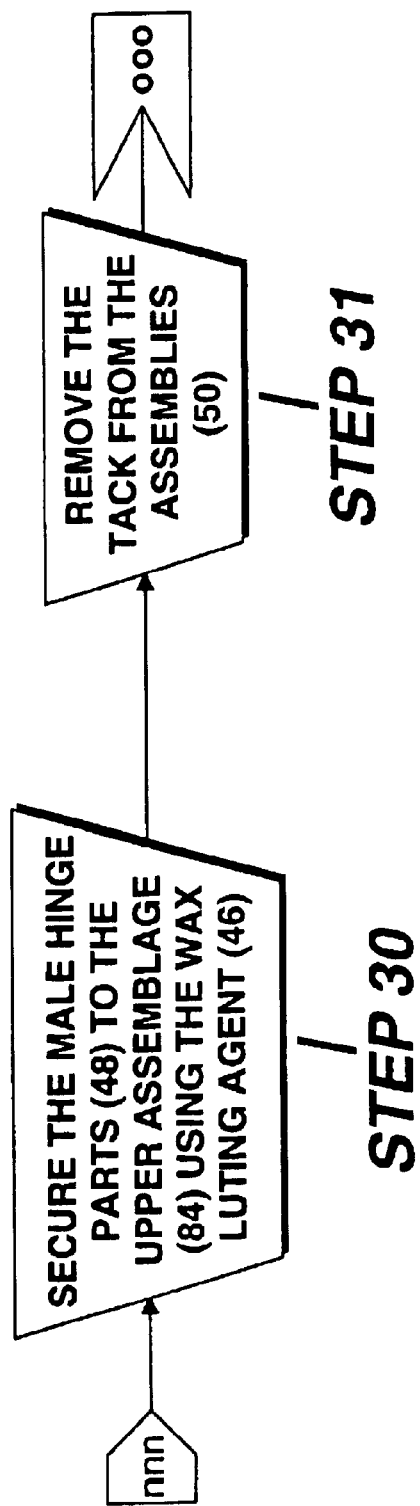
FIG 12-HHH

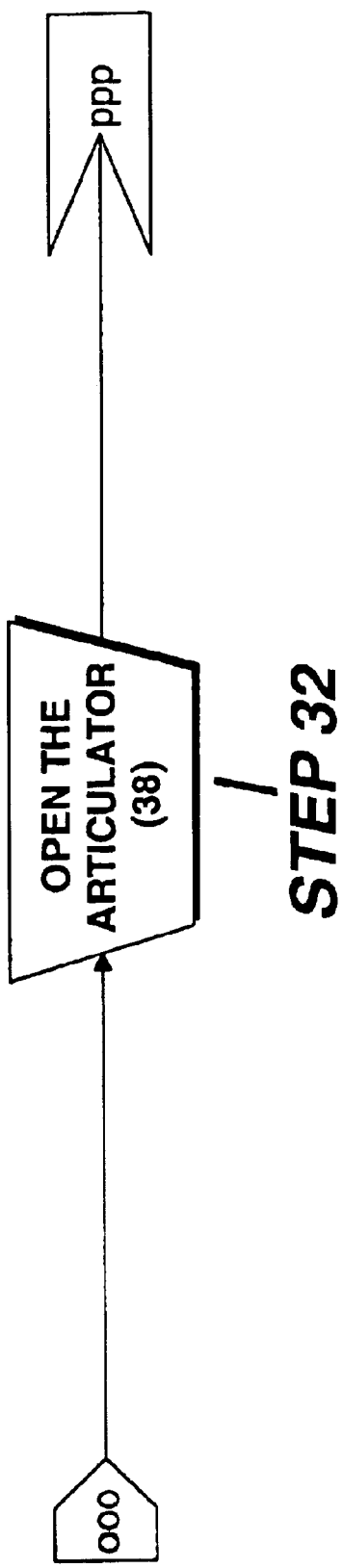
FIG 12-III

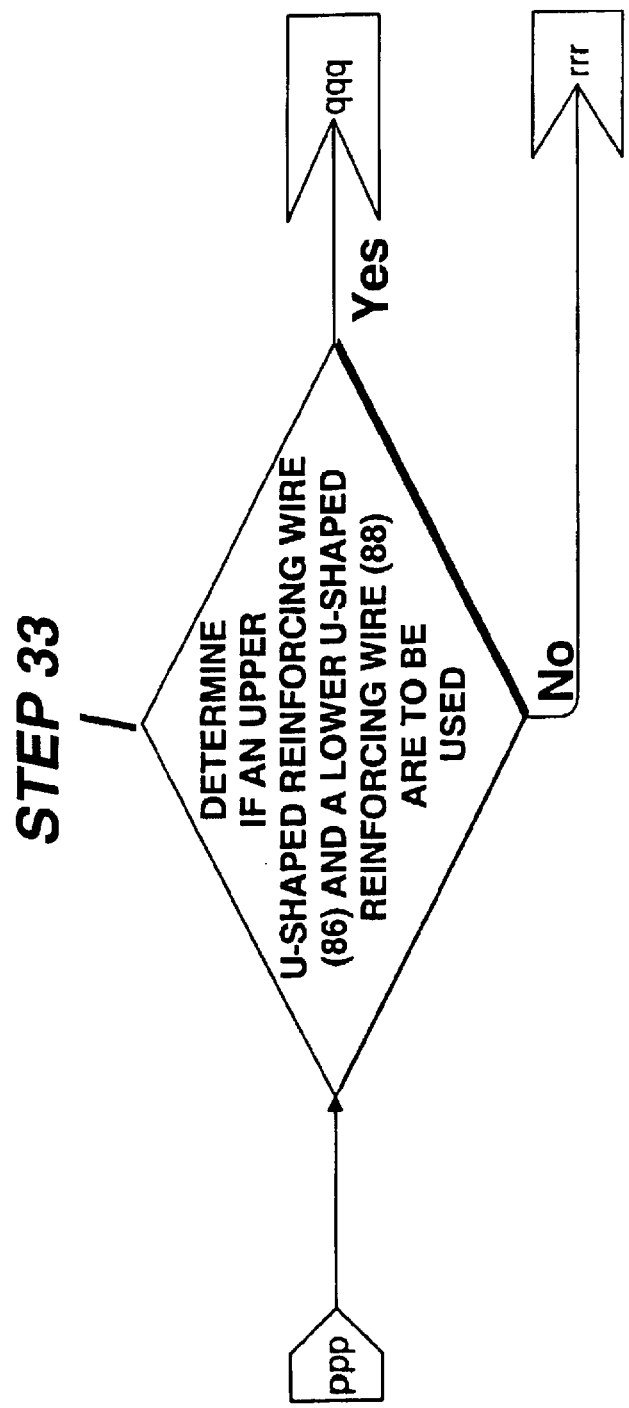
FIG 12-JJJ

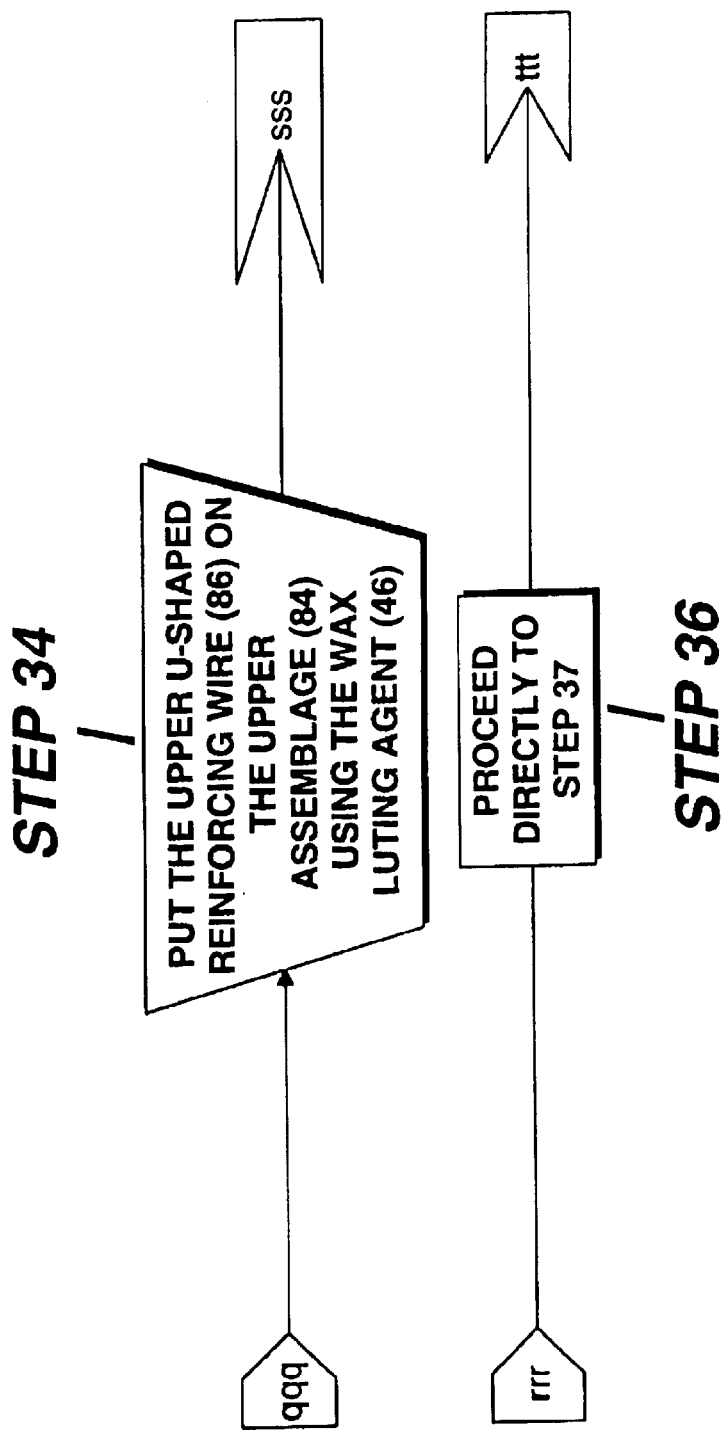
FIG 12-KKK

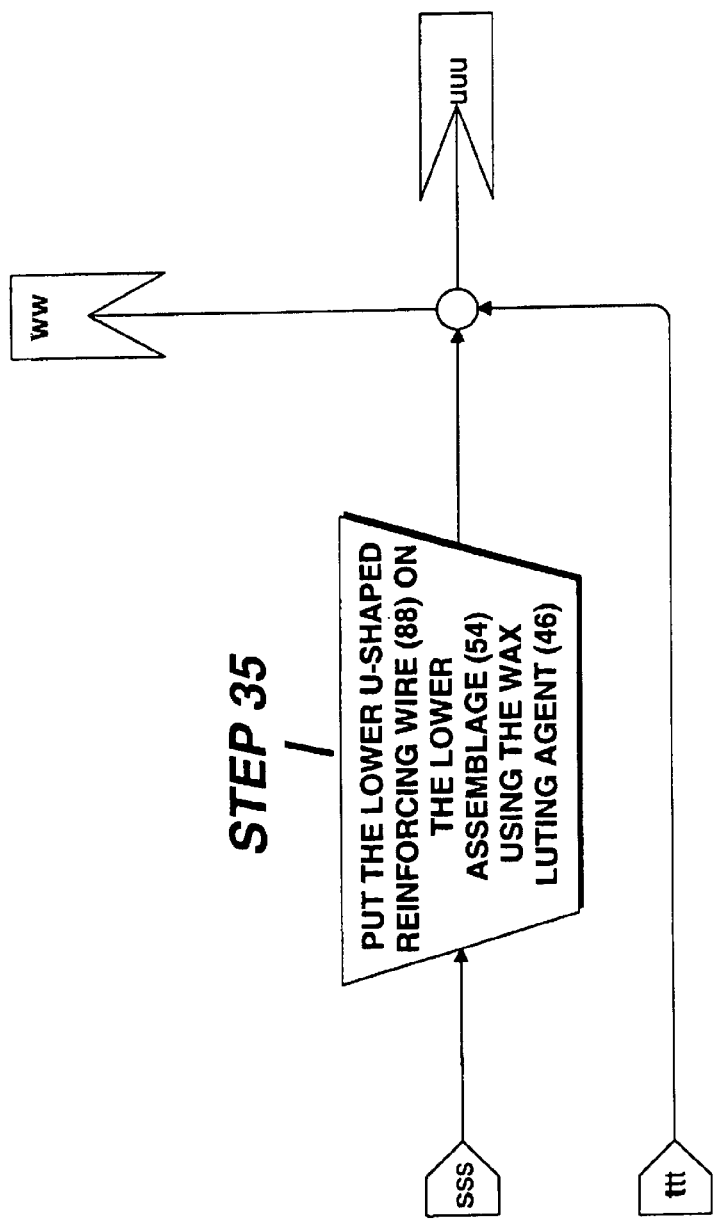
FIG 12-LLL

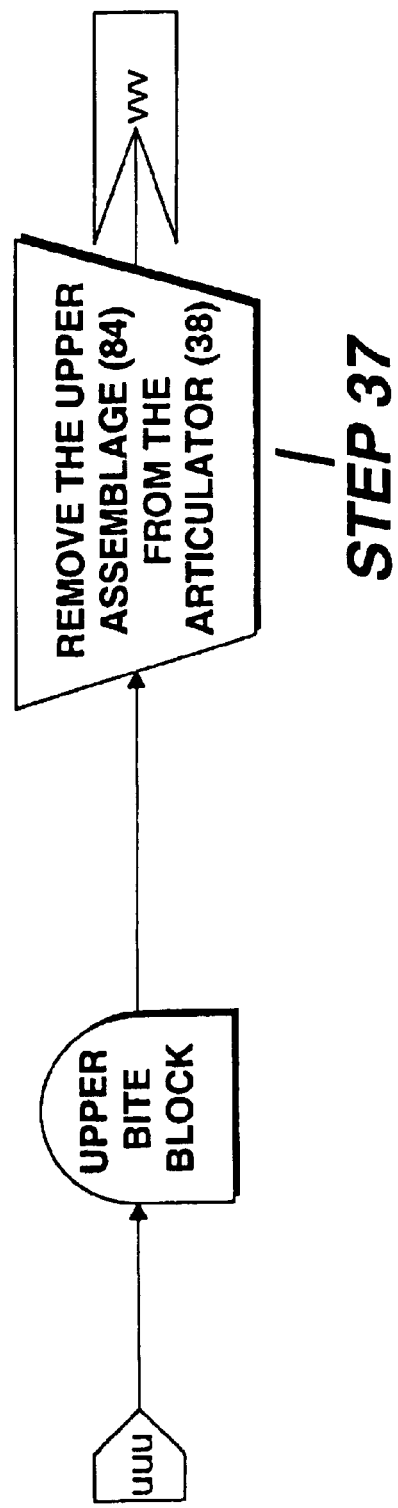
FIG 12-MMM

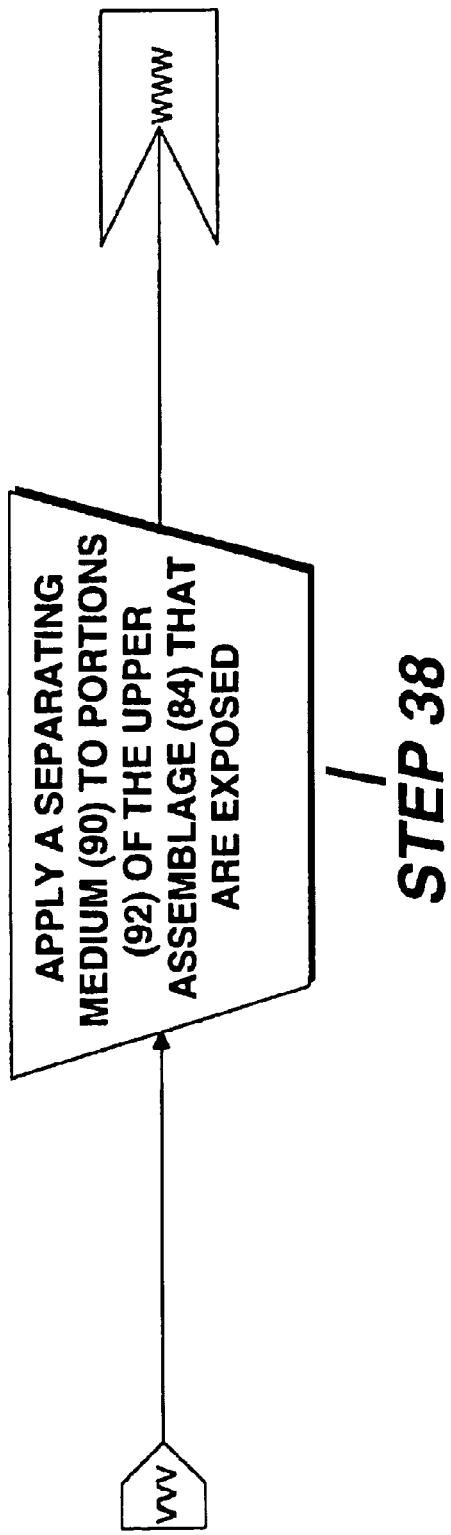
FIG 12-NNN

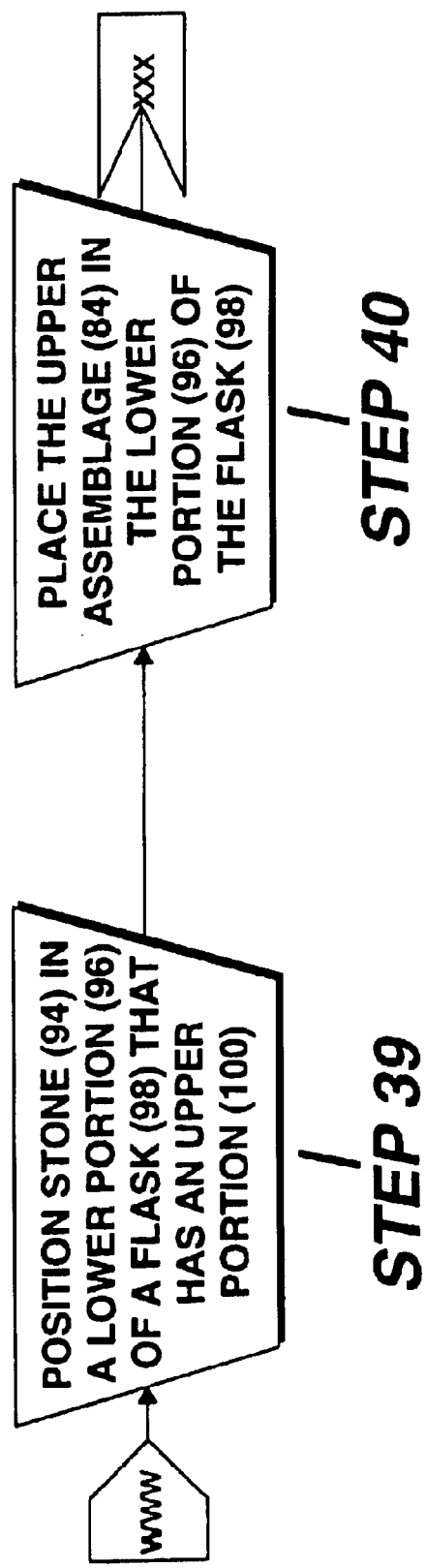
FIG 12-OOO

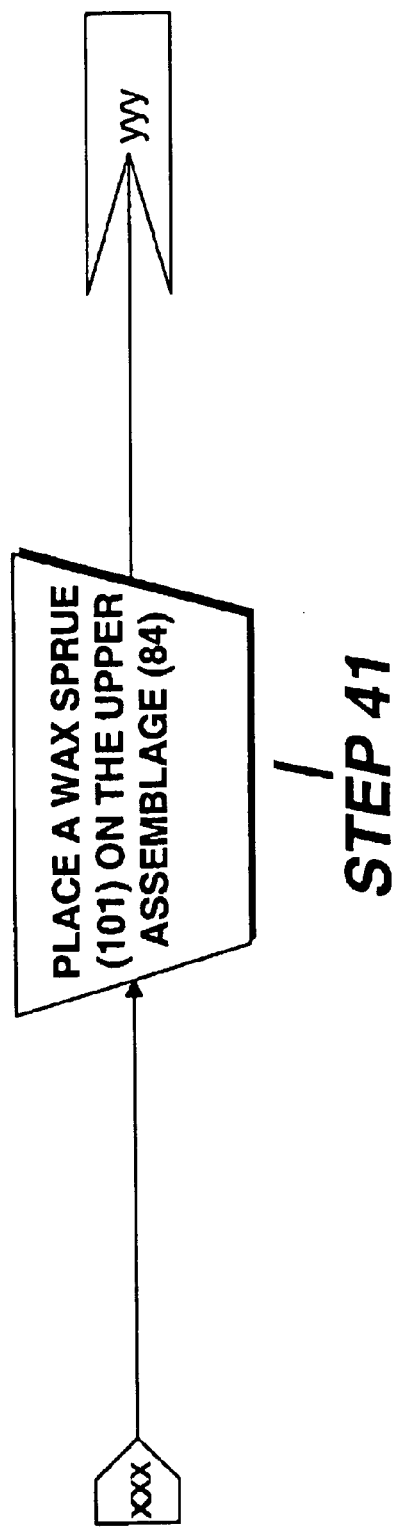
FIG 12-PPP

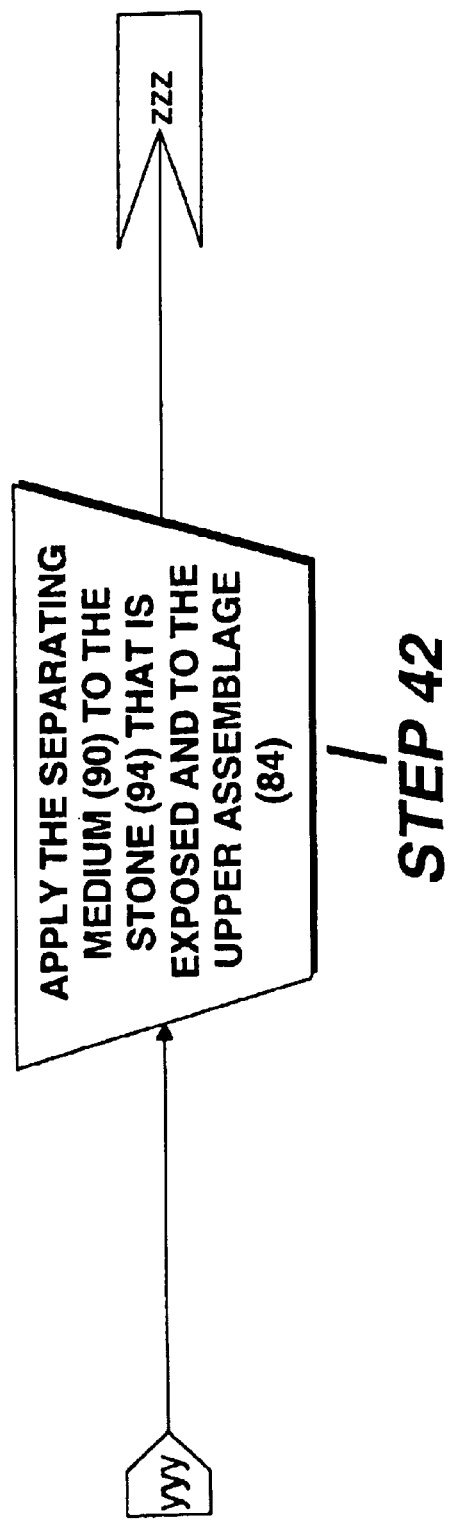
FIG 12-QQQ

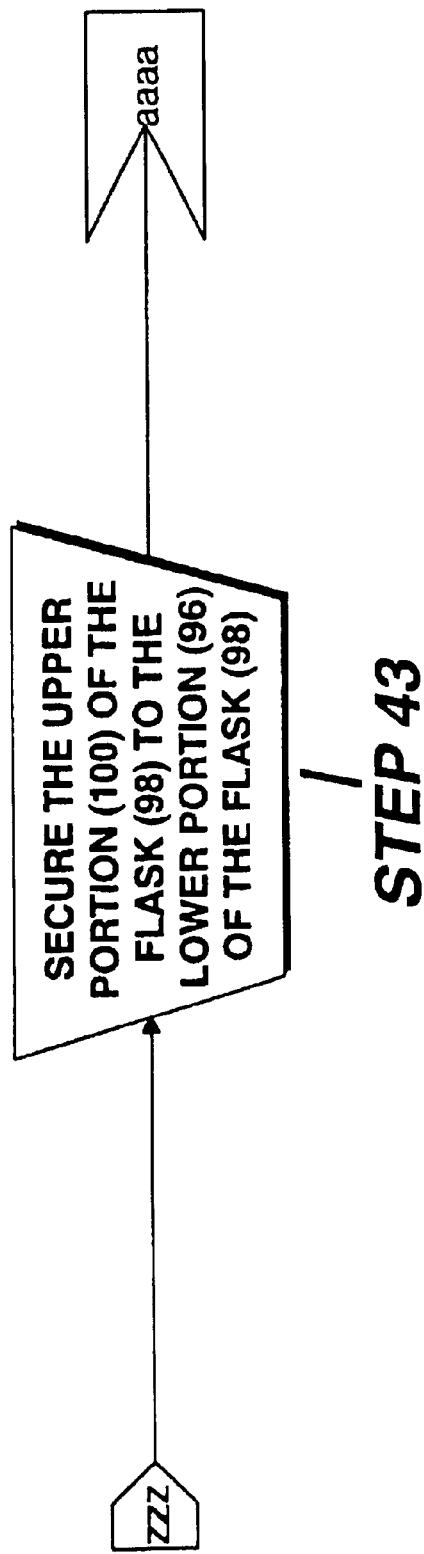
FIG 12-RRR

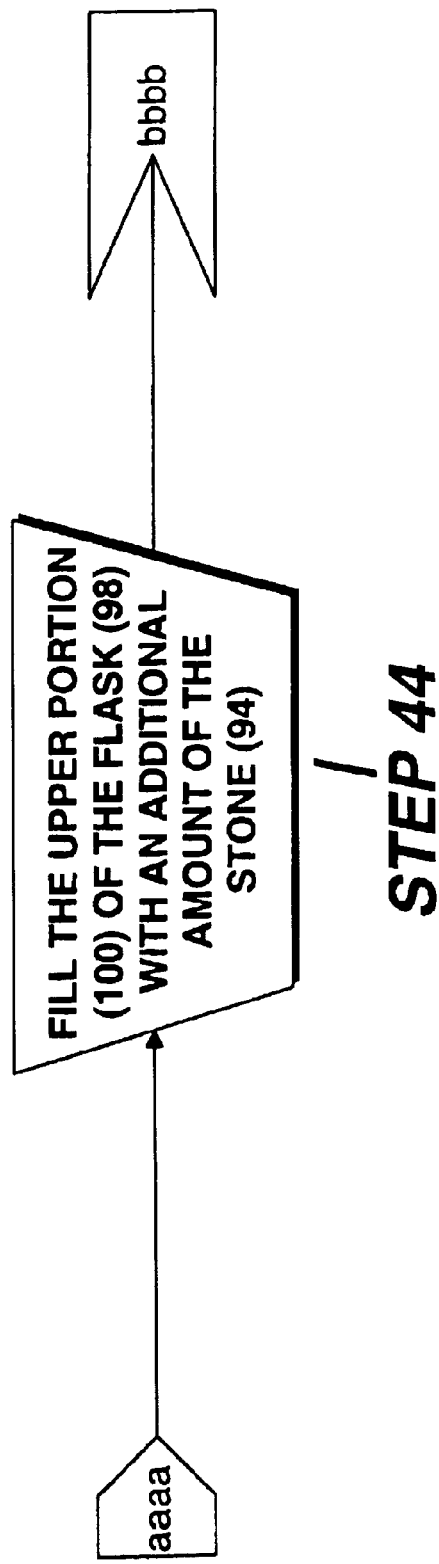
FIG 12-SSS

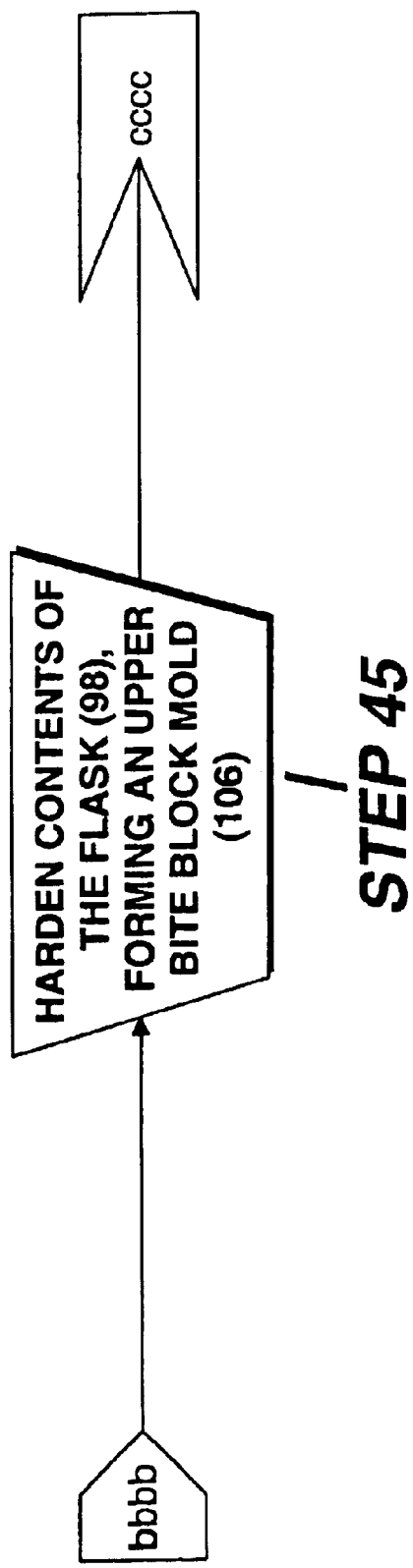
FIG 12-TTT

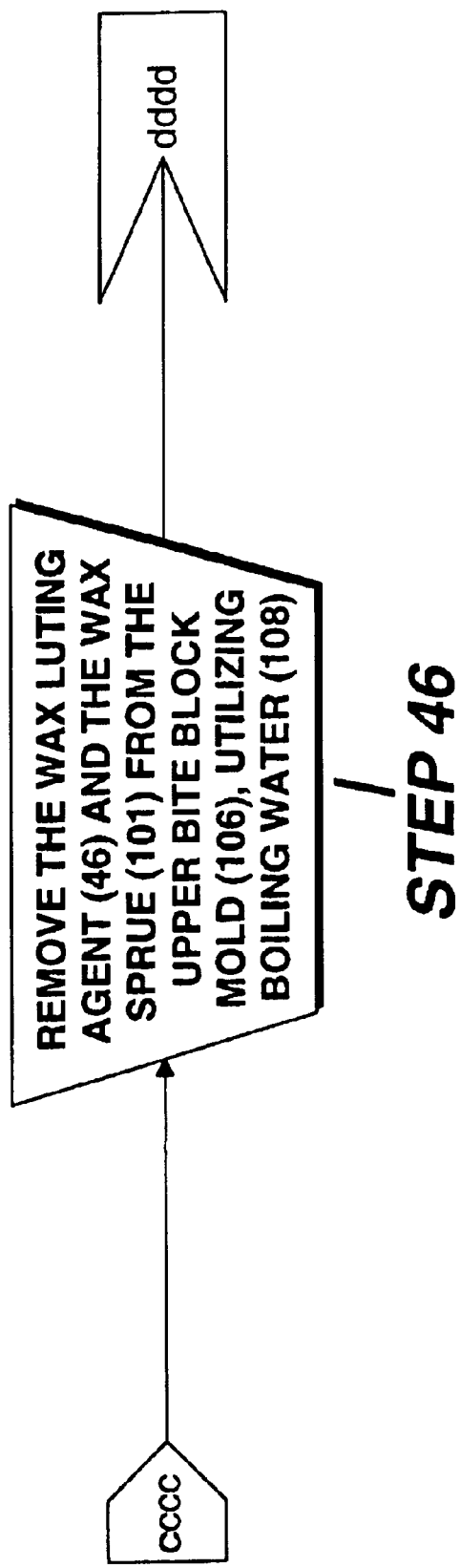
FIG 12-UUU

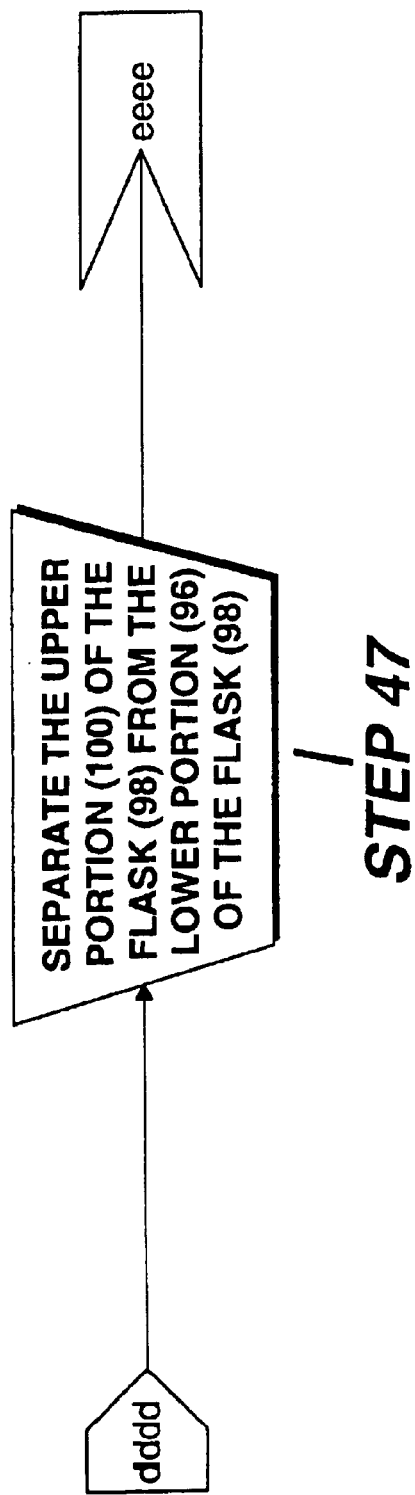
FIG 12-VVV

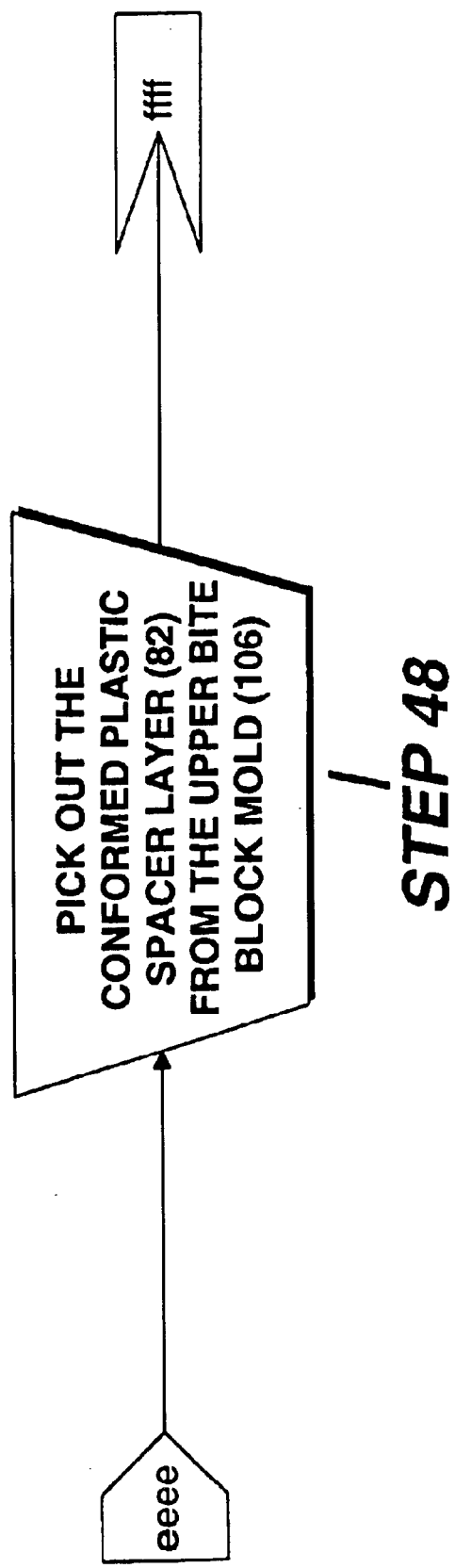
FIG 12-WWW

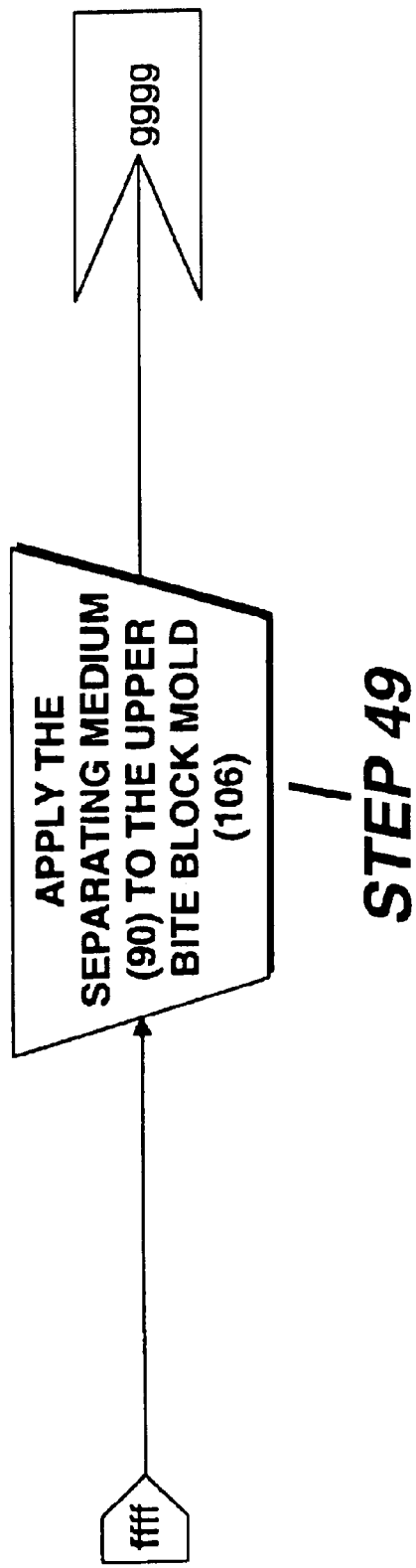
FIG 12-XXX

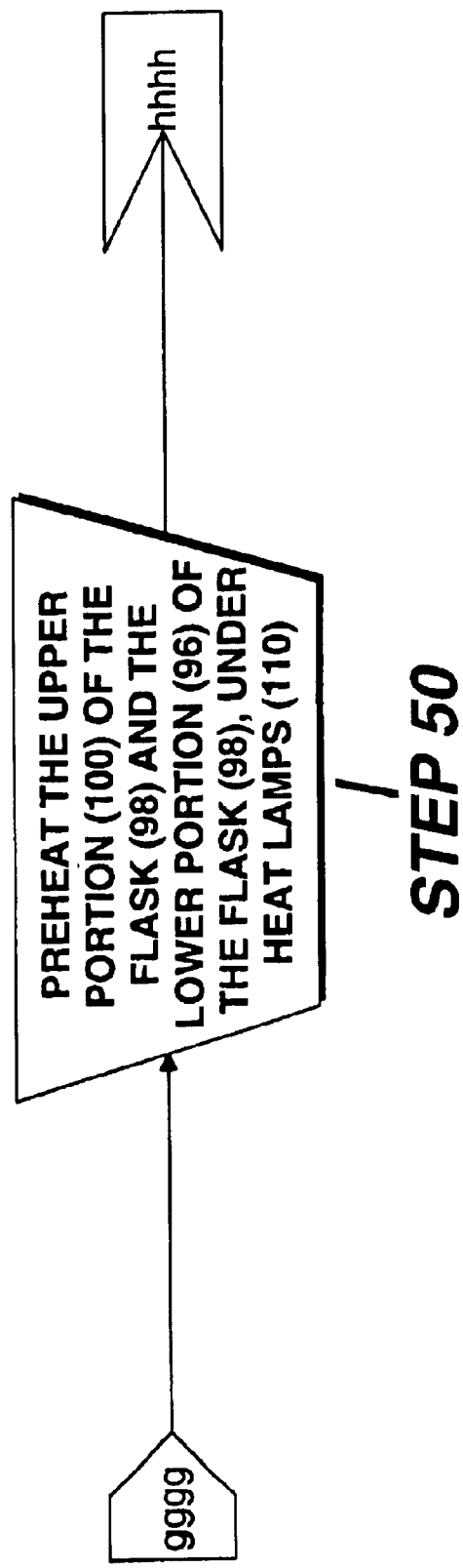
FIG 12-YYY

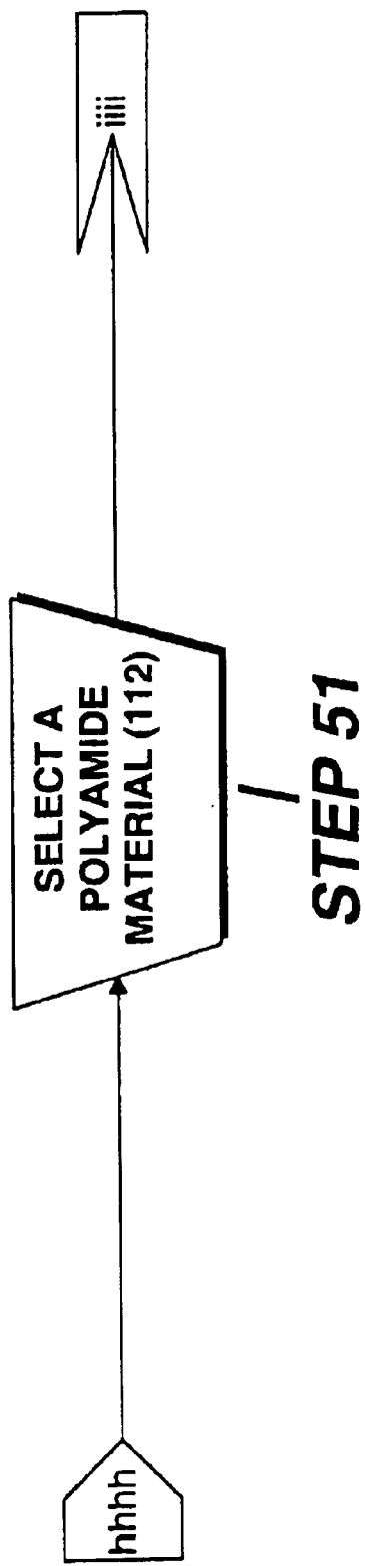
FIG 12-ZZZ

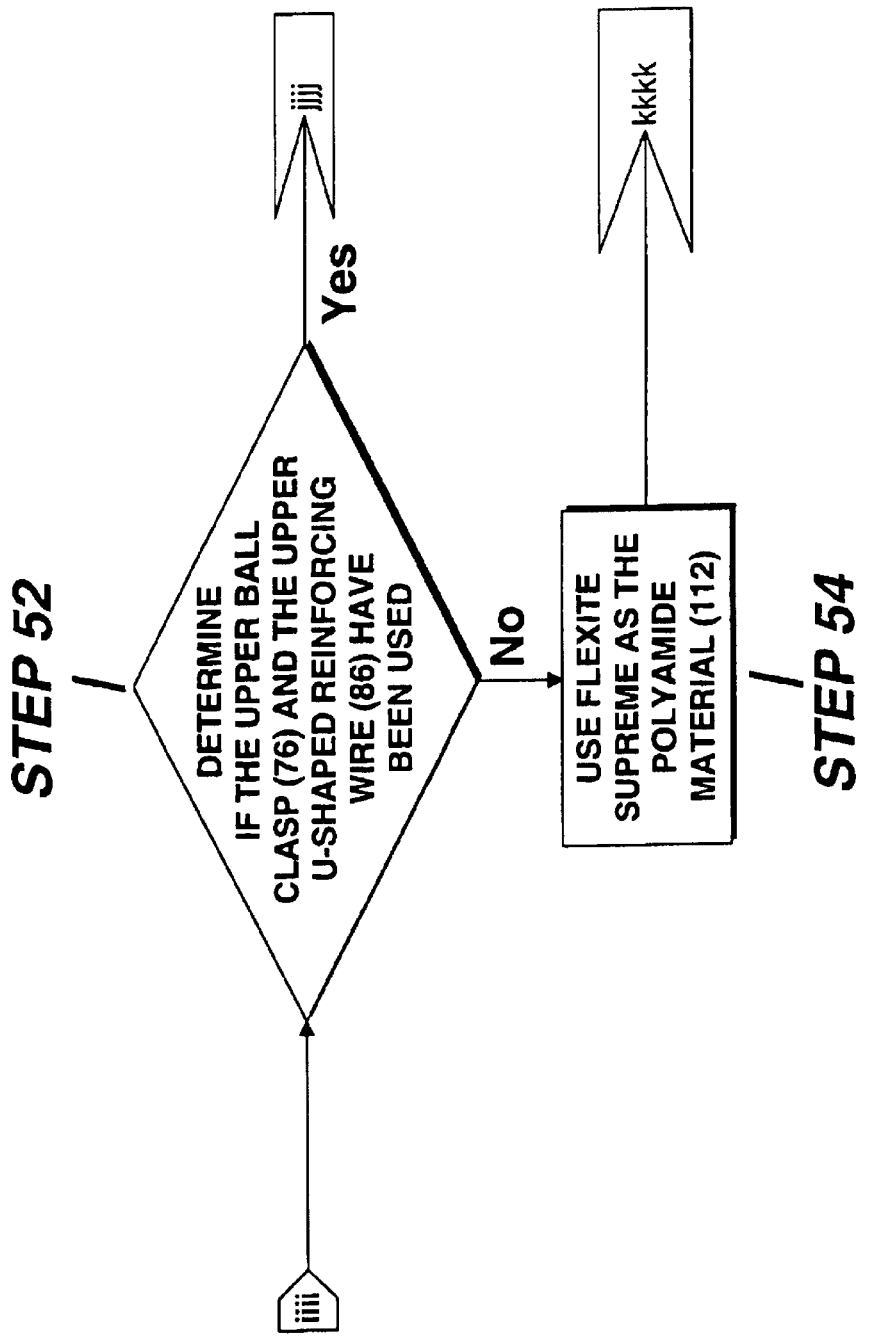
FIG 12-AAAA

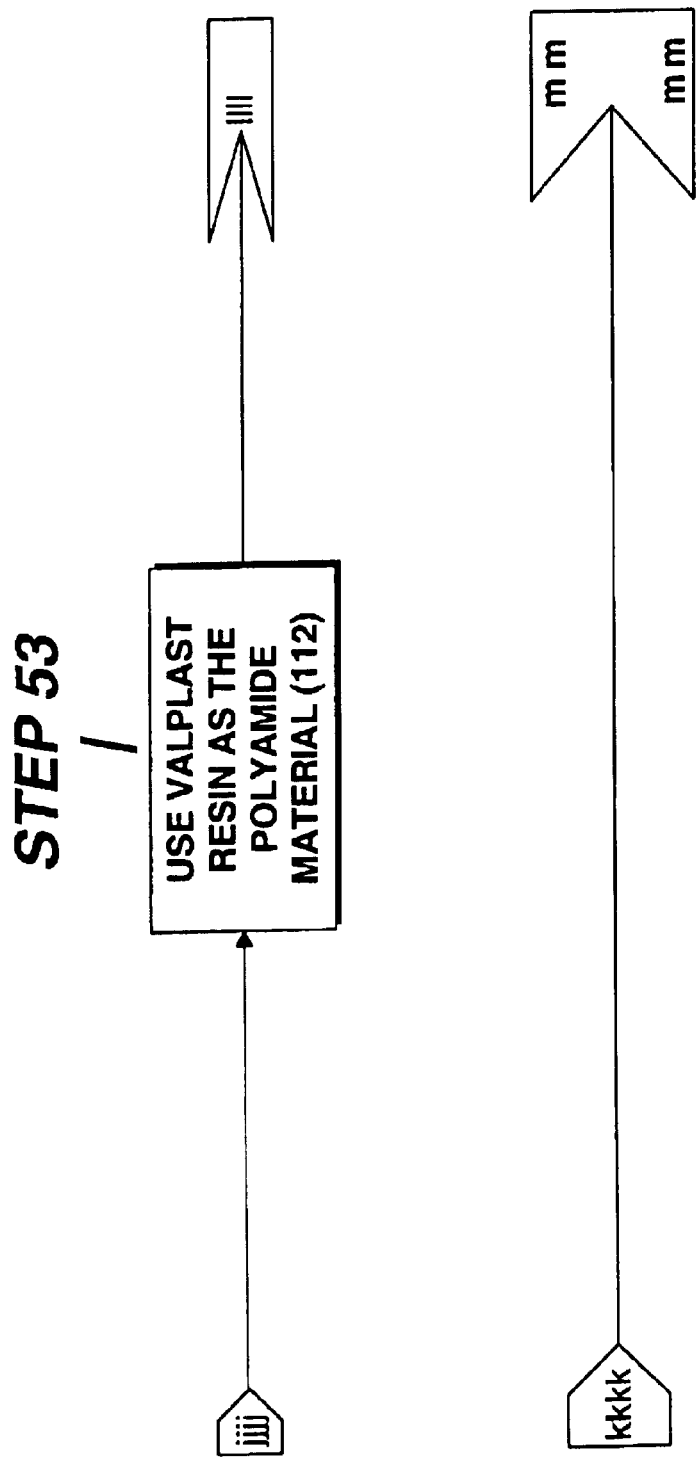
FIG 12-BBBB

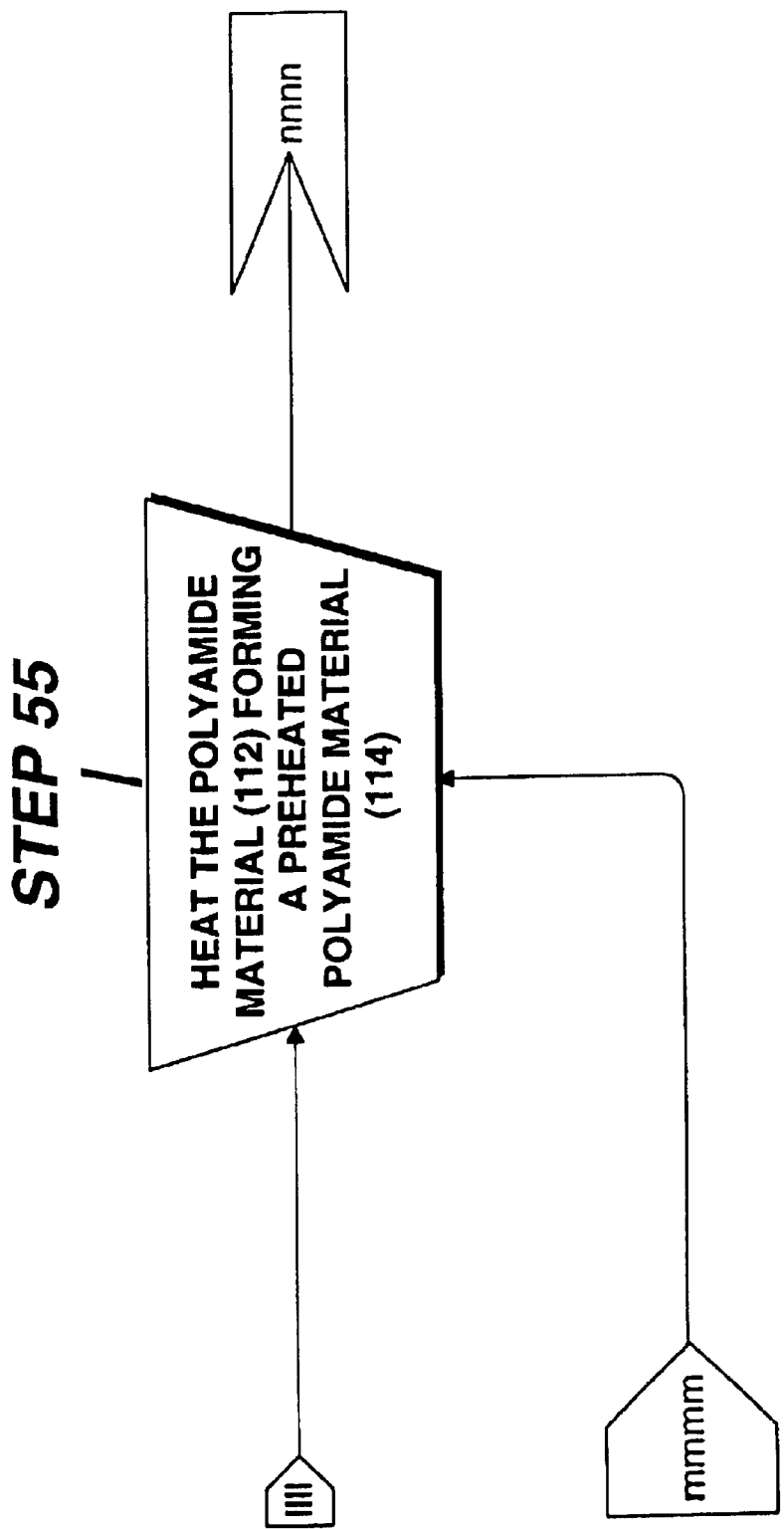
FIG 12-CCCC

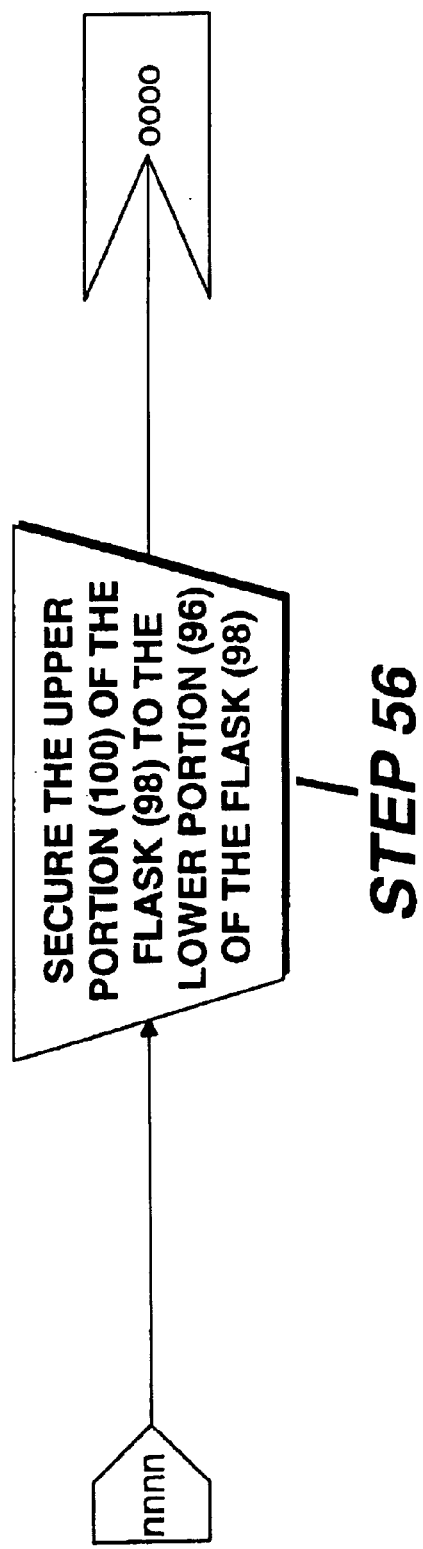
FIG 12-DDDD

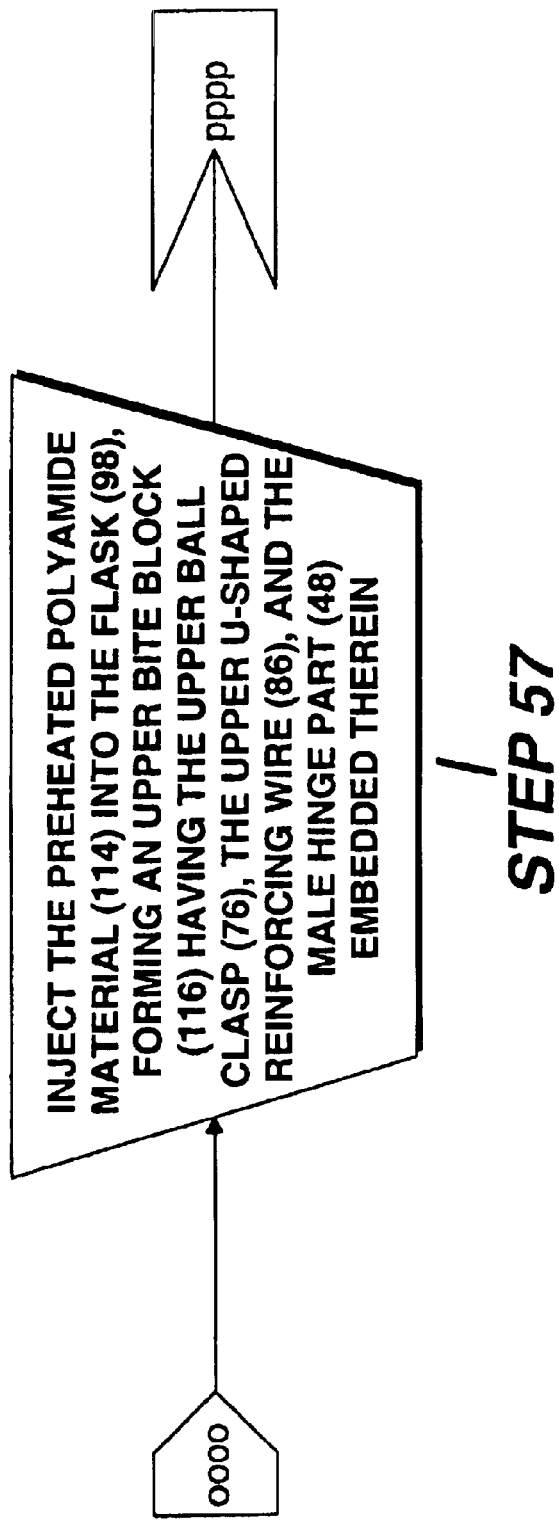
FIG 12-EEEE

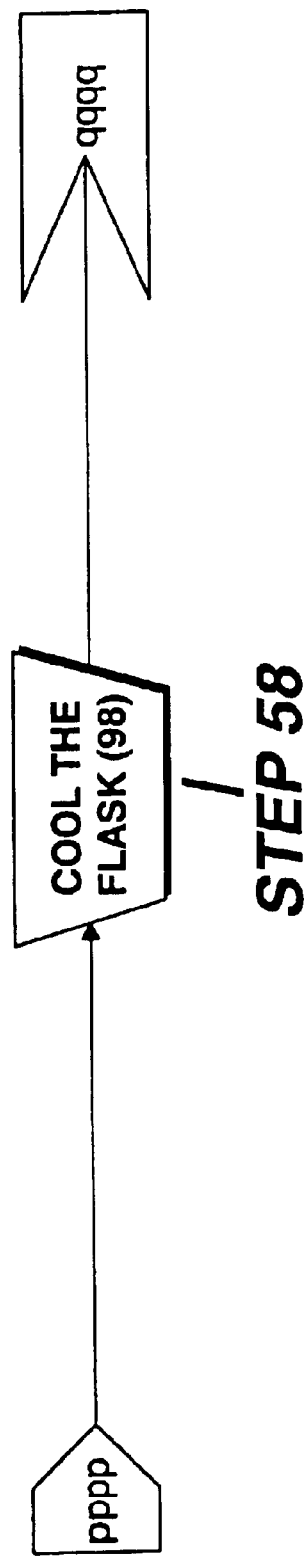
FIG 12-FFFF

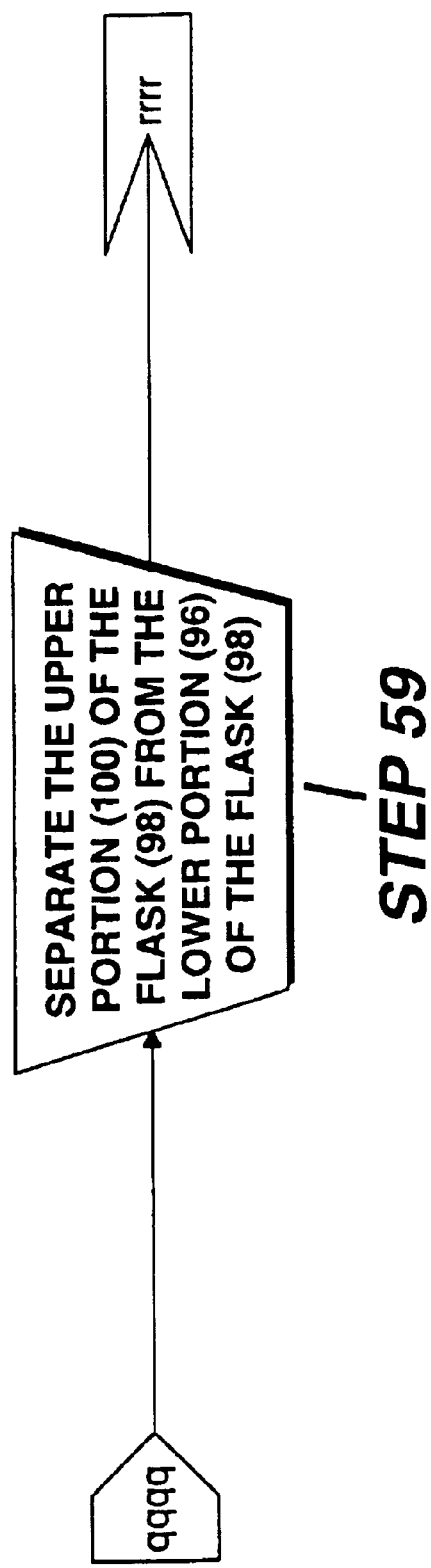
FIG 12-GGGG

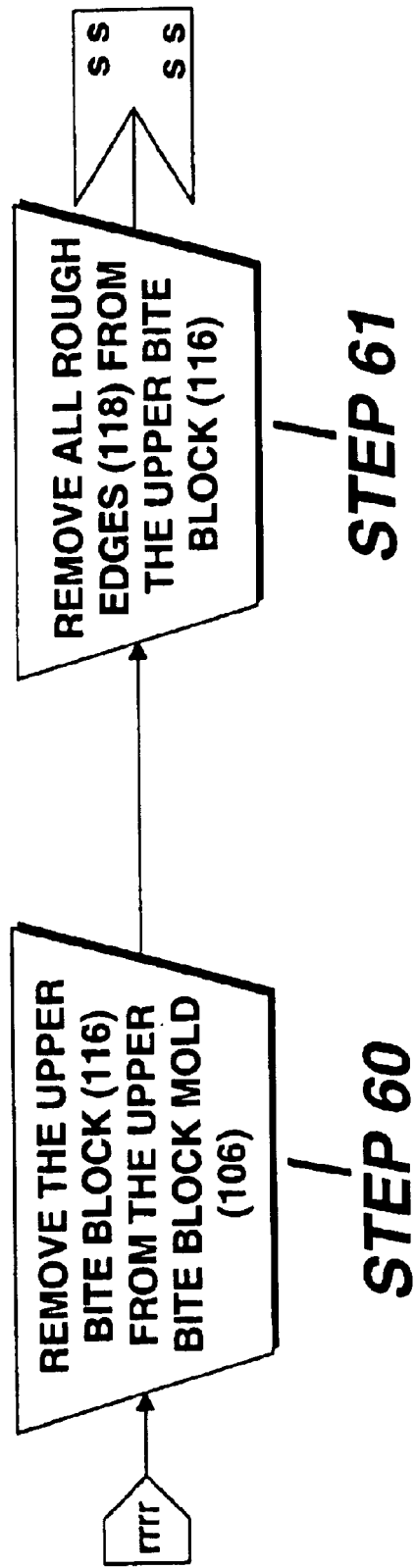
FIG 12-HHHH

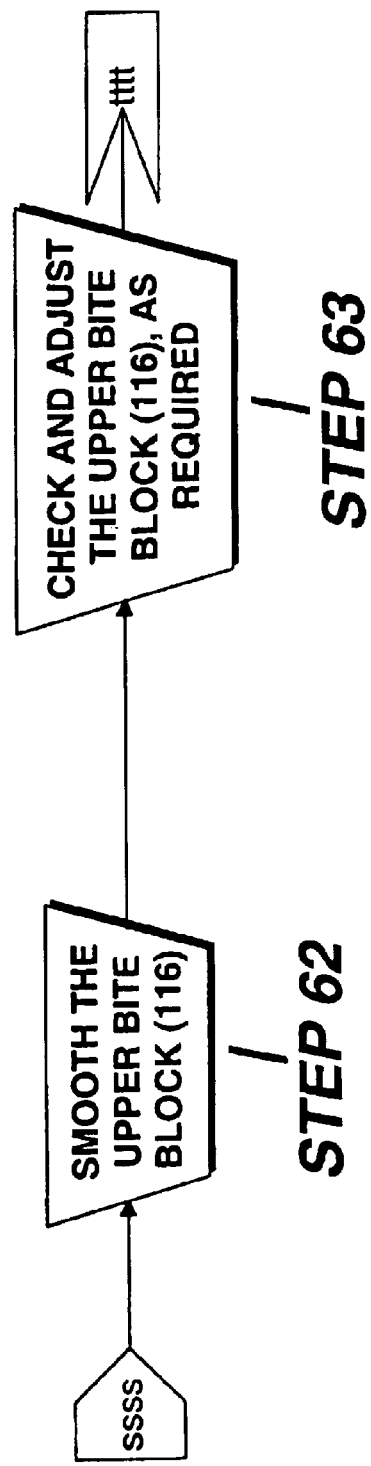
FIG 12-IIII

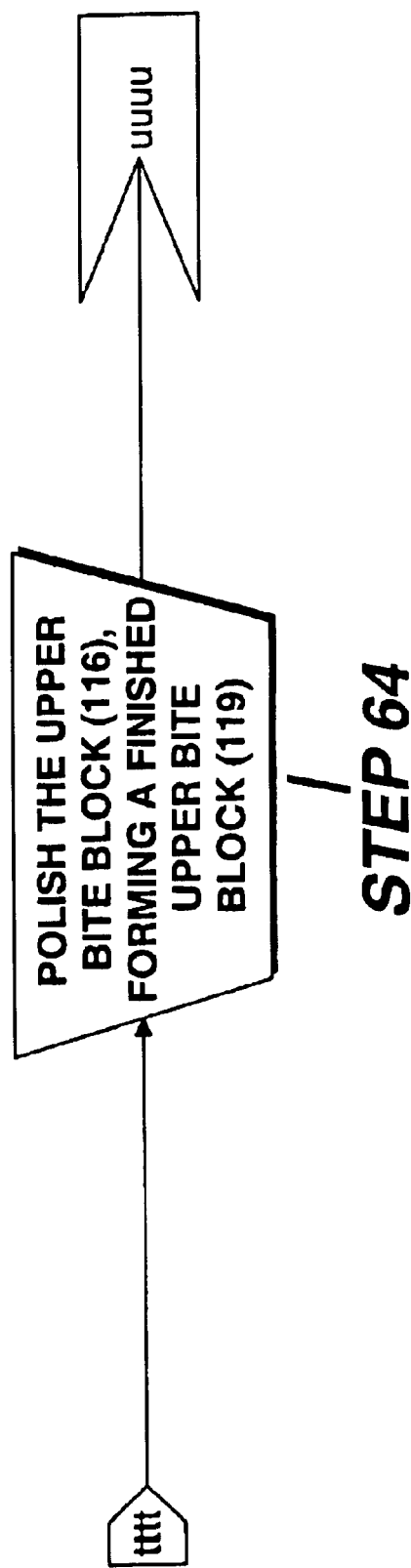
FIG 12-JJJJ

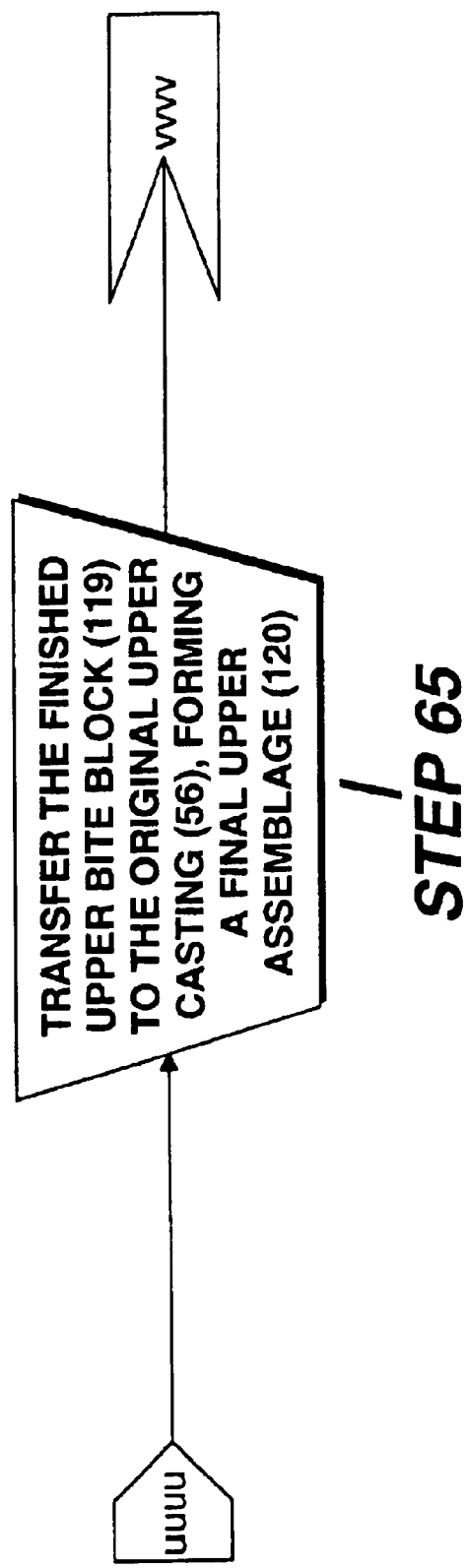
FIG 12-KKKK

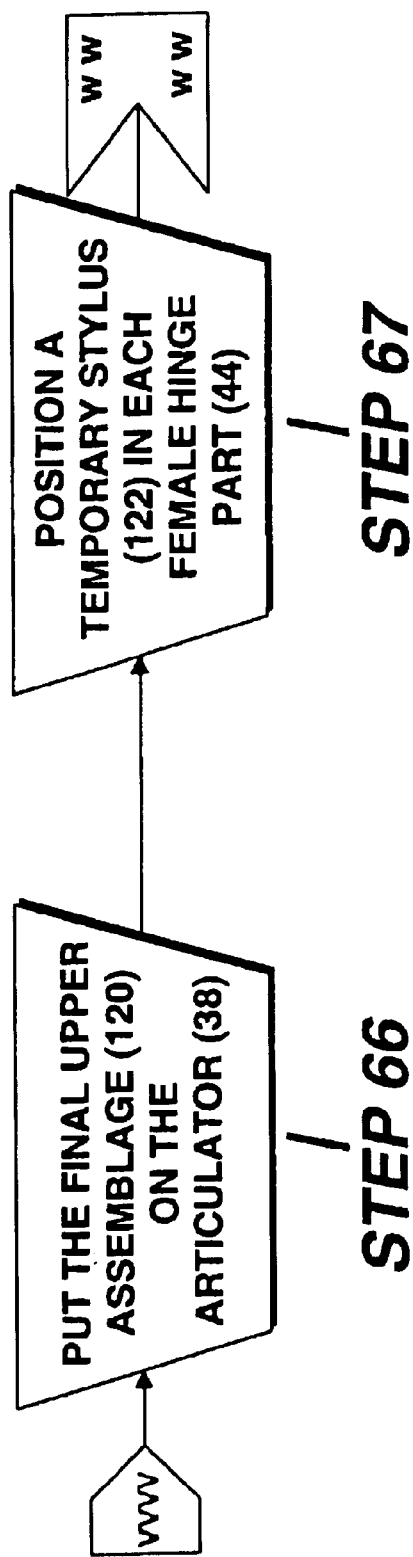
FIG 12-LLLL

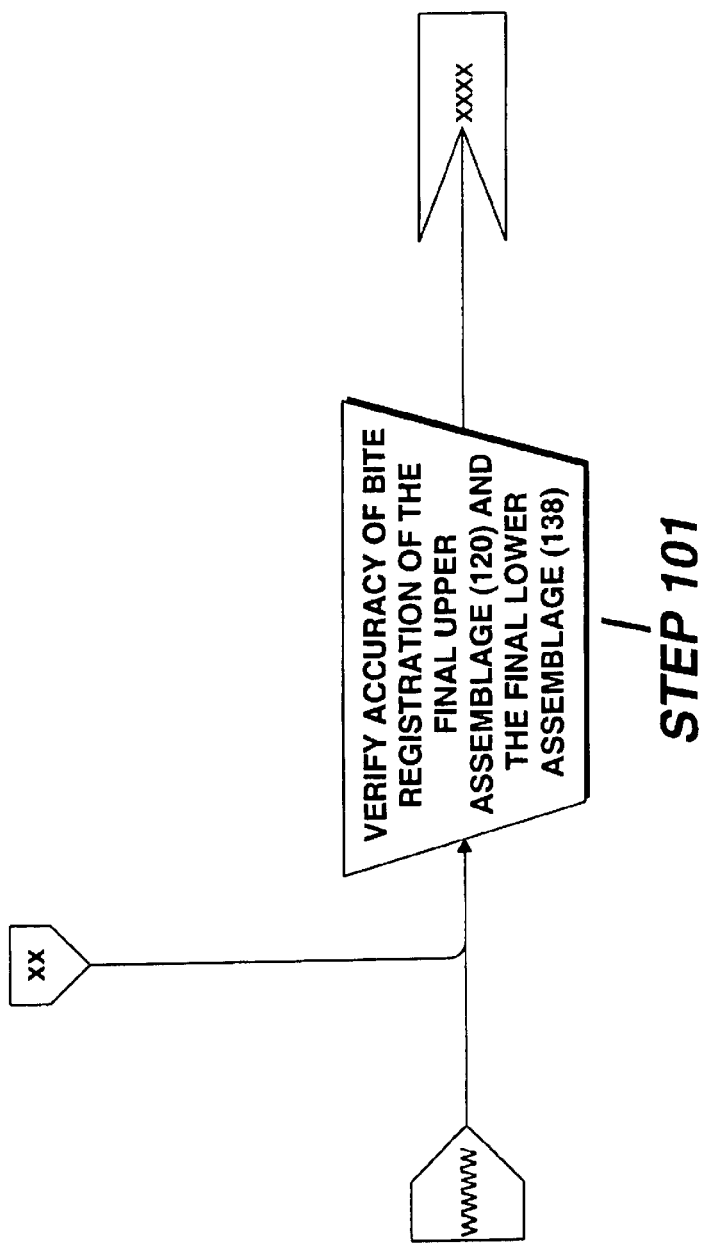
FIG 12-MMMM

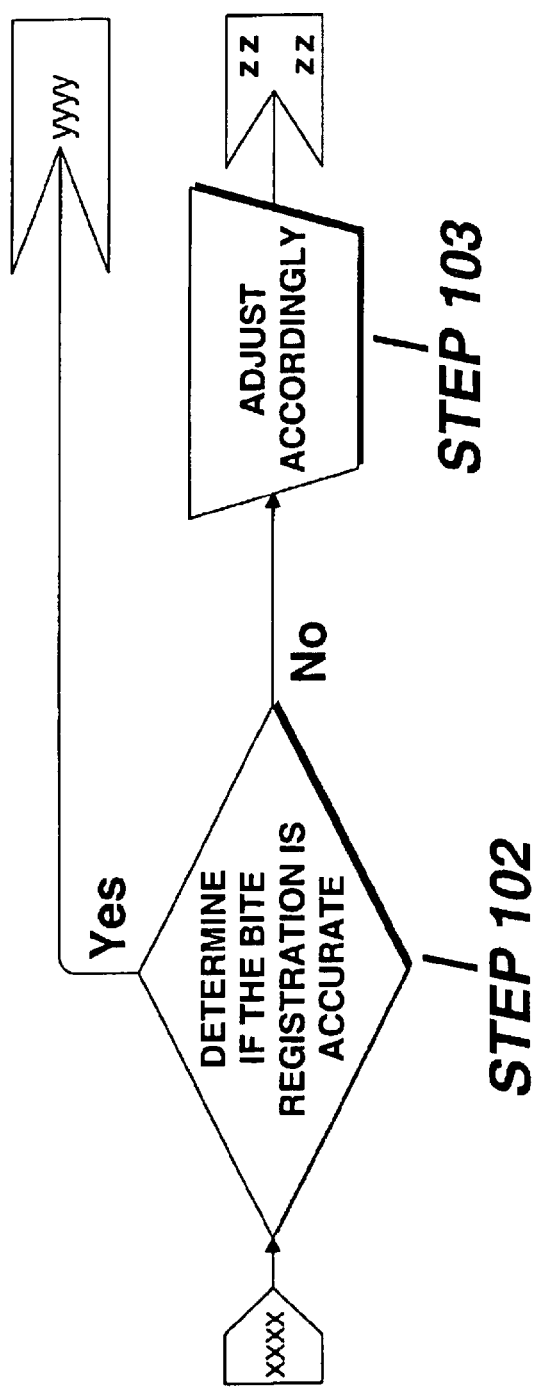
FIG 12-NNNN

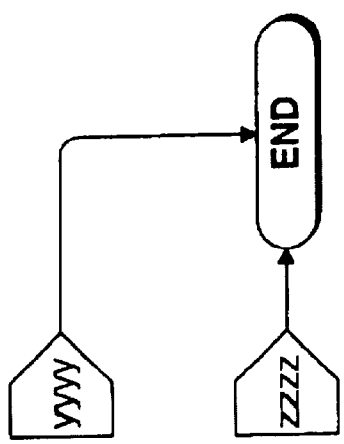
FIG 12-0000

METHOD OF FABRICATING A FLEXIBLE RETENTIVE BITE BLOCK

BACKGROUND OF THE INVENTION

1. Field of the Invention

The present invention relates to a method of fabricating. More particularly, the present invention relates to a method of fabricating a flexible retentive bite block.

2. Description of the Prior Art

Snoring and Obstructive sleep apnea are typically caused by complete or partial obstruction of an individuals pharyngeal airway during sleep. Usually, airway obstruction results from the apposition of the rear portion of the tongue or soft palate with the posterior pharyngeal wall.

Obstructive sleep apnea is a potentially lethal disorder in which breathing stops during sleep for 10 seconds or more, sometimes up to 300 times per night. Snoring occurs when the pharyngeal airway is partially obstructed, resulting in vibration of the oral tissues during respiration. These sleep disorders tend to become more severe as patients grow older, likely as a result of a progressive loss of muscle tone in the patient's throat and oral tissues.

Habitual snoring and sleep apnea have been associated with other potentially serious medical conditions, such as hypertension, ischemic heart disease and strokes. Accordingly, early diagnosis and treatment is recommended.

One surgical approach, known as uvulopalatopharyngoplasty, involves removal of a portion of the soft palate to prevent closure of the pharyngeal airway during sleep. This operation, however, is not always effective and may result in undesirable complications, such as nasal regurgitation.

A wide variety of non-surgical approaches for treating sleep disorders have been proposed including the use of oral cavity appliances. It has been previously recognized that movement of the mandible (lower jaw) forward relative to the maxilla (upper jaw) can eliminate or reduce sleep apnea and snoring symptoms by causing the pharyngeal air passage to remain open.

Several intra-oral dental appliances have been developed which the user wears at night to fix the mandible in an anterior, protruded (i.e. forward) position. Such dental appliances essentially consist of acrylic or elastomeric bite blocks, similar to orthodontic retainers or athletic mouth guards, which are custom-fitted to the user's upper and lower teeth and which may be adjusted to vary the degree of anterior protrusion.

While prior art dental appliances have proven effective in maintaining the mandible in a protruded position to improve airway patency, they often result in undesirable side effects. One of the most common side effects is aggravation of the temporomandibular joint and related jaw muscles and ligaments, especially in individuals who have a tendency to grind their teeth during sleep.

Aggravation of the temporomandibular joint has been associated with a wide variety of physical aliments, including migraine headaches. Accordingly, many individuals suffering from sleep apnea and snoring disorders are not able to tolerate existing anti-snoring dental appliances for long periods of time.

The need has therefore arisen for a dental appliance for treatment of snoring and sleep apnea which will maintain the mandible in a preferred anterior position, allow a limited degree of lateral excursion of the mandible relative to the upper jaw to avoid discomfort to the temporomandibular joint and related muscles and ligaments, and be replaceably maintained on the user's teeth by virtue of its own flexibility and thereby eliminating the need for dental wires that can aggravate the teeth and gums and which require the appliance to have thick walls for their support which can lead to further discomfort for the user, such as gum and cheek irritation and gagging.

Numerous innovations for mouthpieces have been provided in the prior art that will be described. Even though these innovations may be suitable for the specific individual purposes to which they address, however, they differ from the present invention.

FOR EXAMPLE, U.S. Pat. No. 5,203,324 to Kinkade teaches a mouthpiece for use in diving or medical equipment, among others made of moldable resilient material having an offset between upper and lower jaw, a bite plane which is tapered with the bite plane formed by wings which have varying thickness to create the taper in which the wing members have substantially vertical surfaces on either side thereof for contacting the lateral surfaces of the user's cuspids and bicuspids and in which the main body portion has upper and lower apron and eminence skirts for avoiding contact with the user's frenum and cuspid eminence and in which the internal wing members have a range in size, at the cuspid, from about 6 to about 12 mm in width, from about 14 to about 40 mm in length and from about 2 mm to about 8 mm in thickness. The greater the offset, the shorter the length of the internal wind members.

ANOTHER EXAMPLE, U.S. Pat. No. 5,365,945 to Halstrom teaches a dentally retained intra-oral appliance worn at night for treatment of snoring and obstructive sleep apnea. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscle and ligaments.

STILL ANOTHER EXAMPLE, U.S. Pat. No. 5,409,017 to Lowe teaches a mandible repositioning appliance formed by an upper bite block and a lower bite block interconnected by an adjustable mechanism including a posterior section connected to the rear portion of the upper bite block and an anterior section connected to the front portion of the lower bite block and an adjustable interconnection between the anterior and posterior sections. Preferably, the adjustable interconnection includes a double thread element rotation of which changes the relative positions of the posterior and interior sections axially of the appliance and abutments to define each incremental rotation of the element. The comfort of the wearer is further improved by using a heat sensitive material in the tooth retention sections and by permitting limited relative lateral movement between the bite blocks.

YET ANOTHER EXAMPLE, U.S. Pat. No. 5,499,633 to Fenton teaches an adjustable oral device for placement within the mouth of a user to reduce or eliminate snoring. The device comprises an upper member having a substantially curved shape and defining an upwardly oriented channel for receiving at least some of the upper teeth of a user. A lower member has a substantially curved shape and defines a downwardly oriented channel for receiving at least some of the lower teeth of a user. The upper member is adjustably coupled by the user to the lower member in a spaced relationship such that the lower member is positioned relative to the upper member so that when the user's teeth are retained within the device, the user's lower jaw is biased substantially forward of its normal biting or resting position to reduce snoring. The device can include an anterior tongue space between the upper and lower members, and can further include moldable material positioned within at least one of the channels for substantially conforming to a shape of the teeth, thus allowing the device to be customized for individual users.

YET STILL ANOTHER EXAMPLE, U.S. Pat. No. 5,562,106 to Heeke et al. teaches a non-surgical oral appliance for improving breathing, and abating or completely alleviating snoring sounds and symptoms while sleeping. The patient is pre-tested and pre-fitted for the appliance so that the appliance positions the mandible in an open position and protrusive position to hold the mouth partially open. The appliance has a right and left extension wherein each extension has upper and lower surfaces pre-molded to the contour of the patient's back teeth. A bridge connects the right and left extensions having been pre-molded to conform to the upper palate of the patient's mouth. The upper and lower surfaces of each extension are spaced to provide optimum mouth height that was pre-tested to alleviate the snoring sound. Upon insertion, the appliance facilitates an air passage for breathing and also allows the patient to talk while remaining virtually invisible to an observer.

STILL YET ANOTHER EXAMPLE, U.S. Pat. No. 5,823,194 to Lampert, as shown in FIGS. 1 and 2, teaches a dentally retained intra-oral appliance 5 worn at night for treatment of snoring and obstructive sleep apnea and its fabrication process. The appliance 5 maintains the patient's mandible in an anterior, protruded position to prevent obstruction of the pharyngeal airway. The appliance 5 allows a limited degree of lateral movement of the mandible relative to the upper jaw in the protruded position to prevent aggravation of the patient's temporomandibular joint and associated muscles and ligaments. The appliance 5 includes a lower bite block 5A conforming to the patient's mandibular dentition 5B, an upper bite block 5C conforming to the patient's maxillary dentition, and a hinge 5D connecting the upper bite block 5C to the lower bite block 5A. The upper bite block 5C and the lower bite block 5A are thin walled polyamide eliminating the need for dental wires to maintain them to the mandibular detention and the maxillary dentition and the problems associated therewith.

It is apparent that numerous innovations for mouthpieces have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide a method of fabricating a flexible retentive bite block that avoids the disadvantages of the prior art.

BRIEFLY STATED, STILL YET ANOTHER OBJECT of the present invention is to provide a dentally retained intra-oral appliance worn at night for treatment of snoring and obstructive sleep apnea and its fabrication process. The appliance maintains the patient's mandible in an anterior, protruded position to prevent obstruction of the pharyngeal airway. The appliance allows a limited degree of lateral movement of the mandible relative to the upper jaw in the protruded position to prevent aggravation of the patient's temporomandibular joint and associated muscles and ligaments. The appliance includes a lower bite block conforming to the patient's mandibular dentition, an upper bite block conforming to the patient's maxillary dentition, and a hinge connecting the upper bite block to the lower bite block. The upper bite block and the lower bite block are thin walled polyamide eliminating the need for dental wires to maintain them to the mandibular detention and the maxillary dentition and the problem associated therewith.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawing are briefly described an follows:

FIG. 1 is a diagrammatic perspective view of the prior art device taught by U.S. Pat. No. : 5,823,194 to Lampert;

FIG. 2 is a diagrammatic side elevational view of the prior art device installed on a tooth;

FIG. 3 is a diagrammatic side elevational view of STEPS 2, 3, 18, and 19 of the present invention;

FIG. 6 is an exploded diagrammatic perspective view of STEPS 13 and 14 of the present invention;

FIG. 6A is a diagrammatic perspective view of STEP 14 of the present invention;

FIG. 7 is an exploded diagrammatic perspective view of STEPS 72, 73, and 74 of the present invention;

FIG. 8 is an exploded diagrammatic perspective view of STEPS 40, 41, and 42 of the present invention;

FIG. 9 is a diagrammatic perspective view of STEPS 66, 100, and 101 of the present invention;

FIG. 10AA is a diagrammatic bottom plan view of the area generally enclosed by the dotted curve identified by ARROW 10AA in FIG. 9 of a finished upper bite block without the ball clasp and the reinforcing wire;

FIG. 10BB is a diagrammatic top plan view of the area generally enclosed by the dotted curve identified by ARROW 10BB in FIG. 9 of a finished lower bite block without the ball clasp and the reinforcing wire;

FIG. 11 is a diagrammatic cross sectional view taken along LINE 11—11 in FIG. 9; and FIGS. 12-A to 12-0000 is a block diagram of the process flow of the present invention.

LIST OF REFERENCE NUMERALS UTILIZED IN THE DRAWING

Figure 4:
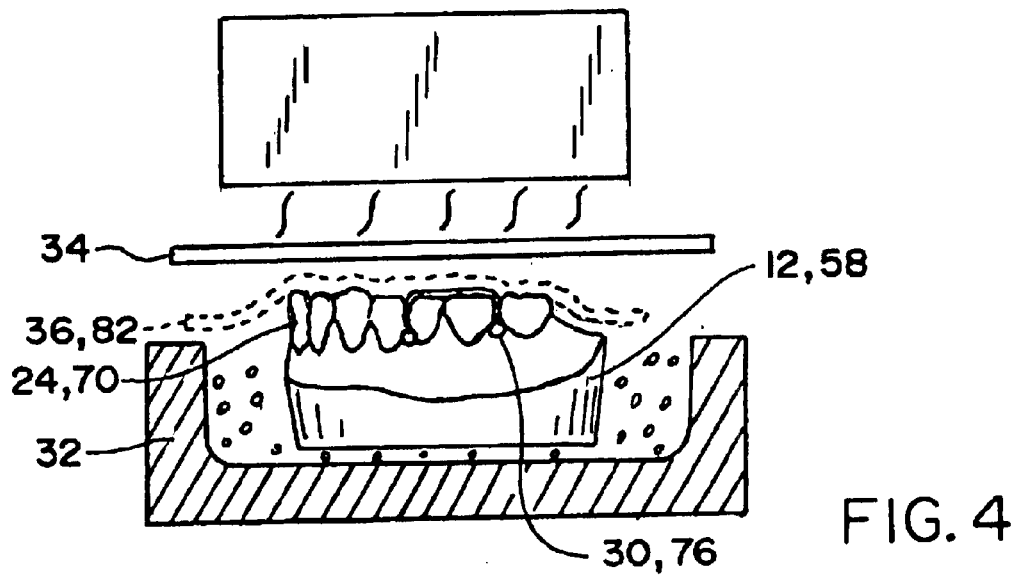
FIG. 4 is a diagrammatic side elevational view of STEPS 6, 8, 9, 10, 22, 24, 25, and 26 of the present invention.

Prior Art 5 appliance
5A lower bite block for confronting to patient's mandibular dentition 5B
5B patient's mandibular dentition
5C upper bite block for conforming to patient's maxillary dentition
5D hinge connecting upper bite block 5C to lower bite block 5A

Present Invention 10 original lower casting
12 lower duplicate casting
14 gum of original lower casting 10
16 teeth of original lower casting 10
18 supra bulges of teeth 16 of original lower casting 10
20 posterior portions of teeth 16 of original lower casting 10
22 bite surfaces of posterior portion 20 of teeth 16 of original lower casting 10
24 teeth of lower duplicate casting 12
26 surveying line of original lower casting 10
28 extended surveying line of original lower casting 10
30 lower ball clasp
32 heat pressure former
34 at least one plastic spacer sheet
38 conformed plastic spacer layer of lower duplicate casting 12
38 articulator
40 flat plastic spacer on bottom 42 of female hinge pert 44
42 bottom of female hinge part 44
44 female hinge part
46 wax luting agent
48 male hinge part
50 assembly
54 lower assemblage
56 original upper casting
58 Upper duplicate casting
60 gum of original upper casting 56
62 teeth of original upper casting 56
64 supra bulges of teeth 82 of original upper casting 56
68 posterior portions of teeth 62 of original upper casting 56
68 bite surfaces of posterior portions 66 of teeth 62 of original upper casting 56
70 teeth of upper duplicate casting 58
72 surveying line of original upper casting 56
74 extended surveying line of original upper casting 56
76 upper ball clasp
82 conformed plastic spacer layer of upper duplicate casting 58
84 upper assemblage
86 upper U-shaped reinforcing wire
88 lower U-shaped reinforcing wire
90 separating medium
94 stone
98 lower portion of flask 98
98 flask
100 upper portion of flask 98
101 wax sprue
106 upper bite block mold
108 boiling water
110 heat lamps
112 polyamide material
114 preheated polyamide material
116 upper bite block
118 rough edges of upper bite block 116
119 finished upper bite block
120 final upper assemblage
122 temporary stylus
124 exposed portions of lower assemblage 54
128 additional amount of stone 94
130 lower bite block mold
132 lower bite block
134 rough edges of lower bite block 132
136 finished lower bite block
138 final lower assemblage

DETAILED DESCRIPTION OF THE PREFERRED EMBODIMENT

Referring now to FIGS. 3 to 12-000, in which like numerals indicate like parts, the method of fabricating a flexible retentive bite block comprises the steps of:

STEP 1: As shown in FIG. 12-TT, make a duplicate of an original lower casting 10, forming a lower duplicate casting 12, wherein the original lower casting 10 has a gum 14, teeth 16 with supra bulges 18 and posterior portions 20 with bite surfaces 22, and wherein the lower duplicate casting 12 has teeth 24.

STEP 2: As shown in FIGS. 3 and 12-UU, survey the original lower casting 10, forming a surveying line 26 thereon.

STEP 3: As shown in FIGS. 3 and 12-VV, extend the surveying line 26 approximately 1 mm past the supra bulges 18 of the teeth 16 of the original lower casting 10, toward the gum 14 of the original lower casting 10, forming an extended surveying line 28.

STEP 4: As shown in FIG. 12-WW, set the original lower casting 10 aside.

STEP 5: As shown in FIG. 12-WW, determine if a lower ball clasp 30 is to be used.

STEP 6: As shown in FIGS. 4 and 12-XX, put the lower ball clasp 30 on the lower duplicate casting 12, if answer to STEP 5 is yes and proceeding to STEP 8.

STEP 7: As shown in FIG. 12-XX proceed directly to STEP 8, if answer to STEP 5 is no.

STEP 8: As shown in FIGS. 4 and 12-XX, put the lower duplicate casting 12 in a heat pressure former 32.

STEP 9: As shown in FIGS. 4 and 12-YY, position at least one plastic spacer sheet 34 on the teeth 24 of the lower duplicate casting 12.

STEP 10: As shown in FIGS. 4 and 12-ZZ, activate the heat pressure former 32, causing the at least one plastic spacer sheet 34 to melt and conform to the teeth 24 of the lower duplicate casting 12, forming a conformed plastic spacer layer 36 thereon.

STEP 11: As shown in FIG. 12-AAA, remove the lower duplicate casting 12 with the conformed plastic spacer layer 36 thereon from the heat pressure former 32.

STEP 12: As shown in FIG. 12-BBB, put the lower duplicate casting 12 with the conformed plastic spacer layer 36 thereon in an articulator 38.

STEP 13: As shown in FIGS. 6 and 12-CCC, put a flat plastic spacer 40 on a bottom 42 of a female hinge part 44 using a wax luting agent 46.

STEP 14: As shown in FIGS. 6, 6A, and 12-DDD, put a male hinge part 48 into the female hinge peat 44 and tack together with the wax luting agent 46, forming an assembly 50.

Figure 5:
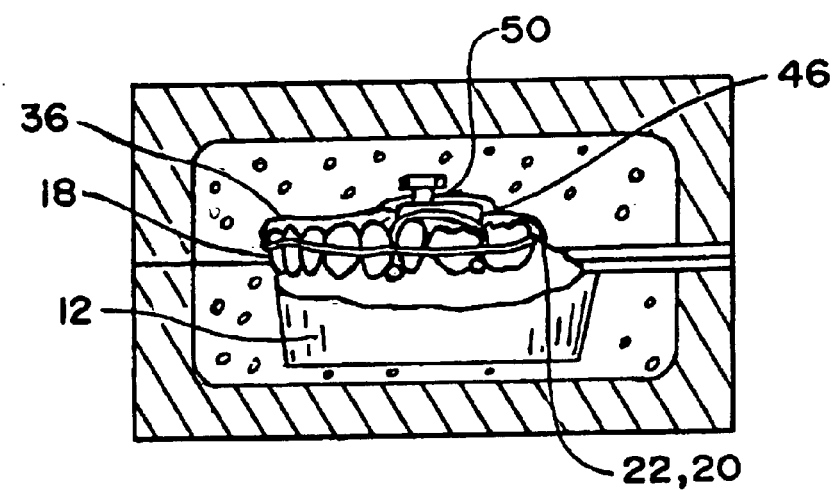
FIG. 5 is a diagrammatic side elevational view of STEP 15 of the present invention.
Figure 10A:
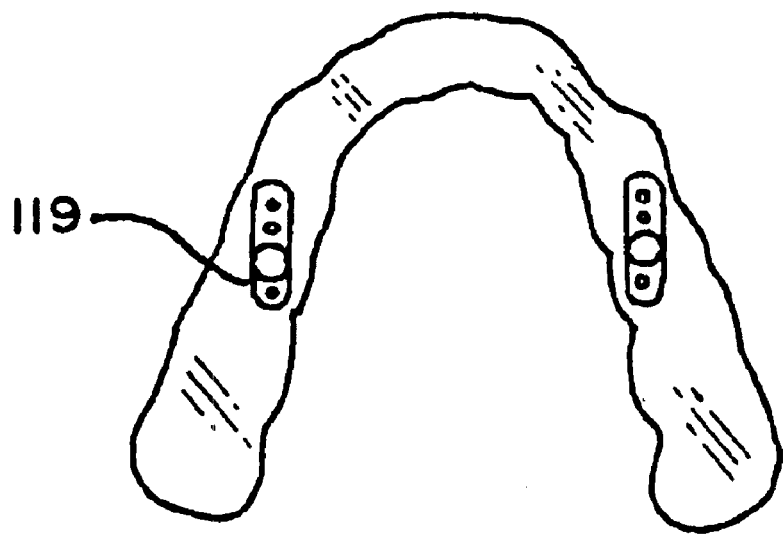
FIG. 10A is a diagrammatic bottom plan view of the area generally enclosed by the dotted curve identified by ARROW 10A in FIG. 9.
Figure 10B:
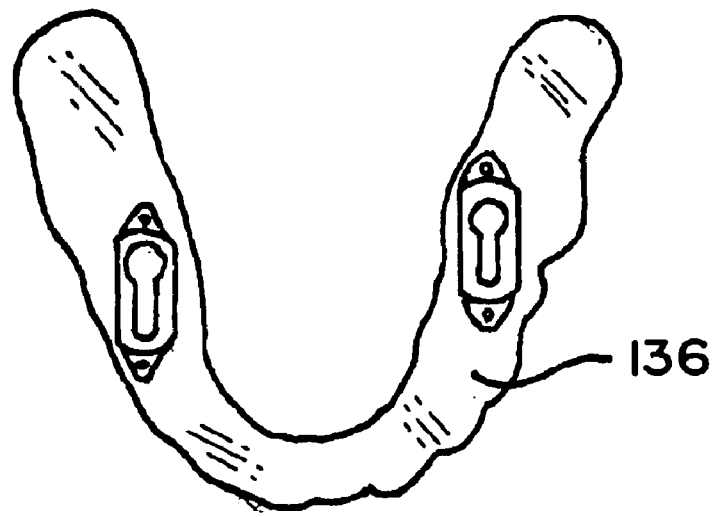
FIG. 10B is a diagrammatic bottom plan view of the area generally enclosed by the dotted curve identified by ARROW 10B in FIG. 9.

STEP 15: As shown in FIGS. 5 and 12-EEE, affix a pair of the assemblies 50 on the conformed plastic spacer layer 36, at the bite surfaces 22 of the posterior portions 20 of the teeth 18 of the lower duplicate casting 12, utilizing the wax luting agent 46.

STEP 16: As shown in FIG. 12-FFF, ascertain that the pair of assemblies 50 are parallel to each other so as to form a lower assemblage 54.

STEP 17: As shown in FIG. 12-B, make a duplicate of an original upper casting 56, forming an upper duplicate casting 58, wherein the original upper casting 56 has a gum 60, teeth 62 with supra bulges 64 and posterior portions 66 with bite surfaces 68, and wherein the upper duplicate casting 58 bas teeth 70.

STEP 18: As shown in FIGS. 3 and 12-C, survey the original upper casting 56, forming a surveying line 72 thereon.

STEP 19: As shown in FIGS. 3 and 12-D, extend the surveying line 72 approximately 1 mm past the supra bulges 64 of the teeth 62 of the original upper casting 56, toward the gum 60 of the original upper casting 56, forming an extended surveying line 74.

STEP 20: As shown in FIG. 12-E, put the original upper casting 56 aside.

STEP 21: As shown in FIG. 12-E, determine if an upper ball clasp 76 is to be used.

STEP 22: As shown in FIGS. 4 and 12-F, put the upper ball clasp 78 on the upper duplicate casting 58, If answer to STEP 21 is yes and proceed to STEP 24.

STEP 23: As shown in FIG. 12-F, proceed directly to STEP 24, if answer to STEP 21 is no.

STEP 24: As shown in FIGS. 4 and 12-F, put the upper duplicate casting 58 in the heat pressure former 32.

STEP 25: As shown in FIGS. 4 and 12-G, position another at least one plastic spacer sheet 34 on the teeth 70 of the upper duplicate casting 58.

STEP 26: As shown in FIGS. 4 and 12-H, activate the heat pressure former 32, causing the another at least one plastic spacer sheet 34 to melt and conform to the teeth 70 of the upper duplicate casting 58, forming a conformed plastic spacer layer 82 thereon.

STEP 27: As shown in FIG. 12-I, remove the upper duplicate casting 58 with the conformed plastic spacer layer 82 thereon from the heat pressure former 32 so as to form an upper assemblage 84.

STEP 28: As shown in FIG. 12-J, place the upper assemblage 84 on the articulator 38.

STEP 29: As shown in FIG. 12-GGG, close the articulator 38 to align the upper assemblage 84 and the lower assemblage 54.

STEP 30: As shown in FIG. 12-HHH, secure the male hinge parts 48 to the upper assemblage 84 using the wax luting agent 46.

STEP 31: As shown in FIG. HHH, remove the tack from the assemblies 50.

STEP 32: As shown in FIG. 12-III, open the articulator 38.

STEP 33: As shown in FIG. 12-JJJ, determine if an upper U-shaped reinforcing wire 86 and a lower U-shaped reinforcing wire 88 are to be used.

STEP 34: As shown in FIG. 12-KKK, put the put the upper U-shaped reinforcing wire 86 on the upper assemblage 84 using the wax luting agent 46, If answer to STEP 33 is yes and proceed to STEP 35.

STEP 35: As shown in FIG. 12-LLL, put the lower U-shaped reinforcing wire 88 on the lower assemblage 54 using the wax luting agent 46 and proceed to STEP 37.

STEP 36: As shown in FIG. 12-KKK, proceed directly to STEP 37, if answer to STEP 33 is no.

STEP 37: As shown in FIG. 12-MMM. remove the upper assemblage 84 from the articulator 38.

STEP 38: As shown in FIG. 12-NNN, apply a separating medium 90 to portions 92 of the upper assemblage 84 that are exposed.

STEP 39: As shown in FIG. 12-OOO, position stone 94 in a lower portion 96 of a flask 98 that has an upper portion 100.

STEP 40: As shown in FIGS. 8 and 12-OOO, place the upper assemblage 84 in the lower portion 96 of the flask 98.

STEP 41: As shown in FIGS. 8 and 12-PPP, place a wax sprue 101 on the upper assemblage 84.

STEP 42: As shown in FIGS. 8 and 12-QQQ, apply the separating medium 90 to the stone 94 that is exposed and to the upper assemblage 84.

STEP 43: As shown in FIG. 12-RRR, secure the upper portion 100 of the flask 98 to the lower portion 96 of the flask 98.

STEP 44: As shown in FIG. 12-SSS, fill the upper portion 100 of the flask 98 with an additional amount of the stone 94.

STEP 45: As shown in FIG. 12-TTT, harden contents of the flask 98, forming an upper bite block mold 106.

STEP 46: As shown in FIG. 12-UUU, remove the wax luting agent 46 and the wax sprue 101 from the upper bite block mold 106, utilizing boiling water 108.

STEP 47: As shown in FIG. 12-VVV, separate the upper portion 100 of the flask 98 from the lower portion 96 of the flask 98.

STEP 48: As shown in FIG. 12-WWW, pick out the conformed plastic spacer layer 82 from the upper bite block mold 106.

STEP 49: As shown in FIG. 12-XXX, apply the separating medium 90 to the upper bite block mold 106.

STEP 50: As shown in FIG. 12-YYY, preheat the upper portion 100 of the flask 98 and the lower portion 96 of the flask 98, under heat lamps 110.

STEP 51: As shown in FIG. 12-ZZZ, select a polyamide material 112.

STEP 52: As shown in FIG. 12-AAAA, determine if the upper ball clasp 76 and the upper U-shaped reinforcing wire 86 have been used.

STEP 53: As shown in FIG. 12-BBBB, use VALPLAST resin as the polyamide material 112, if answer to STEP 52 is yes and proceed to STEP 55.

STEP 54: As shown in FIG. 12-AAAA, use FLEXITE SUPREME-H.M. as the polyamide material 112, if answer to STEP 52 is no and proceed to STEP 55.

STEP 55: As shown in FIG. 12-CCCC, heat the polyamide material 112 forming a preheated polyamide material 114.

STEP 56: As shown in FIG. 12-DDDD, secure the upper portion 100 of the flask 98 to the lower portion 96 of the flask 98.

STEP 57: As shown in FIG. 12-EEEE, inject the preheated polyamide material 114 into the flask 98, forming an upper bite block 116 having the upper ball clasp 76 if used and if not used see FIG. 10AA, the upper U-shaped reinforcing wire 86 if used and if not used see FIG. 10AA, , and the male hinge part 48 embedded therein.

STEP 58: As shown in FIG. 12-FFFF, cool the flask 98.

STEP 59: As shown in FIG. 12-GGGG, separate the upper portion 100 of the flask 98 from the lower portion 98 of the flask 98.

STEP 60: As shown in FIG. 12-HHHH, remove the upper bite block 116 from the upper bite block mold 106.

STEP 61: As shown in FIG. 12-HHHH, remove all rough edges 118 from the upper bite block 116.

STEP 62: As shown in FIG. 12-IIII, smooth the upper bite block 116.

STEP 63: As shown in FIG. 12-IIII, check and adjust the upper bits block 116, as required.

STEP 64: As shown in FIG. 12-JJJJ, polish the upper bite block 116, forming a finished upper bite block 118.

STEP 65: As shown in FIG. 12-KKKK, transfer the finished upper bite block 118 to the original upper casting 56, forming a final upper assemblage 120.

STEP 66: As shown in FIGS. 9 and 12-LLLL, put the final upper assemblage 120 on the articulator 38.

STEP 67: As shown in FIG. 12-LLLL, position a temporary stylus 122 in each female hinge part 44.

STEP 68: As shown in FIG. 12-Q, remove the lower assemblage 54 from the articulator 38.

STEP 69: As shown in FIG. 12-R, tack the temporary stylus 122 to each female hinge part 44 with the wax luting agent 46.

STEP 70: As shown in FIG. 12-S, tack each female hinge part 44 closed with the wax luting agent 46.

STEP 71: As shown in FIG. 12-S, apply the separating medium 98 to portions 124 of the lower assemblage 54 that are exposed.

STEP 72: As shown in FIGS. 7 and 12-T, position the stone 94 in the lower portion 96 of the flask 98.

STEP 73: An shown in FIGS. 7 and 12-U, place the lower assemblage 54 in the lower portion 96 of the flask 98.

STEP 74: As shown in FIGS. 7 and 12-V, place another wax sprue 101 on the lower assemblage 54.

STEP 75: As shown in FIG. 12-W, apply the separating medium 98 to the stone 94 that is exposed and to the lower assemblage 54.

STEP 76: As shown in FIG. 12-X, secure the upper portion 100 of the flask 98 to the lower portion 96 of the flask 98.

STEP 77: Ax shown in FIG. 12-Y, fill the upper portion 100 of the flask 98 with an additional amount 128 of the stone 94.

STEP 78: As shown in FIG. 12-Z, harden contents of the flask 98, forming a lower bite block mold 130.

STEP 79: As shown in FIG. 12-AA, remove the wax luting agent 46 and the another wax sprue 101 from the lower bite block mold 13, utilizing the boiling water 108, with the lower ball clasp 30 if used and if used and if not used see FIG. 10BB, the lower U-shaped reinforcing wire 88 if used and if used and if not used see FIG. 10BB, and the female hinge part 44 retained in the lower bite block mold 130.

STEP 80: As shown in FIG. 12-BB, separate the upper portion 100 of the flask 98 from the lower portion 98 of the flask 98.

STEP 81: As shown in FIG. 12-CC, pick out the conformed plastic spacer layer 36 from the lower bite block mold 130.

STEP 82: As shown in FIG. 12-DD, apply the separating medium 90 to the lower bite block mold 130.

STEP 83: As shown in FIG. 12-EE, preheat the upper portion 100 of the flask 98 and the lower portion 96 of the flask 96, under the heat lamps 110.

STEP 84: As shown in FIG. 12-FF, select the polyamide material 112.

STEP 85: As shown in FIG. 12-GG, determine if the lower ball clasp 30 and the lower U-shaped reinforcing wire 88 have been used.

STEP 86: As shown in FIG. 12-HH, use the VALPLAST resin as the polyamide material 112, if answer to STEP 85 is yes and proceed to STEP 88.

STEP 87: As shown in FIG. 12-GG, use the FLEXITE SUPREME-H.M. as the polyamide material 112, if answer to STEP 85 is no and proceed to STEP 88.

STEP 88: An shown in FIG. 12-II, heat the polyamide material 112 forming the preheated polyamide material 114.

STEP 89: As shown in FIG. 12-JJ, secure the upper portion 190 of the flask 98 to the lower portion 98 of the flask 98.

STEP 90: As shown in FIG. 12-KK, inject the preheated polyamide material 114 into the flask 98, forming a lower bite block 132 having the lower ball clasp 30 if used, the lower U-shaped reinforcing wire 88 if used, and the female hinge part 44 embedded therein.

STEP 91: As shown in FIG. 12-LL, cool the flask 98.

STEP 92: As shown in FIG. 12-LL, separate the upper portion 100 of the flask 98 from the lower portion 96 of the flask 98.

STEP 93: As shown in FIG. 12-MM, remove the lower bite block 132 from the lower bite block mold 130.

STEP 94: As shown in FIG. 12-MM, remove the temporary stylus 122.

STEP 95: As shown in FIG. 12-NN, remove all rough edges 134 from the lower bite block 132.

STEP 96: As shown in FIG. 12-OO, smooth the lower bite block 132.

STEP 97: As shown in FIG. 12-PP, check and adjust the lower bite block 132, as required.

STEP 98: As shown in FIG. 12-PP, polish the lower bite block 132, forming a finished lower bite block 136.

STEP 99: As shown in FIG. 12-QQ, transfer the finished lower bite block 136 to the original lower casting 10, forming a final lower assemblage 138.

STEP 100: As shown in FIGS. 9 and 12-RR, put the final lower assemblage 138 in the articulator 38.

STEP 101: As shown in FIG. 12MMMM, verify accuracy of bite registration of the final upper assemblage 120 and the final lower assemblage 138.

STEP 102: As shown in FIG. 12-NNNN, determine if the bite registration is accurate.

STEP 103: As shown in FIG. 12-NNNN, adjust accordingly, if answer to STEP 102 is no.

It will be understood that each of the elements described above, or two or more together, may also find a useful application in other types of constructions differing from the types described above.

While the invention has been illustrated and described as embodied in a method of fabricating a flexible retentive bite block, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

| MATERIALS UTILIZED IN THE FABRICATING OF BITE BLOCK | |
| --- | --- |
| PRODUCT NAME | MANUFACTURED BY |
| VALPLAST resin | Valplast International Corp., 34–30 31st Street, Long Island City, NY 11106 |
| FLEXITE SUPREME-H.M. | Rapid Injection System Corp. 40 Roselle Street, Mineola, NY 11501 |

The invention claimed is:

1. A method of fabricating a flexible retentive bite block, comprising the steps of:
   a) making a duplicate of an original lower casting so as to form a lower duplicate casting, wherein the original lower casting has a gum, teeth with supra bulges and posterior portions with bite surfaces, and wherein the lower duplicate casting has teeth;

c) determining if a lower ball clasp is to used;

d) putting the lower ball clasp on the lower duplicate casting, if answer to step c) is yes;

e) putting the lower duplicate casting in a heat pressure former;

f) positioning at least one plastic spacer sheet on the teeth of the lower duplicate casting;

g) activating the heat pressure former, causing the at least one plastic spacer sheet to melt and conform to the teeth of the lower duplicate casting, forming a conformed plastic spacer layer thereon;

h) removing the lower duplicate casting with the conformed plastic spacer layer thereon from the heat pressure former;

i) putting the lower duplicate casting with the conformed plastic spacer layer thereon in an articulator;

j) putting a flat plastic spacer on a bottom of a female hinge part using a was luting agent;

k) putting a male hinge part into the female hinge part and tacking together with the wax luting agent, forming an assembly;

l) affixing a pair of the assemblies on the conformed plastic spacer layer, at the bite surfaces of the posterior portions of the teeth of the lower duplicate casting, utilizing the wax luting agent; and m) ascertaining that the pair of assemblies are parallel to each other so as to form a lower assemblage.

2. The method as defined in claim 1; further comprising the steps of:

n) making a duplicate of an original upper casting, forming an upper duplicate casting, wherein the original upper casting has a gum, teeth with supra bulges and posterior portions with bite surfaces, and wherein the upper duplicate casting has teeth; and o) putting the original upper casting aside.

3. The method as defined in claim 2; further comprising the steps of:

p) determining if an upper ball clasp is to be used; and q) putting the upper ball clasp on the upper duplicate casting, if answer to step is yes.

4. The method as defined in claim 3; further comprising the steps of:

r) putting the upper duplicate casting in the heat pressure former;

s) positioning another at least one plastic spacer sheet on the teeth of the upper duplicate casting;

t) activating the heat pressure former, causing the another at least one plastic spacer sheet to melt and conform to the teeth of the upper duplicate casting, forming a conformed plastic spacer layer thereon; and u) removing the upper duplicate casting with the conformed plastic spacer layer thereon from the heat pressure former so as to form an upper assemblage.

5. The method as defined in claim 4; further comprising the steps of:

v) placing the upper assemblage on the articulator;

w) closing the articulator to align the upper assemblage and the lower assemblage;

x) securing the male hinge parts to the upper assemblage using the wax luting agents;

y) removing the tack from the assemblies; and z) opening the articulator.

6. The method as defined in claim 5; further comprising the steps of;

aa) determining if an upper U-shaped reinforcing wire and a lower U-shaped reinforcing wire are to be used;

bb) putting the upper U-shaped reinforcing wire on the upper assemblage using the wax luting agent, if answer to step aa) is yes;

cc) putting the lower U-shaped reinforcing wire on the lower assemblage using the wax luting agent ;and dd) removing the upper assemblage from the articulator.

7. The method as defined in claim 6, further comprising the steps of:

ee) applying a separating medium to portions of the upper assemblage that are exposed;

ff) positioning stone in a lower portion of a flask that has an upper portion;

gg) placing the upper assemblage in the lower portion of the flask;

hh) placing a wax sprue on the upper assemblage;

ii) applying the separating medium to the stone that is exposed and to the upper assemblage;

jj) securing the upper portion of the flask to the lower portion of the flask;

kk) filling the upper portion of the flask with an additional amount of the stone; and ll) hardening contents of the flask, forming an upper bite block mold.

8. The method as defined in claim 7; further comprising the steps of:

mm) removing the wax luting agent and the wax sprue from the upper bite block mold, utilizing boiling water;

nn) separating the upper portion of the flask from the lower portion of the flask; and oo) picking out the conformed plastic spacer layer from the upper bite block mold.

9. The method as defined in claim 8, further comprising the steps of:

pp) applying the separating medium to the upper bite block mold;

qq) preheating the upper portion of the flask and the lower portion of the flask, under heat lamps;

rr) selecting a polyamide material;

ss) determining if the upper ball clasp and the upper U-shaped reinforcing wire have been used;

tt) using a biocompatible nylon thermoplastic resin as the polyamide material, if answer to step ss) is yes; and uu) using a biocompatible high molecular monomer free thermoplastic as the polyamide material, if answer to step ss) is no.

10. The method as defined in claim 9; further comprising the steps of:

vv) heating the polyamide material forming a preheated polyamide material;

ww) securing the upper portion of the flask to the lower portion of the flask;

xx) injecting the preheated polyamide material into the flask, forming an upper bite block having the upper ball clasp if used, the upper U-shaped reinforcing wire if used, and the male hinge part embedded therein;

yy) cooling the flask;

zz) separating the upper portion of the flask from the lower portion of the flask; and aaa) removing the upper bite block from the upper bite block mold.

11. The method as defined in claim 10; further comprising the steps of;
- bbb) removing all rough edges from the upper bite block;
- ccc) smoothing the upper bite block;
- ddd) checking and adjusting the upper bite block, as required; and
- eee) polishing the upper bite block, forming a finished upper bite block.

12. The method as defined in claim 11; further comprising the steps of:
- fff) transferring the finished upper bite block to the original upper casting, forming a final upper assemblage; and
- ggg) putting the final upper assemblage on the articulator.

13. The method as defined in claim 12; further comprising the steps of:
- hhh) positioning a temporary stylus in each female hinge part;
- iii) removing the lower assemblage from the articulator;
- jjj) tacking the temporary stylus to each female hinge part with the wax luting agent; and
- kkk) tacking each female hinge part closed with the wax luting agent.

14. The method as defined in claim 13; further comprising the steps of:
- lll) applying the separating medium to portions of the lower assemblage that are exposed;
- mmm) positioning the stone in the lower portion of the flask;
- nnn) placing the lower assemblage in the lower portion of the flask;
- ooo) placing another wax sprue on the lower assemblage;
- ppp) applying the separating medium to the stone that is exposed and to the lower assemblage;
- qqq) securing the upper portion of the flask to the lower portion of the flask;
- rrr) filling the upper portion of the flask with an additional amount of the stone; and
- sss) hardening contents of the flask, forming a lower bite block mold.

15. The method as defined in claim 14; further comprising the steps of:
- ttt) removing the wax luting agent and the another wax sprue from the lower bite block mold, utilizing the boiling water, with the lower ball clasp if used, the lower U-shaped reinforcing wire if used, and the female hinge part retained in the lower bite block mold;
- uuu) separating the upper portion of the flask from the lower portion of the flask; and
- vvv) picking out the conformed plastic spacer layer from the lower bite block mold.

16. The method as defined in claim 15; further comprising the steps of:
- www) applying the separating medium to the lower bite block mold;
- xxx) preheating the upper portion of the flask and the lower portion of the flask, under the heat lamps;
- yyy) selecting the polyamide material;
- zzz) determining if the lower ball clasp and the lower U-shaped reinforcing wire have been used;
- aaaa) using the biocompatible nylon thermoplastic resin as the polyamide material, if answer to step zzz) is yes; and
- bbb) using the biocompatible high molecular monomer free thermoplastic as the polyamide material, if answer to step zzz) is no.

17. The method as defined in claim 16; further comprising the steps of:
- cccc) heating the polyamide material forming the preheated polyamide material;
- dddd) securing the upper portion of the flask to the lower portion of the flask;
- eeee) injecting the preheated polyamide material into the flask, forming a lower bite block having the lower ball clasp if used, the lower U-shaped reinforcing wire if used, and the female hinge part embedded therein;
- ffff) cooling the flask;
- gggg) separating the upper portion of the flask from the lower portion of the flask; and
- hhhh) removing the lower bite block from the lower bite block mold.

18. The method as defined in claim 17; further comprising the steps of:
- iiii) removing the temporary stylus;
- jjjj) removing all rough edges from the lower bite block;
- kkkk) smoothing the lower bite block;
- llll) checking and adjusting the lower bite block, as required; and
- mmmm) polishing the lower bite block, forming a finished lower bite block.

19. The method as defined in claim 18; further comprising the steps of:
- nnnn) transferring the finished lower bite block to the original lower casting, forming a final lower assemblage;
- oooo) putting the final lower assemblage in the articulator;
- pppp) verifying accuracy of bite registration of the final upper assemblage and the final lower assemblage;
- qqqq) determining if the bite registration is accurate; and
- rrrr) adjusting accordingly, if answer to step gggg) is no.

* * * * *